US010781243B2

(12) United States Patent
Blankenstein et al.

(10) Patent No.: US 10,781,243 B2
(45) Date of Patent: Sep. 22, 2020

(54) COMBINED T CELL RECEPTOR GENE THERAPY OF CANCER AGAINST MHC I AND MHC II-RESTRICTED EPITOPES OF THE TUMOR ANTIGEN NY-ESO-1

(71) Applicant: MAX-DELBRÜCK-CENTRUM FÜR MOLEKULARE MEDIZIN IN DER HELMHOLTZ-GEMEINSCHAFT, Berlin (DE)

(72) Inventors: Thomas Blankenstein, Berlin (DE); Lucia Poncette, Berlin (DE); Xiaojing Chen, Berlin (DE)

(73) Assignee: MAX-DELBRÜCK-CENTRUM FÜR MOLEKULARE MEDIZIN IN DER HELMHOLTZ-GEMEINSCHAFT, Berlin (DE)

( * ) Notice: Subject to any disclaimer, the term of this patent is extended or adjusted under 35 U.S.C. 154(b) by 160 days.

(21) Appl. No.: 15/558,021

(22) PCT Filed: Mar. 11, 2016

(86) PCT No.: PCT/EP2016/055242
§ 371 (c)(1),
(2) Date: Sep. 13, 2017

(87) PCT Pub. No.: WO2016/146505
PCT Pub. Date: Sep. 22, 2016

(65) Prior Publication Data
US 2018/0057560 A1 Mar. 1, 2018

(30) Foreign Application Priority Data
Mar. 13, 2015 (EP) .................................... 15159001

(51) Int. Cl.
| | | |
|---|---|---|
| *C07K 14/725* | (2006.01) | |
| *C07K 14/47* | (2006.01) | |
| *A01K 67/027* | (2006.01) | |
| *A61K 38/00* | (2006.01) | |
| *A61K 48/00* | (2006.01) | |

(52) U.S. Cl.
CPC ...... *C07K 14/7051* (2013.01); *A01K 67/0278* (2013.01); *C07K 14/4748* (2013.01); *A01K 2217/052* (2013.01); *A01K 2227/105* (2013.01); *A61K 38/00* (2013.01); *A61K 48/00* (2013.01); *C07K 2317/565* (2013.01)

(58) Field of Classification Search
CPC .................................................. C07K 14/7051
See application file for complete search history.

(56) References Cited

U.S. PATENT DOCUMENTS

2016/0289760 A1* 10/2016 Suzuki ................. C12Q 1/6881

FOREIGN PATENT DOCUMENTS

| JP | WO2008/108257 | * | 2/2008 | ............. C12N 15/00 |
|---|---|---|---|---|
| JP | WO2008/108257 | * | 9/2008 | ............. C12N 15/00 |
| JP | WO2015/075939 | * | 5/2015 | ............. C12N 15/09 |
| WO | 01/55393 A2 | | 8/2001 | |
| WO | 2012/038055 A1 | | 3/2012 | |
| WO | 2013/177247 A1 | | 11/2013 | |
| WO | 20140118236 | | 7/2014 | |
| WO | WO2014/182197 | * | 11/2014 | ............... C12Q 1/68 |

OTHER PUBLICATIONS

Zhao et al. "Primary Human Lymphocytes Transduced with NY-ESO-1 Antigen-Specific TCR Genes Recognize and Kill Diverse Human Tumor Cell Lines." J Immunol 2005; 174:4415-4423. (Year: 2005).*
Alignment SEQ ID No. 20 (15/558021) and SEQ ID No. 1971 (WO2008/108257) (Year: 2019).*
Alignment SEQ ID No. 3 (15/558021) and SEQ ID No. 61 (WO2014/182197) (Year: 2019).*
Alignment SEQ ID No. 1 (15/558021) and SEQ ID No. 1955 (US2016/0289760) (Year: 2020).*
Leisegang, M. et al. "Targeting human melanoma neoantigens by T cell receptor gene therapy", The Journal of Clinical Investigations, vol. 126, No. 3, Mar. 2016, pp. 854-858.
Linnemann, C. et al. "High-throughput identification of antigen-specific TCRs by TCR gene capture", Technical Reports, nature medicine, vol. 19, No. 11, Nov. 2013, pp. 1534-1543.
Robbins, P. et al. "A Pilot Trial Using Lymphocytes Genetically Engineered with an NY-ESO-1-Reactive T-cell Receptor: Long-term Follow-up and Correlates with Response", Clinical Cancer Research; 21(5), Mar. 1, 2015, pp. 1019-1027.

(Continued)

*Primary Examiner* — Scott Long
(74) *Attorney, Agent, or Firm* — Meunier Carlin & Curfman LLC

(57) ABSTRACT

The present invention relates to the field of immunotherapy, in particular adoptive T cell therapy or T cell receptor (TCR) gene therapy of cancer. The invention provides a nucleic acid encoding at least one T cell receptor alpha chain construct and/or TCR beta chain construct of a TCR construct capable of specifically binding to an epitope from NY-ESO-1 (also designated CTAG-1) in complex with a human MHC, wherein the TCR alpha chain construct and/or the TCR beta chain construct comprises a complementarity determining region 3 (CDR3) having at least 90% sequence identity to an amino acid selected from SEQ ID NO: 1-20. The invention provides TCR constructs restricted to an epitope from NY-ESO-1 presented on MHC I, and, for the first time, TCR constructs restricted to an epitope from NY-ESO-1 presented on MHC II molecules, and thus enables a combined adoptive T cell therapy with both recombinant CD4+ and re-combinant CD8+ T cells. The invention also provides proteins and host cells corresponding to said TCR constructs, as well as the medical use of such constructs, in particular, in the diagnosis, prevention, and/or treatment of a proliferative or viral disease, wherein, preferably, both TCR constructs restricted to MHC I and MHC II molecules are provided in a kit. The invention also relates to a mouse transgenic for the human TCR loci and human HLA-DR4, ABabDR4 mouse.

43 Claims, 5 Drawing Sheets

Figure 1:
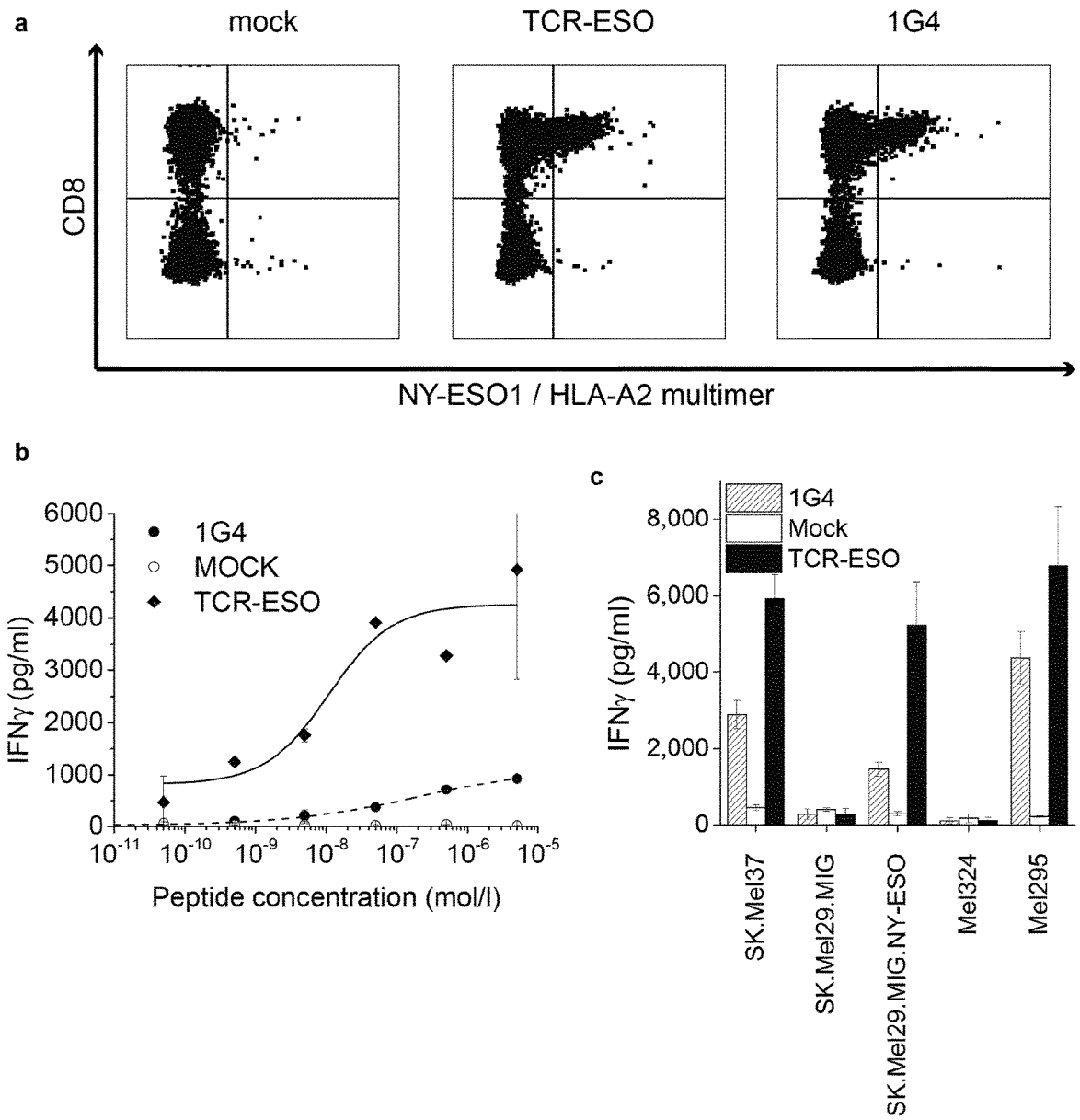

Specification includes a Sequence Listing.

(56) References Cited

OTHER PUBLICATIONS

International Search Report dated Jul. 20, 2016, from International Application No. PCT/EP2016/055242, 7 pages.
Written Opinion dated Jul. 20, 2016, from International Application No. PCT/EP2016/055242, 9 pages.
Bos, et al., "CD4 T-Cell Help in the Tumor Milieu Is Required for Recruitment and Cytolytic Function of CD8 T Lymphocytes", Cancer Research; 70)21) Nov. 1, 2010; 8369-8377.
Chen, et al., "Structural and kinetic basis for heightened immunogenicity of T cell vaccines", JEM vol. 201, No. 8, Apr. 18, 2005, 1243-1255.
Chervin, et al., "Engineering higher affinity T cell receptors using a T cell display system", Journal of Immunological Methods 339 (2008) 175-184.
Ito, et al., "HLA-DR4-IE Chimeric Class II Transgenic, Murine Class II-Deficient Mice Are Susceptible to Experimental Allergic Encephalomyelitis", J. Exp. Med., vol. 183 Jun. 1996, 2635-2644.
Kammertoens, et al., "Making and circumventing tolerance to cancer", Eur. J. Immunol., 2009, 39: 2345-2353.
Li, et al., "Transgenic mice with a diverse human T cell antigen receptor repertoire", Nature Medicine, vol. 16, No. 9, Sep. 2010, 1029-1035.
Linette, et al., "Cardiovascular toxicity and titin cross-reactivity of affinity-enhanced T cells in myeloma and melanoma", Blood, Aug. 8, 2013, vol. 122, No. 6, 863-871.
Morgan, et al., "Cancer Regression and Neurological Toxicity Following Anti-MAGE-A3 TCR Gene Therapy", J Immunother 2013:vol. 36, No. 2:133-151.
Restifo, et al., "Adoptive immunotherapy for cancer: harnessing the T cell response", Nature vol. 12, Apr. 2012, 270-281.
Robbins, et al., "Single and Dual Amino Acid Substitutions in TCR CDRs Can Enhance Antigen-Specific T Cell Functions", J Immunol 2008; 180:6116-6131.
Robbins, et al., "Tumor Regression in Patients With Metastatic Synovial Cell Sarcoma and Melanoma Using Genetically Engineered Lymphocytes Reactive With NY-ESO-1", J Clin Oncol 29:917-924.
Schietinger, et al., "Bystander killing of cancer requires the cooperation of CD4+ and CD8+ T cells during the effector phase", JEM vol. 2017, No. 11, 2469-2477.
Sommermeyer et al., "Minimal Amino Acid Exchange in Human TCR Constant Regions Fosters Improved Function of TCR Gene-Modified T Cells", J Immunol 2010; 184: 6223-6231.
Tran, et al., "Cancer Immonotherapy Based on Mutation-Specific CD4+ T Cells in a Patient with Epithelial Cancer", Science vol. 344, May 9, 2014, 641-645.
Uckert, et al., "TCR Transgenes and transgene cassettes for TCR gene therapy: status in 2008", Cancer Immunol Immunother, 2009 58:809-822.
Zhao, et al., "Transduction of an HLA-DP4-restricted NY-ESO-1-specific TCR into Primary Human CD4+ Lymphocytes", J Immunother 2006; 29:398-406.

* cited by examiner

COMBINED T CELL RECEPTOR GENE THERAPY OF CANCER AGAINST MHC I AND MHC II-RESTRICTED EPITOPES OF THE TUMOR ANTIGEN NY-ESO-1

The present invention relates to the field of immunotherapy, in particular adoptive T cell therapy or T cell receptor (TCR) gene therapy of cancer. The invention provides a nucleic acid encoding at least one T cell receptor alpha chain construct and/or TCR beta chain construct of a TCR construct capable of specifically binding to an epitope from NY-ESO-1 (also designated CTAG-1) in complex with a human MHC, wherein the TCR alpha chain construct and/or the TCR beta chain construct comprises a complementarity determining region 3 (CDR3) having at least 90% sequence identity to an amino acid selected from SEQ ID NO: 1-20. The invention provides TCR constructs restricted to an epitope from NY-ESO-1 presented on MHC I, and TCR constructs restricted to an epitope from NY-ESO-1 presented on MHC II molecules, and thus enables a combined adoptive T cell therapy with both recombinant CD4+ and recombinant CD8+ T cells. The invention also provides corresponding proteins and host cells, as well as the medical use of such constructs, in particular, in the diagnosis, prevention and/or treatment of a proliferative or viral disease, wherein, preferably, both TCR constructs restricted to MHC I and MHC II molecules are provided in a kit. The invention also relates to a mouse transgenic for the human TCR loci and human HLA-DR4, ABabDR4 mouse.

Despite remarkable technological advancements in the diagnosis and treatment options available to patients diagnosed with cancer, the prognosis still often remains poor and many patients cannot be cured Immunotherapy holds the promise of a potent, yet targeted, treatment to patients diagnosed with various tumors, with the potential of eradicating the malignant tumor cells without damaging normal tissues. In theory, the T cells of the immune system are capable of recognizing protein patterns specific for tumor cells and mediating their destruction through a variety of effector mechanisms. However, in practice, T cells of patients are often tolerant to tumor antigens. Adoptive T-cell therapy is an attempt to harness and amplify the tumor-eradicating capacity of a patient's own T cells and then return these T cells to the patient in such a state that they effectively eliminate residual tumor, however without damaging healthy tissue. Although this approach is not new to the field of tumor immunology, still many drawbacks in the clinical use of adoptive T cell therapy impair the full use of this approach in cancer treatments.

A TCR is a heterodimeric cell surface protein of the immunoglobulin super-family which is associated with invariant proteins of the CD3 complex involved in mediating signal transduction. TCRs exist in αβ and γδ forms, which are structurally similar, but have quite distinct anatomical locations and probably functions. The alpha and beta chains of native heterodimeric αβTCR are transmembrane proteins, which each comprise two extracellular domains, a membrane-proximal constant domain, and a membrane-distal variable domain. Each of the constant and variable domains includes an intra-chain disulfide bond. The variable domains contain the highly polymorphic loops analogous to the complementarity determining regions (CDRs) of antibodies.

The variable region of each TCR chain comprises variable and joining segments, and in the case of the beta chain also a diversity segment. Each variable region comprises three CDRs (Complementarity Determining Regions) embedded in a framework sequence, one being the hypervariable region named CDR3. There are several types of alpha chain variable (Vα) regions and several types of beta chain variable (Vβ) regions distinguished by their framework, CDR1 and CDR2 sequences, and by a partly defined CDR3 sequence. Unique TRAY or TRBV numbers are given to Vα or Vβs by IMGT nomenclature. T cell receptor specificity is mainly determined by the CDR3 regions.

The use of TCR gene therapy overcomes a number of current problems. It allows equipping patients' own T cells with desired specificities and generation of sufficient numbers of T cells in a short period of time, avoiding their exhaustion. The TCR may be transduced into central memory T cells or T cells with stem cell characteristics, which may ensure better persistence and function upon transfer. TCR-engineered T cells may be infused into cancer patients rendered lymphopenic by chemotherapy or irradiation, allowing efficient engraftment but inhibiting immune suppression.

The biggest hurdle for gene therapy to overcome remains the identification of antigens that can be targeted to destroy the cancer without causing untoward toxicity to normal tissues (Restifo et al, 2012, Nature Reviews 12, 269-281). Cancer-testis antigens are normally expressed by germline cells in the testes and fetal ovaries, but they are also expressed by many types of tumors. Cancer-testis antigens are among the most attractive targets because of their shared expression among many tumor types and their lack of expression in normal tissues. Raising specific T cells against this group of antigens presents a good opportunity in cancer therapy.

NY-ESO proteins constitute a sub-family of cancer-testis antigens which are expressed mainly, but not exclusively, in the germline. They are however also expressed in various human cancers e.g., melanomas, lung carcinomas, synovial sarcoma, and cancers of the head and neck, oesophagus and bladder, where they are associated with, and may drive, malignancy. This specific expression of NY-ESO-1 antigens in tumors and not the normal surrounding healthy tissue makes this family of antigens very interesting for targeted adoptive T cell transfer. A recent report targeting NY-ESO-1 using autologous T cells with genetically engineered TCRs showed evidence of objective clinical responses in 47% patients with metastatic melanoma and 80% of patients with metastatic synovial sarcoma, all of whom were heavily pretreated with standard therapies. No toxicity against normal tissue was observed (Robbins et al., 2011, J. Clin. Oncol. 29, 917-924).

So far, TCRs specific for MHC I restricted epitopes of NY-ESO-1 derived from human patients or transgenic mice have been identified (Robbins et al., 2011, J. Clin. Oncol. 29, 917-924; Linnemann et al., 2013, Nature Med. 19, 1534-1541); and a TCR specific for an MHC II (HLA-DP4) restricted epitope of NY-ESO-1 derived from a human patient has been disclosed (Zhao et al., 2006, J Immunother. 29(4):398-406).

However, increased efficiency of therapy is desired. Drawbacks in the state of the art may relate to unsatisfactory affinity of TCRs for gene therapy, or to unsatisfactory efficacy of the T cells in the host. For example, Schietinger et al. (2010, J. Exp. Med. 207, 2469-2477) and Bos et al. (2010, cancer Res. 70(21), 8368-8377) describe that, in the murine model, CD8+ cells alone are often insufficient to eradicate tumors, but that the cooperation of CD4+ and CD8+ T cells may be required.

In view of the above described drawbacks, the present inventors addressed the problem of providing new TCR constructs capable of specifically binding to tumor antigens such as NY-ESO-1, in particular, TCR constructs recognizing epitopes of such antigens in complex with human MHC II or human MHC I, respectively. This problem is solved by the subject matter of the claims.

The inventors surprisingly found that TCR constructs targeting epitopes from tumor antigens such as NY-ESO-1 which are derived from mice are superior to TCR constructs derived from human patients with regard to their affinity and/or functional characteristics, e.g., IFN-gamma production in response to stimulation with the respective peptide/MHC complex.

In particular, the present invention provides a nucleic acid encoding at least one T cell receptor (TCR) alpha chain construct and/or, TCR beta chain construct of a TCR construct capable of specifically binding to an epitope from NY-ESO-1 (also: CTAG-1) in complex with a human MHC, wherein the TCR alpha chain construct and/or the TCR beta chain construct comprises a complementarity determining region 3 (CDR3) having at least 70%, at least 80%, at least 90%, at least 95% or, preferably, 100% sequence identity to an amino acid selected from SEQ ID NO: 1-20.

In the context of the present invention, "a" is understood to mean "one or more" unless expressly stated otherwise. Accordingly, for example, if the TCR construct of the invention contains both alpha and beta chain constructs, as preferred throughout the invention, it may be encoded by either one or two nucleic acids. The alpha and beta chain constructs together are capable of specifically binding to an epitope from NY-ESO-1 in complex with the human MHC. As intermediate products, the alpha and beta chain constructs are also subject matter of the invention by themselves.

SEQ ID NO: 1-20 correspond to CDR3 regions of TCR identified in the present invention and shown in Tables 1 and 2 of this application. SEQ ID NO: 1-9 correspond to CDR3 regions of TCR alpha chain constructs of the invention capable of recognizing the HLA-DRA/HLA-DRB1*0401 (HLA-DR4)-, i.e., MHC II-restricted NY-ESO-1$_{116-135}$ epitope (LPVPGVLLKEFTVSGNILTI, SEQ ID NO: 21), SEQ ID NO: 10-18 correspond to CDR3 regions of TCR beta chain constructs of the invention capable of recognizing the HLA-DR4-restricted NY-ESO-1$_{116-135}$ epitope. These are the first isolated TCRs specific for an HLA-DR4-restricted epitope of NY-ESO-1. They were derived from a mouse transgenic for the human TCR loci and human HLA-DR4.

Accordingly, in a preferred embodiment, the TCR construct of the invention is capable of specifically binding to the epitope consisting of NY-ESO-1$_{116-135}$ epitope (SEQ ID NO: 21) in complex with HLA-DR4, wherein the TCR alpha chain construct comprises a CDR3 having at least 90% sequence identity, preferably, 100% sequence identity, to an amino acid selected from SEQ ID NO: 1-9. The TCR beta chain construct comprises a complementarity determining region 3 (CDR3) having at least 90% sequence identity, preferably, 100% sequence identity, to an amino acid selected from SEQ ID NO: 10-18. Of course, the TCR alpha and beta chain constructs are paired in a TCR construct of the invention in a way which enables recognition of the epitope on the MHC molecule, in particular, as taught in Table 1. The TCR alpha and/or beta chain constructs may comprise the CDR1, CDR2 and CDR3 regions shown in Table 3. Preferably, the TCR alpha and/or beta chain constructs comprise the CDR3 regions and the variable regions as shown in Table 1.

The TCR alpha chain construct may comprise a variable region comprising a sequence having at least 80%, at least 90% or 100% sequence identity to SEQ ID 22-30, which is optionally encoded by a nucleic acid having a codon-optimized sequence selected from SEQ ID 31-39. The TCR alpha chain construct preferably comprises a sequence having at least 80%, at least 90% or 100% sequence identity to any of SEQ ID NO: 40-48, and is optionally encoded by a codon-optimized nucleic acid having a sequence of any of SEQ ID NO: 49-57.

TABLE 1

List of HLA-DR4 restricted TCRs recognizing NY-ESO-1$_{116-135}$ isolated from ABabDR4 mice
HLA-DR4 restricted T cell receptors recognizing NY-ESO-1$_{116-135}$

| | | T cell receptor α chain | T cell receptor β chain |
|---|---|---|---|
| TCR3598 | | TRAV12-3 -CAMRQGGSEKLVF (SEQ ID NO: 1)- TRAJ57 | TRBV2 -CASSGQGAGTQYF (SEQ ID NO: 10)- TRBJ2-5 |
| TCR3598_2 | | TRAV9-2 -CALRDSGGGADGLTF (SEQ ID NO: 2)- TRAJ45 | TRBV2 -CASSVMTGLNTEAFF (SEQ ID NO: 11)- TRBJ1-1 |
| TCR5412 | | TRAV8-6 -CAVTLNRDDKIIF (SEQ ID NO: 3)- TRAJ30 | TRBV7-9 -CASSLDRPYNEQFF (SEQ ID NO: 12)- TRBJ2-1 |
| TCR5412_2 | | TRAV8-6 -CAVTRNSGNTPLVF (SEQ ID NO: 4)- TRAJ29 | TRBV12-3 -CASSFLASVGYEQYF (SEQ ID NO: 13)- TRBJ2-7 |
| TCR5412_3 | | TRAV35 -CAGQQNSGGSNYKLTF (SEQ ID NO: 5)- TRAJ53 | TRBV18 -CASSPPLGEQYF (SEQ ID NO: 14)- TRBJ2-7 |
| TCR3600 | | TRAV41 -CAVPNSGNTPLVF (SEQ ID NO: 6)-TRAJ29 | TRBV2 -CASSVIYEQYF (SEQ ID NO: 15)- TRBJ2-7 |
| TCR5712 | | TRAV41 -CAVPNSGNTPLVF (SEQ ID NO: 7)- TRAJ29 | TRBV2 -CASSIIYEQYF (SEQ ID NO: 16)- TRBJ2-7 |
| TCR5415 | | TRAV41 -CAVPNSGNTPLVF (SEQ ID NO: 8)- TRAJ29 | TRBV2 -CASSVYYEQYF (SEQ ID NO: 17)- TRBJ2-7 |

TABLE 1-continued

List of HLA-DR4 restricted TCRs recognizing NY-ESO-1$_{116-135}$ isolated from ABabDR4 mice HLA-DR4 restricted T cell receptors recognizing NY-ESO-1$_{116-135}$

| | T cell receptor α chain | T cell receptor β chain |
|---|---|---|
| TCR5713 | TRAV5 -CAEANQAGTALIF (SEQ ID NO: 9) - TRAJ15 | TRBV2 -CASSSGLAGVTGELFF (SEQ ID NO: 18) - TRBJ2-2 |

The TCR beta chain construct may comprise a variable region comprising a sequence having at least 80%, at least 90% or 100% sequence identity to SEQ ID NO: 58-66, which is optionally encoded by a codon-optimized nucleic acid having a sequence selected from SEQ ID NO: 67-75. The TCR beta chain construct preferably comprises a sequence having at least 80%, at least 90% or 100% sequence identity to any of SEQ ID NO: 76-84 and is optionally encoded by a codon-optimized nucleic acid of any of SEQ ID NO: 85-93.

The constructs defined by a certain sequence identity in their variable region or over their complete length preferably comprise the respective CDR3 region having 100% homology to the defined CDR3 regions, as shown, e.g. in Table 1.

The invention also provides a single chain nucleic acid construct, wherein, e.g. TCR alpha and beta chain constructs are separated by a P2A element. In such single chain nucleic acid constructs, the complete TCR construct may be encoded by a nucleic acid of any of SEQ ID NO: 94-102.

The invention also relates to a mouse comprising nucleic acids encoding the complete unrearranged human TCR alpha and beta gene loci, and expressing rearranged TCR derived from the loci on its CD4+T cells, further expressing human HLA-DR4 fused to the non-antigen-binding domains of mouse I-E, wherein the mouse is deficient for mouse TCRs and mouse MHC class II molecules. Hence, ABabDR4 express a diverse human TCR repertoire with CD4+T cells having HLA-DR4 restriction. The TCR constructs of the invention described above, which recognize an NY-ESO-1 epitope in complex with HLA-DR4, were all derived from such mice, designated ABabDR4 mice, which are also an object of the present invention. The invention also relates to the use of these mice for preparing a TCR specific for an epitope presented on HLA-DR4, in particular, a TCR construct of the invention.

As opposed to humans, ABabDII mice or ABabDR4 mice are not tolerant to human tumor associated antigens (TAAs), such as NY-ESO-1. Therefore, when vaccinated with a human TAA, ABabDII mice generate an efficient adaptive immune response against those foreign antigens including the expansion of high avidity antigen specific T cells. After immunization with a suitable human TAA, the genetic information coding for the high avidity TCRs of the ABabDII mice can be extracted. These TCRs can subsequently be re-expressed in T cells from tumor patients through retroviral transduction. Those re-targeted T cells can be transferred back into the patient fighting the tumor (FIG. 1 of WO2014118236).

Using the human TCR transgenic mice, any human peptide sequence not encoded by the mouse genome is thus suitable for immunization and will yield TCRs with optimal affinity. Optimal affinity means that the T cells are restricted to human self-MHC molecules and recognize the peptide antigen as foreign, e.g. represent the non-tolerant repertoire. By using peptide/MHC multimers, specific T cells of the transgenic mice can be sorted, human TCRs isolated, e.g. by single cell PCR, the TCRs optimized for efficient expression while avoiding mispairing with endogenous TCR and used for transduction of patients' T cells with viral vectors (Uckert et al., 2009, Cancer Immunol Immunother 58, 809-22; Kammertoens et al., 2009, Eur J Immunol 39, 2345-53.

The TCR constructs of the invention described above are derived from a mouse transgenic for the human TCR loci and human MHC, in particular, HLA-DR4, i.e., the ABabDR4 mouse. "derived from" is intended to mean that at least the CDR3 sequence(s), preferably, the variable regions, of the TCR construct (or the respective alpha/beta chain constructs) are identical to or have the level of sequence identity defined above to the sequences provided by the mouse TCRs in the examples below. It is possible, but not required, that the nucleic acids are physically derived, e.g., by PCR, from the nucleic acids encoding the mouse TCR. As described elsewhere in detail, modifications are possible.

CD8+ T cells in ABabDII mice harbor human T cell receptors (TCRs) which recognize antigens presented by human MHC class I molecules, HLA-A*0201 (HLA-A2) (Li et al., 2010, Nature Medicine 16, 1029-34). A TCR recognizing a NY-ESO-1 epitope restricted to HLA-A2 and derived from an ABabDII mouse has been previously described (Linnemann et al., Nature Medicine 19, 1534-1541. The present invention provides a TCR recognizing a NY-ESO-1 epitope restricted to HLA-A2 (SEQ ID NO: 103) and derived from an ABabDII mouse which is shown to be functionally superior to a respective TCR, TCR 1G4 derived from a human patient.

TABLE 2

Sequence of TCR-ESO recognizing NY-ESO-1$_{157-165}$ isolated from an ABabDII mouse.

HLA-A2 restricted TCR-ESO recognizing NY-ESO-1$_{157-165}$

| T cell receptor α chain | T cell receptor β chain |
|---|---|
| TRAV25 -CAGEGNYGQNFVF (SEQ ID NO: 19) - TRAJ26 | TRBV12-4 -CASNIAGGYNEQFF (SEQ ID NO: 20) - TRBJ2-1 |

Thus, the invention also provides a TCR construct capable of recognizing an NY-ESO-1 epitope in combination with MHC I, in particular, HLA-A2. SEQ ID NO: 19 correspond to the CDR3 region of a TCR alpha chain construct of the invention capable of recognizing the HLA-A2-, i.e. MHC I-restricted NY-ESO-1$_{157-165}$ epitope (SLLMWITQC, SEQ ID NO: 103), SEQ ID NO: 20 correspond to the CDR3 region of a TCR beta chain construct of the invention capable of recognizing the HLA-A2 restricted NY-ESO-1$_{157-165}$ epitope. It was surprising to discover that this TCR provided by the present invention has, as shown below, a higher affinity than the other TCR which had previously been isolated from a human This TCR construct is capable of specifically binding to the epitope consisting of SEQ ID NO: 103 in complex with HLA-A2, wherein the TCR alpha chain construct comprises a complementarity determining region 3 (CDR3) having at least 90% sequence identity, preferably, 100% sequence identity, to SEQ ID NO: 19 and/or the TCR beta chain construct comprises a complementarity determining region 3 (CDR3) having at least 90% sequence identity, preferably, 100% sequence identity, to SEQ ID NO: 20.

Said TCR alpha chain construct may comprise a variable region comprising a sequence having at least 80%, at least 90% or 100% sequence identity to SEQ ID 104, which is optionally encoded by the codon-optimized nucleic acid of SEQ ID 105. The TCR alpha chain construct may comprise a sequence having at least 80%, at least 90% or 100% sequence identity to SEQ ID NO: 106, and is optionally encoded by the codon-optimized nucleic acid of SEQ ID NO: 107.

Said TCR beta chain construct may comprises a variable region comprising a sequence having at least 80%, at least 90% or 100% sequence identity to SEQ ID NO 106, which is optionally encoded by the codon-optimized nucleic acid of SEQ ID 108. The TCR beta chain construct may comprise a sequence having at least 80%, at least 90% or 100% sequence identity to SEQ ID NO: 109, which is optionally encoded by the codon-optimized nucleic acid of SEQ ID NO: 110.

The TCR construct may comprise the CDR1, CDR2 and CDR3 regions shown in Table 3. The TCR construct may also comprise the CDR3 regions and variable regions as shown in Table 2.

Figure 4:
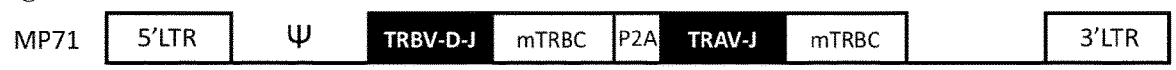

The invention also provides a single chain nucleic acid construct, wherein, e.g. TCR alpha and beta chain constructs are separated by a P2A element. FIG. 4 provides exemplary constructs. Such TCR construct may be encoded by a nucleic acid of SEQ ID ON: 111.

All nucleic acid sequences provided above have been codon-optimized for expression in human cells.

The TCR alpha chain construct and/or TCR beta chain construct or TCR construct of the invention preferably is a vector. Suitable vectors include those designed for propagation and expansion, or for expression or both, such as plasmids and viruses. The vector may be an expression vector suitable for expression is a host cell selected from the group comprising a human T cell or a human T cell precursor, preferably, a human T cell such as CD8+ T cell, CD4+ T cell, central-memory T cell, effector-memory T cell, stem cell-like T cell. The vector may be a viral vector, e.g. a retroviral, in particular gamma-retroviral or lentiviral vector. Examples of suitable expression vectors include the retroviral vector MP71 shown in FIG. 4. The recombinant expression vector comprises regulatory sequences, such as transcription and translation initiation and termination codons, which are specific to the type of host cell (e.g., bacterium, fungus, plant, or animal) into which the vector is to be introduced and in which the expression of the nucleic acid of the invention shall be performed. Furthermore, the vector of the invention may include one or more marker genes, which allow for selection of transformed or transfected hosts. The recombinant expression vector can comprise a native or, preferably, heterologous promoter operably linked to the nucleotide sequence encoding the construct of the invention, or to the nucleotide sequence which is complementary to or which hybridizes to the nucleotide sequence encoding the constructs of the invention. The selection of promoters includes, e.g., strong, weak, inducible, tissue-specific and developmental-specific promoters. The promoter can be a non-viral promoter or a viral promoter. Preferably, it is a heterologous promotor, i.e., a promotor not naturally linked to TCR in human T cells, such as long terminal repeat promotor, which is suitable for expression in human T cells. The inventive recombinant expression vectors can be designed for either transient

TABLE 3

CDR1, CDR2 and CDR3 of TCR constructs of the invention
Complementarity Determining Regions

|  | CDR1 | CDR2 | CDR3 |
| --- | --- | --- | --- |
| TCR3598, alpha chain | 49-54 of SEQ ID NO 22 | 72-76 of SEQ ID NO 22 | 111-123 of SEQ ID NO 22 |
| TCR3598_2, alpha chain | 46-51 of SEQ ID NO 23 | 69-74 of SEQ ID NO 23 | 109-123 of SEQ ID NO 23 |
| TCR5412, alpha chain | 46-51 of SEQ ID NO 24 | 69-75 of SEQ ID NO 24 | 110-122 of SEQ ID NO 24 |
| TCR5412_2, alpha chain | 46-51 of SEQ ID NO 25 | 69-75 of SEQ ID NO 25 | 110-123 of SEQ ID NO 25 |
| TCR5412_3, alpha chain | 45-49 of SEQ ID NO 26 | 67-72 of SEQ ID NO 26 | 107-122 of SEQ ID NO 26 |
| TCR3600, alpha chain | 49-53 of SEQ ID NO 27 | 71-74 of SEQ ID NO 27 | 109-121 of SEQ ID NO 27 |
| TCR5712, alpha chain | 49-53 of SEQ ID NO 28 | 71-74 of SEQ ID NO 28 | 109-121 of SEQ ID NO 28 |
| TCR5415, alpha chain | 49-53 of SEQ ID NO 29 | 71-74 of SEQ ID NO 29 | 109-121 of SEQ ID NO 29 |
| TCR5713, alpha chain | 47-52 of SEQ ID NO 30 | 70-75 of SEQ ID NO 30 | 110-122 of SEQ ID NO 30 |
| TCR3598, beta chain | 46-50 of SEQ ID NO 58 | 68-73 of SEQ ID NO 58 | 111-123 of SEQ ID NO 58 |
| TCR3598_2, beta chain | 46-50 of SEQ ID NO 59 | 68-73 of SEQ ID NO 59 | 111-125 of SEQ ID NO 59 |
| TCR5412, beta chain | 46-50 of SEQ ID NO 60 | 68-73 of SEQ ID NO 60 | 111-124 of SEQ ID NO 60 |
| TCR5412_2, beta chain | 46-50 of SEQ ID NO 61 | 68-73 of SEQ ID NO 61 | 111-125 of SEQ ID NO 61 |
| TCR5412_3, beta chain | 46-50 of SEQ ID NO 62 | 68-73 of SEQ ID NO 62 | 111-122 of SEQ ID NO 62 |
| TCR3600, beta chain | 46-50 of SEQ ID NO 63 | 68-73 of SEQ ID NO 63 | 111-121 of SEQ ID NO 63 |
| TCR5712, beta chain | 46-50 of SEQ ID NO 64 | 68-73 of SEQ ID NO 64 | 111-121 of SEQ ID NO 64 |
| TCR5415, beta chain | 46-50 of SEQ ID NO 65 | 68-73 of SEQ ID NO 65 | 111-121 of SEQ ID NO 65 |
| TCR5713, beta chain | 46-50 of SEQ ID NO 66 | 68-73 of SEQ ID NO 66 | 111-126 of SEQ ID NO 66 |
| TCR-ESO, alpha chain | 48-52 of SEQ ID NO 104 | 70-75 of SEQ ID NO 104 | 110-122 of SEQ ID NO 104 |
| TCR-ESO, beta chain | 46-50 of SEQ ID NO 108 | 68-73 of SEQ ID NO 108 | 111-124 of SEQ ID NO 108 | expression, for stable expression, or for both. Also, the recombinant expression vectors can be made for constitutive expression or for inducible expression.

The present invention also provides a protein, i.e., an alpha or beta chain construct, or, preferably, a TCR receptor construct comprising both alpha and beta chain constructs, which is capable of specifically binding HLA-DR4 in combination with the epitope NY-ESO-1$_{116-135}$, or HLA-A2 in combination with the epitope NY-ESO-1$_{157-165}$. The protein is preferably encoded by the nucleic acids of the invention.

The term "capable of specifically binding" or "recognizing" or "specific for" a given antigen, as used herein, means that the TCR construct can specifically bind to and immunologically recognize said epitope, preferably NY-ESO-1, more preferably with high affinity. For example, a TCR may be considered to have "be able of specifically binding" to NY-ESO-1 if T cells expressing the TCR secrete at least about 200 pg/ml or more (e.g. 250 pg/ml or more, 300 pg/ml or more, 400 pg/ml or more, 500 pg/ml or more, 600 pg/ml or more, 700 pg/ml or more, 1000 pg ml or more, 2,000 pg/ml or more, 2,500 pg/ml or more, 5,000 pg/ml or more) of interferon γ (IFN-γ) upon co-culture with target cells pulsed with a low concentration of the respective epitope, e.g., NY-ESO-1 epitope, such as the HLA-A2 restricted NY-ESO1$_{157-165}$ epitope or the HLA-DR4-restricted NY-ESO-1$_{116-135}$ epitope (e.g., about $10^{-11}$ mol/l, $10^{-10}$ mol/l, $10^{-9}$ mol/l, $10^{-8}$ mol/l, $10^{-7}$ mol/l, $10^{-6}$ mol/l, $10^{-5}$ mol/l), but not without epitope or with a control peptide epitope. Alternatively or additionally, a TCR may be considered to have "antigenic specificity" for a NY-ESO-1 epitope if T cells expressing the TCR secrete at least twice as much IFN-γ as the untransduced background level of IFN-γ upon co-culture with target cells pulsed with a low concentration of the appropriate peptide. Such "specificity" as described above can—for example—be analyzed with an ELISA.

Affinity can be analyzed by methods well known to the skilled person, e.g. by BiaCore. An TCR affinity or T cell avidity of 100 μM or higher, more preferably 10 μM or higher is considered high affinity.

Based on the defined CDR3 and variable region sequences provided by the invention, it is possible to carry out affinity maturation of the TCR sequences (Chervin et al. J Immunol Methods. 2008; 339(2):175-84); Robbins et al. J Immunol. 2008; 180:6116-31). Non-synonymous nucleotide substitutions, which lead to amino acid exchanges in the CDR3 sequence, may lead to enhanced affinity of the TCR to target antigen. Furthermore, TCR sequence changes in other parts of the variable TRA and TRB regions may change affinity of the TCR to the peptide-MHC complex. This may increase overall affinity of the TCR to the peptide-MHC, but harbors the risk of unspecific recognition and increased cross-reactivity (Linette et al. Blood. 2013; 122 (6):863-72). It is preferred that TCRs varying from the specific sequences provided retain exclusive specificity for the target antigen provided, i.e., that they are not cross-reactive, most importantly, that they do not have cross-reactivity for human self-peptides. Potential cross-reactivity of TCR can be tested against known self-peptides loaded on cells with the correct MHC allele (Morgan et al., 2013, J. Immunother. 36, 133-151). Accordingly, it is preferred that adoptive transfer of T cells expressing the TCR construct of the invention has no or significant negative effects on healthy tissue.

A TCR alpha and/or beta chain construct of the invention may comprise all characteristics or domains corresponding to its native counterpart, but this is not essential. Preferably, the TCR alpha and/or beta chain construct comprises at least a variable region, or a variable and a constant region, e.g., the variable and/or constant region having at least 60%, at least 70%, at least 80%, at least 90% or at least 95% sequence identity to a human variable or constant TCR region. For adoptive TCR therapy, it is preferred that the TCR construct comprises full length TCR alpha and beta chains comprising variable, constant and transmembrane regions. The TCR construct preferably is of essentially or exclusively human origin to minimize immunogenicity. To prevent pairing with endogenous TCR chains, the constructs of the invention however preferably contain one or more, e.g., 1-5, 1-10 or 1-20, amino acid exchanges, insertions or deletions in comparison to a human sequence, e.g., providing an additional cysteine to enable formation of an additional disulfide bond (Sommer-meyer et al., 2010, J. Immunol. 184, 6223-31). To this end, the constant region of the TCR alpha and beta chain construct may also be a murine constant region.

The construct may also be a chimeric antigen receptor, or part of it, wherein, e.g. a human TCR variable region may be linked to a different immunoglobulin constant domain, e.g. an IgG constant domain, or to an antibody domain capable of specifically binding to an antigen such as NY-ESO-1.

Single chain constructs (scTCR) are encompassed as well as heterodimeric TCR constructs. A scTCR can comprise a variable region of a first TCR chain construct (e.g., an alpha chain) and an entire (full-length) second TCR chain (e.g., a beta chain), or vice versa. Furthermore, the scTCR can optionally comprise one or more linkers which join the two or more polypeptides together. The linker can be, for instance, a peptide which joins together two single chains, as described herein. Also provided is such a scTCR of the invention, which is fused to a cytokine, e.g., a human cytokine, such as IL-2, IL-7 or IL-15.

The TCR construct according to the invention can also be provided in the form of a multimeric complex, comprising at least two scTCR molecules, wherein said scTCR molecules are each fused to at least one biotin moiety, and wherein said scTCRs are interconnected by biotin-strepavidin interaction to allow the formation of said multimeric complex. Also provided are multimeric complexes of a higher order, comprising more than two, e.g., four, scTCR of the invention.

The TCR construct of the invention can be modified to comprise a detectable label, such as, for instance, a radioisotope, a fluorophore (e.g., fluorescein isothiocyanate (MC), phycoerythrin (PE)), an enzyme (e.g., alkaline phosphatase, horseradish peroxidase), and particles (e.g., gold particles or magnetic particles).

The invention also provides a host cell comprising a nucleic acid or protein of the invention. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. For purposes of producing a recombinant TCR, polypeptide, or protein, the host cell is preferably a mammalian cell. Most preferably, the host cell is a human cell. While the host cell can be of any cell type, can originate from any type of tissue, and can be of any developmental stage, the host cell preferably is a peripheral blood leukocyte (PBL) or a peripheral blood mononuclear cell (PBMC). More preferably, the host cell is a T cell or T cell precursor, in particular, a human T cell. The T cell can be any T cell, such as a cultured T cell, e.g. a primary T cell, or a T cell from a cultured T cell line, e.g. Jurkat, SupT1, etc., or a T cell obtained from a mammal, preferably, it is a T cell or T cell precursor from a human patient. The T cell can be obtained from numerous sources, such as blood, bone marrow, lymph node, the thymus, or other tissues or fluids. T cells can also be enriched for or purified. Preferably, the T cell is a human T cell. More preferably, the T cell is a T cell isolated from a human, e.g., a human patient. The T cell can be any type of T cell and can be of any developmental stage, including but not limited to, CD4+ and/or CD8+, CD4+ helper T cells, e.g., Th1 and Th2 cells, CD8+ T cells (e.g., cytotoxic T cells), tumor infiltrating cells (TILs), effector cells, central effector cells, memory T cells, naive T cells, and the like, preferably central-memory T cells.

Preferably, the host cell is a human CD4-positive T cell, wherein the TCR construct of the invention is restricted to the MHC II epitope, or a human CD8-positive T cell, wherein the TCR construct of the invention is restricted to the MHC I epitope.

The invention also provides a pharmaceutical composition comprising
a) a nucleic acid, preferably, an expression vector suitable for expression in a human T cell, encoding the TCR construct of the invention, which is capable of specifically binding to an epitope from NY-ESO-1 in complex with a human MHC, or
b) a protein comprising a TCR construct of the invention, which is capable of specifically binding to an epitope from NY-ESO-1 in complex with a human MHC, or
c) a host cell, e.g., a human T cell, of the invention, expressing a TCR construct capable of specifically binding to an epitope from NY-ESO-1 in complex with a human MHC.

In a preferred embodiment, the TCR construct of the invention employed in the pharmaceutical composition is the TCR construct capable of recognizing the epitope restricted to HLA-DR4, as disclosed herein.

Alternatively, the TCR construct is the TCR construct of the invention capable of recognizing the epitope restricted to HLA-A02, as disclosed herein.

The invention also provides a kit, preferably, for use in medicine, in particular, for treatment of a human patient, comprising, as a first component
a) a nucleic acid, preferably, an expression vector, encoding a TCR construct capable of specifically binding to an epitope from a defined antigen in complex with a human MHC II, or
b) a protein comprising a TCR construct capable of specifically binding to an epitope from a defined antigen in complex with a human MHC II, or
c) a host cell expressing a TCR construct capable of specifically binding to an epitope from a defined antigen in complex with a human MHC II,
and
i) a nucleic acid, preferably, an expression vector, encoding a TCR construct capable of specifically binding to an epitope from said defined antigen in complex with a human MHC I, or
ii) a protein comprising a TCR construct capable of specifically binding to an epitope from said defined antigen in complex with a human MHC I, or
iii) a host cell expressing a TCR construct capable of specifically binding to an epitope from said defined antigen in complex with a human MHC I.

Said defined antigen preferably is a tumor-associated or tumor-specific antigen selected from the group comprising cancer-testis-antigens such as NY-ESO-1. In particular, the epitopes are the epitopes of SEQ ID NO: 21 (HLA-DR4-restricted) and 103 (HLA-A02-restricted), respectively. Alternatively, the antigen may be a somatic mutated antigen, viral antigen, tumor driving antigen, tumor-associated antigen, differentiation antigen e.g. cancer-testis antigens. Preferably, the TCR construct is a human TCR, an essentially human TCR, as disclosed above, or derived from a human TCR, e.g., derived from a humanized mouse as described below.

So far, adoptive T cell transfer to humans has exclusively focused on administration of either CD8+ or CD4+ T cells. However, the inventors have provided the means to carry out an adoptive T cell therapy in humans comprising transfer of both CD8+ and CD4+ T cells with a TCR construct specific for a defined tumor associated antigen, NY-ESO-1, which allows for cooperation of the two cell types. Alternatively, nucleic acids encoding said TCR construct or respective proteins can also be employed to transfer the required specificities to endogenous T cells of the patient. CD4+ cells, e.g., by secretion of cytokines such as IFN-gamma and IL-2 may promote CD8+ cell recruitment to the tumor and cytolytic function. This enables more efficient elimination of tumor cells, and regression or, preferably, elimination of the tumor. Preferably, there is no relapse.

In particular, the invention provides a kit as described above, comprising the pharmaceutical composition comprising, as a first component,
a) a nucleic acid, preferably, an expression vector suitable for expression in a human T cell, encoding the TCR construct of the invention, which is capable of specifically binding to the epitope from NY-ESO-1 in complex with human HLA-DR4, and which comprises a CDR3 region having, preferably, at least 80% sequence identity to any of SEQ ID NO: 1-18,
b) a protein comprising a TCR construct of the invention, which is capable of specifically binding to the epitope from NY-ESO-1 in complex with human HLA-DR4, and which comprises a CDR3 region having, preferably, at least 80% sequence identity to any of SEQ ID NO: 1-18, or
c) a host cell, e.g., a human T cell, of the invention, expressing a TCR construct capable of specifically binding to the epitope from NY-ESO-1 in complex with HLA-DR4, and which comprises a CDR3 region having, preferably, at least 80% sequence identity to any of SEQ ID NO: 1-18.

Said kit preferably, as a second component, comprises a pharmaceutical composition, comprising
i) a nucleic acid, preferably, an expression vector, encoding a TCR construct capable of specifically binding to an epitope from said defined antigen in complex with a human MHC I, e.g., a TCR construct of the invention which comprises CDR3 regions having, preferably, at least 80% sequence identity to SEQ ID NO: 19-20, or
ii) a protein comprising a TCR construct capable of specifically binding to an epitope from said defined antigen in complex with a human MHC I, e.g., a TCR construct of the invention which comprises CDR3 regions having, preferably, at least 80% sequence identity to SEQ ID NO: 19-20, or
iii) a host cell expressing a TCR construct capable of specifically binding to an epitope from said defined antigen in complex with a human MHC I, e.g., a TCR construct of the invention which comprises CDR3 regions having, preferably, at least 80% sequence identity to SEQ ID NO: 19-20.

The components of a kit of the invention may be formulated for simultaneous administration or for administration in any sequence. The components may also be for repeated administration. Tran et al. (Science, 2014 May 9; 344(6184): 641-5) describe a possible regimen of administration.

Examples of pharmaceutically acceptable carriers or diluents useful in the present invention include stabilizers such as SPGA, carbohydrates (e.g. sorbitol, mannitol, starch, sucrose, glucose, dextran), proteins such as albumin or casein, protein containing agents such as bovine serum or skimmed milk and buffers (e.g. phosphate buffer such as phosphate buffered saline).

The pharmaceutical composition of the invention or the kit of the invention may be for use in the diagnosis, prevention and/or treatment of a disease, e.g. a proliferative, infective or viral disease. The disease preferably is tumor disease, e.g. a benign or malignant tumor disease. In a preferred embodiment, the proliferating cells or the tumor express NY-ESO-1, and the TCR construct is capable of recognizing at least one epitope from NY-ESO-1. Preferably, the disease is treated. Reduction of the risk of getting a disease is also considered prevention of a disease, preferably, the risk of the treated subject is reduced below the normal level in a comparative population, preferably, the risk is reduced by at least 10%, at least 25%, at least 50% or at least 75%, or 100%.

The present invention also provides a method for treating a subject suffering from a disease as specified above, in particular, a tumor or tumor disease comprising administering a nucleic acid, protein or host cell of the invention. Preferably the subject is a subject in need of such a treatment, i.e. a patient. The subject in preferred embodiments is a mammalian subject, preferably a human patient, suffering from a tumor or tumor disease. The active agent is administered in an effective amount.

The term "tumor" or "tumor disease" in the context of the present invention denotes a disease selected from melanoma, hepatocellular carcinoma, intra- and extrahepatic cholangiocellular carcinoma, squamous cell carcinoma, adenocarcinoma as well as undifferentiated carcinoma of the head, neck, lung or esophagus, colorectal carcinoma, chondrosarcoma, osteosarcoma, medulloblastoma, neuroblastoma, non-squamous cell carcinoma of the head or neck, ovarian tumor, lymphoma, acute and chronic lymphocytic leukemia, acute and chronic myeloid leukemia, bladder carcinoma, prostate carcinoma, pancreatic adenocarcinoma, mammary carcinoma and gastric carcinoma. The tumor expressing NY-ESO-1 is preferably selected from melanoma, lung carcinoma, synovial sarcoma, and cancer of the head and neck, oesophagus and bladder.

One preferred medicinal use of the invention relates to immune therapy, preferably adoptive T cell therapy. The product and methods of the invention are particularly useful in the context of adoptive T cell therapy. The administration of the compounds of the invention can for example involve the administration, e.g., infusion of T cells of the invention into said patient. Preferably such T cells are autologous T cells of the patient which were in vitro transduced with a nucleic acid of the present invention.

Alternatively, the patient may also be administered a nucleic acid of the invention, in particularly, an expression vector, for in vivo transduction of T cells.

Protein TCR constructs of the invention may also, e.g., be used for diagnostic purposes to find out if a subject expresses NY-ESO-1, and, in particular, if the epitope according to SEQ ID NO: 21 is. To this end, such constructs are preferably labelled to facilitate detection. Preferably, a patient presenting said epitope on HLA-DR4 is treated by an adoptive T cell therapy of the invention.

The invention also relates to a method of preparing a host cell of the invention, comprising introducing an expression vector encoding a TCR construct capable of specifically binding to an epitope from NY-ESO-1 in complex with a human MHC into a suitable host cell, preferably, a human T cell isolated from a patient.

The present invention is further illustrated in the following examples with reference to the accompanying figures and sequences, nevertheless, without being limited thereto. For the purposes of the present invention, all references as cited herein are incorporated by reference in their entirety.

FIG. 1 Functional comparison of the NY-E50157-specific TCR-ESO from ABabDII mice with a patient-derived TCR 1G4. (a) PBMCs from a human donor were transduced with the ABabDII-derived TCR-ESO or the human-derived TCR 1G4 and stained with a NY-ES0157-HLA-A2-specific multimer. Gated on CD3+ cells. (b) T2 cells were pulsed with increasing amounts of NY-ESO157 native peptide and co-cultured with TCR-transduced T cells. (c) IFNγ production by TCR-transduced T cells after co-culture with different tumor cell lines (SK.Mel37: HLA-A2+/NY-ESO+, SK.Mel29.MiG: HLA-A2+/NY-ESO−, SK.Mel29.MiG.NY-ESO: HLA-A2+/NY-ESO+, Mel324: HLA-A2+/NY-ESO−, Mel295: HLA-A2+/NY-ESO+). Graphs in b and c represent averages of intra-assay duplicates ±s.d.

Figure 2:
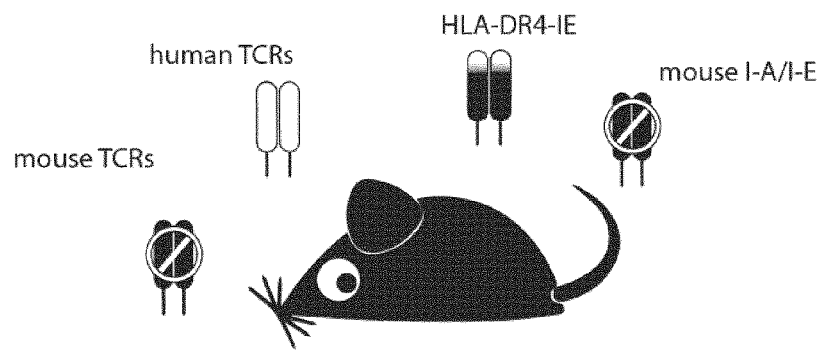

FIG. 2 ABabDR4 mice are transgenic for the entire TCRαβ gene loci and for the human MHC class II molecule HLA-DR4 fused to the non-antigen-binding domains of mouse I-E. ABabDR4 mice are deficient for mouse TCRs and mouse MHC class II molecules. Hence, AbabDR4 express a diverse human TCR repertoire with CD4 T cells having HLA-DR4 restriction.

Figure 3:
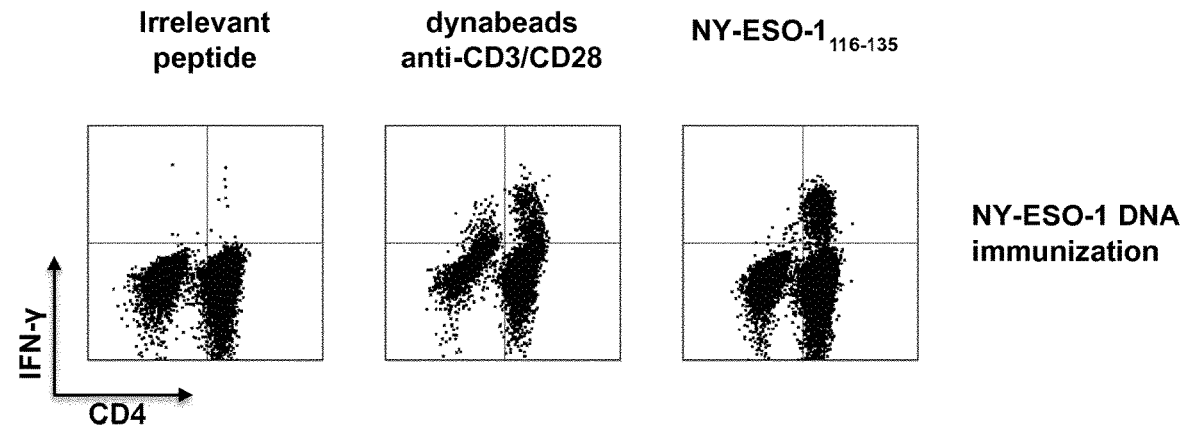

FIG. 3 Peripheral blood leucocytes from an ABabDR4 mouse immunized with NY-ESO-1 DNA were restimulated overnight with anti-CD3/CD28 dynabeads, irrelevant peptide, or NY-ES0$_{116-135}$ and stained intracellularly for IFNγ. Plotted cells were gated on lymphocytes and CD3 positive cells.

FIG. 4 Schematic structure of retroviral TCR-vector MP71 (Linnemann et al., 2013, Nature Medicine 19, 1534-1541)

Figure 5:
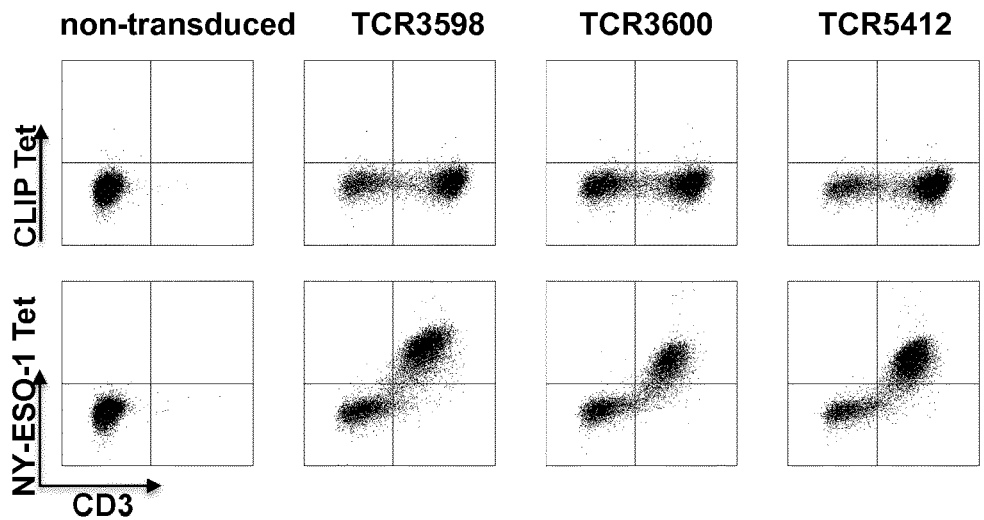

FIG. 5 TCR-deficient and CD4-expressing Jurkat cells were transduced with NY-ESO-1-reactive TCRs and stained by $_{NY\text{-}ESO\text{-}}1_{116-135}$/DR4-Tetramer (NY-ESO-1 Tet) or CLIP/DR4-Tetramer (CLIP Tet) as control.

Figure 6:
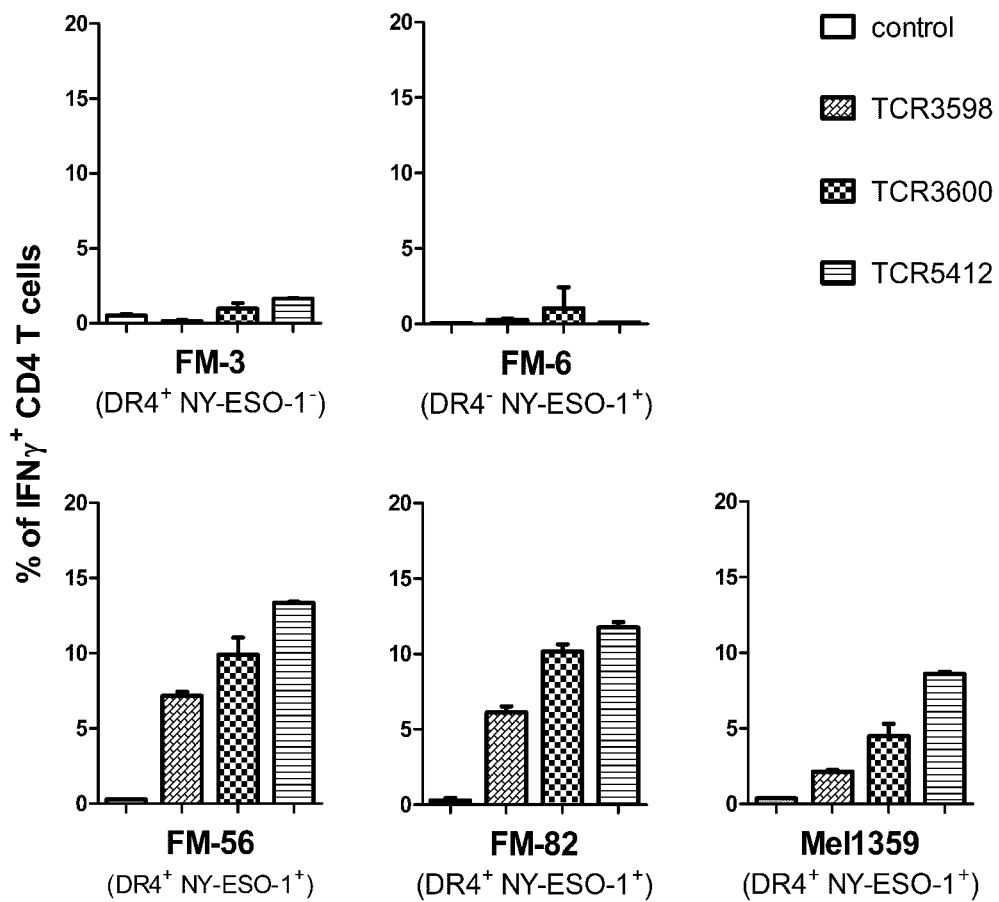

FIG. 6 TCR-transduced or non-transduced (control) CD4+ T cells from human PBMC were co-cultured with different melanoma cell lines naturally expressing HLA-DR4 and/or NY-ESO-1 and were stained intracellularly for IFNγ. Displayed percentages refer to transduced CD4+ T cells (TCR-transduced samples) or total CD4+ T cells (non-transduced samples). Mean values of duplicates with standard deviation are shown. All melanoma cell lines were analysed for HLA-DR expression by flow cytometry.

Figure 7:
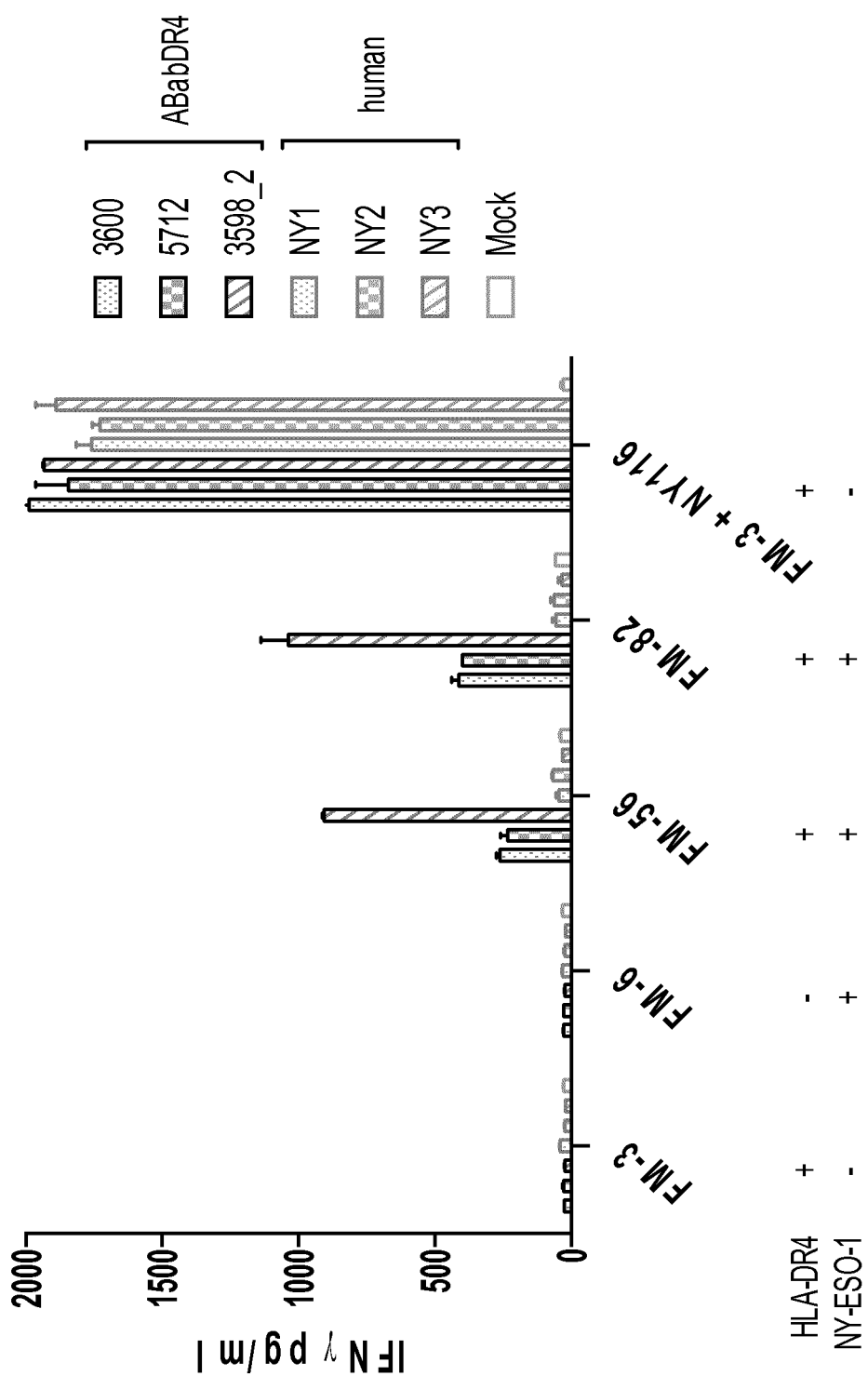

FIG. 7 ABabDR4 mice-derived but not human-derived NY-ESO-1$_{116-135}$-reactive TCRs recognize HLA-DR4/NY-ESO-1 expressing melanoma lines. CD4 T cells transduced with NY-ESO-1$_{116-135}$-reactive TCRs derived from ABabDR4 mice (3600, 5712, 3598_2) or from a healthy human donor (NY1, NY2, NY3) were co-cultured with IFNγ-pretreated melanoma lines expressing HLA-DR4 and/or NY-ESO-1. $_{NY\text{-}ESO\text{-}}1_{116-135}$ peptide (NY116) was added as a positive control. After overnight incubation IFNγ was measured in the supernatant. Mean values of intra-assay duplicates with standard deviation are shown. All melanoma lines were analysed for HLA-DR expression by flow cytometry.

Figure 8:
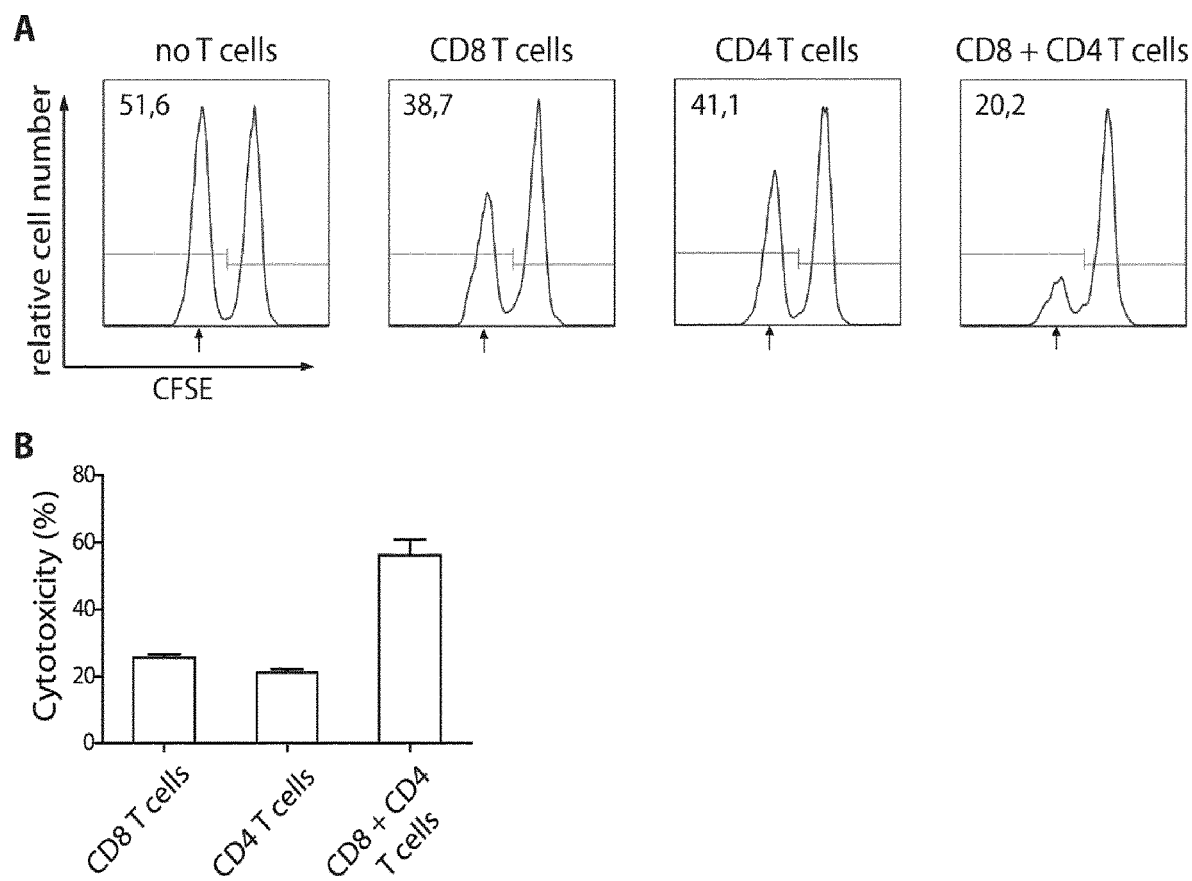

FIG. 8 CD8 and CD4 T cells transduced with NY-ESO-1-reactive TCRs show cooperative effect in tumor cell killing. TCR-ESO-transduced CD8 T cells and/or TCR3598_2-transduced CD4 T cells were cultured with CFSE-labelled melanoma line FM-3 loaded (low CFSE fluorescence) and not loaded (high CFSE fluorescence) with NY-ESO-$1_{116-135}$ and NY-ESO-$1_{157-165}$ peptides. CFSE-labelled target and control cells were cultured in a 1:1 ratio, $8 \times 10^4$ cells each. TCR-transduced CD8 and CD4 T cell numbers were $6 \times 10^4$ each. After overnight incubation cell numbers of FM-3 were measured by flow cytometry. (A) Representative histograms of FM-3 cells after incubation with TCR-transduced T cells are shown. Numbers indicate percentage of the NY-ESO-1 peptides-loaded FM-3 cells (small arrows). (B) Bar diagram indicates cytotoxicity of TCR-transduced CD4 and/or CD8 T cells determined by killing of target cells as shown in A. Mean values of intra-assay duplicates with standard deviation are shown.

EXAMPLES

Example 1

Generation of HLA-A02-Restricted Human TCR Specific for NY-ESO-$1_{157-165}$ in ABabDII Mice ABabDII mice were generated as described in Li et al. (2010, Nature Medicine 16, 1029-1034). Bulk CD8+ populations specific for NY-ESO-$1_{157-165}$ were isolated from vaccinated mice and analyzed by TCR gene capture, following the protocol disclosed in Linnemann et al. (2013, Nature Medicine 19, 1534-1541).

TCR-ESO, as shown, e.g., in Table 2, and characterized by the CDR3 sequences according to SEQ ID NO:18 and 19 was generated.

Optimized sequences for the full length constructs are provided in SEQ ID NO: 106/107 and SEQ ID NO: 110/111. SEQ ID NO: 112 corresponds to a single chain nucleic acid construct used in the following.

Example 2

Functional Analysis of the HLA-A02-Restricted Human TCR

The NY-ESO$_{157-165}$-specific TCR-ESO from ABabDII mice, as generated in Example 1, was compared with the melanoma patient-derived TCR 1G4 (Chen, et al., 2005, J. Exp. Med. 201, 1243-55). Both TCRs recognize epitope 157-165 (SEQ ID NO: 103). The TCRs were expressed in human T cells from PBMC of a human donor (FIG. 1a). T cells transduced with the ABabDII-derived TCR-ESO demonstrated increased antigen sensitivity and induced higher maximal IFNγ levels upon recognition of peptide-loaded T2 cells than T cells transduced with the human-derived TCR 1G4 (FIG. 1b). In addition, TCR-ESO-transduced human T cells produced more IFNγ after co-culture with NY-ESO expressing HLA-A2$^+$ cancer cells than 1G4-transduced T cells (FIG. 1c).

The TCR obtained from the ABabDII mouse surprisingly showed superior functional activity compared to the TCR isolated from the human donor.

Example 3

Generation of HLA-DR4-Restricted, Human TCRs Specific for NY-ESO-$1_{116-135}$ in ABabDR4 Mice HLA-DR4-restricted TCRs against NY-ESO-1 were raised in human TCR gene loci/HLA-DRA-IE/HLA-DRB1*0401-IE transgenic (ABabDR4) mice (FIG. 2). These mice were generated by crossing HLA-DRA-IE/HLA-DRB1*0401-IE transgenic mice (Ito et al., 1996, J Exp Med 183(6): 2635-2644) with human TCR gene loci transgenic mice (Li et al., 2010, Nat. Medicine 16(9):1029-1034). The advantage of this model is that T cells in ABabDR4 mice express a diverse human TCR repertoire but were not subject to tolerance mechanisms to human tumor antigens in regions in which human and mouse sequences differ from each other. The inventors found that immunizing ABabDR4 mice with NY-ESO-1 results in the generation of high affinity TCRs that cannot be found in humans. Due to HLA-DR4-IE as exclusive MHC class II restriction molecule, immunizing ABabDR4 mice generates CD4+ T cells that recognize the immunized antigen with HLA-DR4 restriction.

TCRs specific for the NY-ESO-$1_{116-135}$ peptide in combination with HLA-DR4 were generated from ABabDR4 mice following vaccination with NY-ESO-$1_{116-135}$ peptide or full length NY-ESO-1 DNA. Bulk CD4+ populations specific for NY-ESO-$1_{116-135}$ were isolated and the TCR chains were extracted by 5' rapid amplification of cDNA ends. FIG. 3 shows specific activity of peripheral blood leucocytes from ABabDR4 mice restimulated overnight with anti-CD3/CD28 dynabeads, irrelevant peptide, or NY-ESO$_{116-135}$, as proven by production of IFNγ.

TCRs characterized by the CDR3 sequences according to SEQ ID NO:1 and 10, 2 and 11, 3 and 12, 4 and 13, 5 and 14, 6 and 15, 7 and 16, 8 and 17 and 9 and 18 were generated, e.g., as shown in Table 1. The invention thus provides the first HLA-DR4 restricted human TCRs for NY-ESO-1.

Optimized sequences for the full length constructs are provided in SEQ ID NO: 40-48/49-57 and SEQ ID NO: 76-84/85-93. SEQ ID NO: 94-102 correspond to single chain nucleic acid constructs used in the following experiments.

Example 4

Functional Analysis of the HLA-DR4-Restricted, Human TCRs

To demonstrate that the isolated TCRs conferred specific binding to the relevant peptide/MHC complex, TCR-deficient and CD4-expressing Jurkat cells were transduced with NY-ESO-1-reactive TCRs as prepared in Example 3, and stained by NY-ESO-$1_{116-135}$/DR4-Tetramer (NY-ESO-1 Tet) or CLIP/DR4-Tetramer (CLIP Tet) as control (Data shown for TCR3598, TCR3600 and TCR5412 in FIG. 5). The specificity was confirmed.

The isolated TCRs also conferred functional activity against NY-ESO-1 expressing cells. This is shown by TCR-transduced or non-transduced (control) CD4+ T cells from human PBMC co-cultured with different melanoma cell lines naturally expressing HLA-DR4 and/or NY-ESO-1 and intracellular staining for IFNγ (Data shown for TCR3598, TCR3600 and TCR5412 in FIG. 6).

Transfer of TCR5412 led to a higher proportion of IFN-gamma CD4+ cells. Accordingly, TCR constructs comprising the CDR3 sequences of SEQ ID NO:3 and 12 are especially preferred in the context of the invention.

Example 5

Adoptive T Cell Transfer of a Combination of CD4+ and CD8+ T Cells Specific for NY-ESO-1 Epitopes The combined use of MHC I and MHC II restricted TCRs specific for NY-ESO-1 is tested in a mouse model of adoptive T cell therapy of cancer. An NY-ESO-1 and HLA-A2 positive tumor cell line is transplanted in HLA-DR4-IExRag-/- mice and treated with either murine CD8 T cells transduced with an MHC I-restricted TCR or murine CD4 T cells transduced with an MHC II-restricted TCR or a mixture of both. Recipient mice are monitored over time for tumor rejection and relapse. For treatment with both MHC I and MHC II-restricted TCRs no relapse is expected.

The invention claimed is:

1. A nucleic acid encoding at least one T cell receptor (TCR) alpha chain construct and/or TCR beta chain construct of a TCR construct capable of specifically binding to an epitope from NY-ESO-1 in complex with a human MEW, wherein the TCR alpha chain construct and/or the TCR beta chain construct comprises a complementarity determining region 3 (CDR3) as set forth in SEQ ID NO: 1 or having at least 90% sequence identity to an amino acid selected from SEQ ID NOs: 2 and 4-19 .

2. The nucleic acid of claim 1, wherein the TCR construct is capable of specifically binding to the epitope consisting of SEQ ID:21 in complex with HLA-DR4, wherein the TCR alpha chain construct comprises a CDR3 as set forth in SEQ ID NO: 1 or having at least 90% sequence identity to an amino acid selected from SEQ ID NOs: 2 and 4-9 and/or the TCR beta chain construct comprises a complementarity determining region 3 (CDR3) having at least 90% sequence identity to an amino acid selected from SEQ ID NOs: 10-18.

3. The nucleic acid of claim 2,
a) wherein the TCR alpha chain construct comprises a variable region comprising a sequence having at least 80% sequence identity to SEQ ID NOs: 22-30, which is optionally encoded by a sequence selected from SEQ ID NOs: 31-39, wherein the TCR alpha chain construct preferably comprises a sequence having at least 80% sequence identity to any of SEQ ID NOs: 40-48 and is optionally encoded by any of SEQ ID NOs: 49-57, b) and/or wherein the TCR beta chain construct comprises a variable region comprising a sequence having at least 80% sequence identity to SEQ ID NOs: 58-66, which is optionally encoded by a sequence selected from SEQ ID NOs: 67-75, wherein the TCR beta chain construct preferably comprises a sequence having at least 80% sequence identity to any of SEQ ID NOs: 76-84 and is optionally encoded by any of SEQ ID NOs: 85-93, c) wherein the TCR construct is preferably encoded by any of SEQ ID NOs: 94-102;

d) wherein the TCR alpha chain construct and/or TCR/beta chain construct or TCR construct preferably is an expression vector suitable for expression is a host cell selected from the group comprising a human T cell.

4. The nucleic acid of claim 1, wherein the TCR construct is capable of specifically binding to the epitope consisting of SEQ ID:103 in complex with HLA-A2, wherein the TCR alpha chain construct comprises a complementarity determining region 3 (CDR3) having at least 90% sequence identity to SEQ ID NO: 19 and the TCR beta chain construct comprises a complementarity determining region 3 (CDR3) having at least 90% sequence identity to SEQ ID NO: 20.

5. The nucleic acid of claim 4, a) wherein the TCR alpha chain construct comprises a variable region comprising a sequence having at least 80% sequence identity to SEQ ID NO: 104, which is optionally encoded by SEQ ID NO: 105, wherein the TCR alpha chain construct preferably comprises a sequence having at least 80% sequence identity to SEQ ID NO: 106 and is optionally encoded by SEQ ID NO: 107, b) and/or wherein the TCR beta chain construct comprises a variable region comprising a sequence having at least 80% sequence identity to SEQ ID NO: 108, which is optionally encoded by SEQ ID NO: 109, wherein the TCR beta chain construct preferably comprises a sequence having at least 80% sequence identity to SEQ ID NO: 110 and is optionally encoded by SEQ ID NO: 111, c) wherein the TCR construct is preferably encoded by SEQ ID NO: 112, d) wherein the TCR alpha chain construct and/or TCR/beta chain construct or TCR construct preferably is an expression vector suitable for expression is a host cell selected from the group comprising a human T cell.

6. A protein encoded by the nucleic acid of claim 1.

7. A host cell comprising a nucleic acid of claim 1, wherein the TCR construct is capable of specifically binding to the epitope consisting of SEQ ID NO::21 in complex with HLA-DR4, wherein the TCR alpha chain construct comprises a CDR3 as set forth in SEQ ID NO: 1 or having at least 90% sequence identity to an amino acid selected from SEQ ID NOs: 2 and 4-9 and/or the TCR beta chain construct comprises a complementarity determining region 3 (CDR3) having at least 90% sequence identity to an amino acid selected from SEQ ID NOs: 10-18, and wherein the host cell preferably is a CD4+T cell.

8. A pharmaceutical composition comprising a) a nucleic acid of claim 1 encoding a TCR construct capable of specifically binding to an epitope from NY-ESO-1 in complex with a human MHC.

9. The pharmaceutical composition of claim 8, comprising a nucleic acid wherein the TCR construct is capable of specifically binding to the epitope consisting of SEQ ID:21 in complex with HLA-DR4, wherein the TCR alpha chain construct comprises a CDR3 as set forth in SEQ ID NO: 1 or having at least 90% sequence identity, preferably, 100% sequence identity, to an amino acid selected from SEQ ID NO: 2-9 and/or the TCR beta chain construct comprises a complementarity determining region 3 (CDR3) having at least 90% sequence identity, preferably, 100% sequence identity, to an amino acid selected from SEQ ID NO: 10-18, a protein encoded by said nucleic acid, or a host cell comprising said nucleic acid.

10. The pharmaceutical composition of claim 8, comprising a nucleic acid wherein the TCR construct is capable of specifically binding to the epitope consisting of SEQ ID:103 in complex with HLA-A2, wherein the TCR alpha chain construct comprises a complementarity determining region 3 (CDR3) having at least 90% sequence identity, preferably, 100% sequence identity, to SEQ ID NO: 19 and/or the TCR beta chain construct comprises a complementarity determining region 3 (CDR3) having at least 90% sequence identity, preferably, 100% sequence identity, to SEQ ID NO: 20, a protein encoded by said nucleic acid, or a host cell comprising said nucleic acid.

11. A kit for use in medicine, comprising, as a first component a) a nucleic acid encoding a TCR alpha chain construct and/or TCR beta chain construct capable of specifically binding to an epitope from a NY-ESO-1 in complex with a human MHC II wherein the TCR alpha chain construct and/or the TCR beta chain construct comprises a complementarity determining region 3 (CDR3) as set forth in SEQ ID NO: 1 or having at least 90% sequence identity to an amino acid selected from SEQ ID NOs: 2 and 4-19; or b) a protein encoded by said nucleic acid of part a comprising a TCR construct capable of specifically binding to NY-ESO-1 in complex with a human MHC II; or c) a host cell comprising the nucleic acid of part a, and/or i) a nucleic acid encoding at least one T cell receptor (TCR) alpha chain construct and/or TCR beta chain construct of a TCR construct capable of specifically binding to an epitope from NY-ESO-1 in complex with a human MHC I, wherein the TCR alpha chain construct comprises a complementarity determining region 3 (CDR3) having at least 90% sequence identity to an amino acid as set forth in SEQ ID NO: 3 and wherein the TCR alpha chain construct comprises a variable region comprising a sequence having at least 80% sequence identity to SEQ ID NO: 24 and/or the TCR beta chain construct comprises a complementarity determining region 3 (CDR3) having at least 90% sequence identity to an amino acid as set forth in SEQ ID NO: 20 and wherein the TCR beta chain construct comprises a variable region comprising a sequence having at least 80% sequence identity to SEQ ID NO: 108; or ii) a protein encoded by said nucleic acid of part i comprising a TCR construct capable of specifically binding to an epitope from said defined antigen in complex with a human MHC I; or iii) a host cell comprising the nucleic acid of part i, wherein said defined antigen preferably is a tumor-associated or tumor-specific antigen selected from the group comprising cancer-testis-antigens such as NY-ESO-1.

12. A kit of claim 11, wherein the nucleic acid of part a encodes a TCR construct capable of specifically binding to an epitope from NY-ESO-1 in complex with a human MHC, wherein the TCR construct is capable of specifically binding to the epitope consisting of SEQ ID: 21 in complex with HLA-DR4, wherein the TCR alpha chain construct comprises a CDR3 as set forth in SEQ ID NO: 1 or having 100% sequence identity to an amino acid selected from SEQ ID NO: 2, 4-9 and/or the TCR beta chain construct comprises a complementarity determining region 3 (CDR3) having 100% sequence identity to an amino acid selected from SEQ ID NO: 10-18.

13. The pharmaceutical composition of claim 8 for use in the diagnosis, prevention and/or treatment of a proliferative or viral disease,
preferably a benign or malignant tumor disease, wherein the proliferating cells or the tumor expresses NY-ESO-1.

14. The pharmaceutical composition of claim 13 for use in immune therapy, preferably, in adoptive T cell therapy or TCR gene therapy.

15. A host cell comprising a nucleic acid of claim 1, wherein the TCR construct is capable of specifically binding to the epitope consisting of SEQ ID NO:103 in complex with HLA-A2, wherein the TCR alpha chain construct comprises a complementarity determining region 3 (CDR3) having at least 90% sequence identity to SEQ ID NO: 19 and the TCR beta chain construct comprises a complementarity determining region 3 (CDR3) having at least 90% sequence identity to SEQ ID NO: 20, and wherein the host cell preferably is a CD8+T cell.

16. A pharmaceutical composition comprising a protein of claim 6 comprising a TCR construct capable of specifically binding to an epitope from NY-ESO-1 in complex with a human MHC.

17. A pharmaceutical composition comprising a host cell of claim 7 expressing a TCR construct capable of specifically binding to an epitope from NY-ESO-1 in complex with a human MHC.

18. The kit of claim 11 for use in the diagnosis, prevention and/or treatment of a proliferative or viral disease, preferably a benign or malignant tumor disease, wherein the proliferating cells or the tumor expresses NY-ESO-1.

19. The kit for use of claim 18 for use in immune therapy, preferably, in adoptive T cell therapy or TCR gene therapy.

20. The nucleic acid of claim 2, wherein the TCR alpha chain construct comprises a CDR3 having 100% sequence identity to an amino acid selected from SEQ ID NOs: 2 and 4-9 and/or the TCR beta chain construct comprises a complementarity determining region 3 (CDR3) having 100% sequence identity to an amino acid selected from SEQ ID NO: 10-18.

21. The nucleic acid of claim 4, wherein the TCR alpha chain construct comprises a complementarity determining region 3 (CDR3) having 100% sequence identity-to SEQ ID NO: 19 and/or the TCR beta chain construct comprises a complementarity determining region 3 (CDR3) having 100% sequence identity to SEQ ID NO: 20.

22. The host cell of claim 7, wherein the TCR alpha chain construct comprises a CDR3 having 100% sequence identity to an amino acid selected from SEQ ID NOs: 2 and 4-9 and/or the TCR beta chain construct comprises a complementarity determining region 3 (CDR3) having 100% sequence identity to an amino acid selected from SEQ ID NOs: 10-18.

23. The host cell of claim 15, wherein the TCR alpha chain construct comprises a complementarity determining region 3 (CDR3) having 100% sequence identity to SEQ ID NO: 19 and/or the TCR beta chain construct comprises a complementarity determining region 3 (CDR3) having 100% sequence identity to SEQ ID NO: 20.

24. A nucleic acid encoding at least one T cell receptor (TCR) alpha chain construct and/or TCR beta chain construct of a TCR construct capable of specifically binding to an epitope from NY-ESO-1 in complex with a human MHC, wherein the TCR alpha chain construct comprises a complementarity determining region 3 (CDR3) having at least 90% sequence identity to an amino acid as set forth in SEQ ID NO: 3 and wherein the TCR alpha chain construct comprises a variable region comprising a sequence having at least 80% sequence identity to SEQ ID NO: 24 and/or the TCR beta chain construct comprises a complementarity determining region 3 (CDR3) having at least 90% sequence identity to an amino acid as set forth in SEQ ID NO: 20 and wherein the TCR beta chain construct comprises a variable region comprising a sequence having at least 80% sequence identity to SEQ ID NO: 108.

25. The nucleic acid of claim 24, wherein the TCR alpha chain construct comprises a complementarity determining region 3 (CDR3) having 100% sequence identity-to SEQ ID NO: 3 and/or the TCR beta chain construct comprises a complementarity determining region 3 (CDR3) having 100% sequence identity to SEQ ID NO: 20.

26. The nucleic acid of claim 24, wherein the TCR construct is capable of specifically binding to the epitope consisting of SEQ ID:21 in complex with HLA-DR4.

27. The nucleic acid of claim 24, wherein the TCR construct is capable of specifically binding to the epitope consisting of SEQ ID NO:103 in complex with HLA-A2.

28. A host cell comprising a nucleic acid of claim 24, wherein the TCR construct is capable of specifically binding to the epitope consisting of SEQ ID NO:21 in complex with HLA-DR4.

29. A host cell comprising a nucleic acid of claim 24, wherein the TCR construct is capable of specifically binding to the epitope consisting of SEQ ID NO:103 in complex with HLA-A2.

30. The nucleic acid of claim 1, wherein the TCR construct is capable of specifically binding to the epitope consisting of SEQ ID:103 in complex with HLA-A2, wherein the TCR alpha chain construct comprises a complementarity determining region 3 (CDR3) having at least 90% sequence identity to SEQ ID NO: 19.

31. The nucleic acid of claim 30, wherein the TCR alpha chain construct comprises a complementarity determining region 3 (CDR3) having 100% sequence identity to SEQ ID NO: 19.

32. A host cell comprising a nucleic acid of claim 1, wherein the TCR construct is capable of specifically binding to the epitope consisting of SEQ ID NO:103 in complex with HLA-A2, wherein the TCR alpha chain construct comprises a complementarity determining region 3 (CDR3) having at least 90% sequence identity to SEQ ID NO: 19, and wherein the host cell preferably is a CD8+T cell.

33. The host cell of claim 32, wherein the TCR alpha chain construct comprises a complementarity determining region 3 (CDR3) having 100% sequence identity to SEQ ID NO: 19.

34. The host cell of claim 7, wherein the host cell is a human T cell.

35. The host cell of claim 15, wherein the host cell is a human T cell.

36. The host cell of claim 28, wherein the host cell is a human T cell.

37. The host cell of claim 29, wherein the host cell is a human T cell.

38. The host cell of claim 32, wherein the host cell is a human T cell.

39. The nucleic acid of claim 2, wherein the TCR alpha chain construct comprises a CDR3 having SEQ ID NO: 2, and/or the TCR beta chain construct comprises a CDR3 having SEQ ID NO: 11.

40. The nucleic acid of claim 39, wherein the TCR alpha chain construct comprises a variable region having at least 80% sequence identity to SEQ ID NO: 23, and/or the TCR beta chain construct comprises a variable region having at least 80% sequence identity to SEQ ID NO: 59.

41. The nucleic acid of claim 40, wherein the TCR alpha chain construct comprises a variable region having SEQ ID NO: 23, and/or the TCR beta chain construct comprises a variable region having SEQ ID NO: 59.

42. A host cell comprising a nucleic acid of claim 39, wherein the TCR construct is capable of specifically binding to the epitope consisting of SEQ ID NO:21 in complex with HLA-DR4.

43. The host cell of claim 42, wherein the host cell is a human T cell.

\* \* \* \* \*

SEQUENCE LISTING

```
<160> NUMBER OF SEQ ID NOS: 112

<210> SEQ ID NO 1
<211> LENGTH: 13
<212> TYPE: PRT
<213> ORGANISM: Homo sapiens
<220> FEATURE:
<223> OTHER INFORMATION: TCR3598 alpha chain CDR3

<400> SEQUENCE: 1

Cys Ala Met Arg Gln Gly Gly Ser Glu Lys Leu Val Phe
1               5                   10

<210> SEQ ID NO 2
<211> LENGTH: 15
<212> TYPE: PRT
<213> ORGANISM: Homo sapiens
<220> FEATURE:
<223> OTHER INFORMATION: TCR3598_2 alpha chain CDR3

<400> SEQUENCE: 2

Cys Ala Leu Arg Asp Ser Gly Gly Gly Ala Asp Gly Leu Thr Phe
1               5                   10                  15

<210> SEQ ID NO 3
<211> LENGTH: 13
<212> TYPE: PRT
<213> ORGANISM: Homo sapiens
<220> FEATURE:
<223> OTHER INFORMATION: TCR5412 alpha chain CDR3

<400> SEQUENCE: 3

Cys Ala Val Thr Leu Asn Arg Asp Asp Lys Ile Ile Phe
1               5                   10

<210> SEQ ID NO 4
<211> LENGTH: 14
<212> TYPE: PRT
<213> ORGANISM: Homo sapiens
<220> FEATURE:
<223> OTHER INFORMATION: TCR5412_2 alpha chain CDR3

<400> SEQUENCE: 4

Cys Ala Val Thr Arg Asn Ser Gly Asn Thr Pro Leu Val Phe
1               5                   10

<210> SEQ ID NO 5
<211> LENGTH: 16
<212> TYPE: PRT
<213> ORGANISM: Homo sapiens
<220> FEATURE:
<223> OTHER INFORMATION: TCR5412_3

<400> SEQUENCE: 5

Cys Ala Gly Gln Gln Asn Ser Gly Gly Ser Asn Tyr Lys Leu Thr Phe
1               5                   10                  15
```

```
<210> SEQ ID NO 6
<211> LENGTH: 13
<212> TYPE: PRT
<213> ORGANISM: Homo sapiens
<220> FEATURE:
<223> OTHER INFORMATION: TCR3600 alpha chain CDR3

<400> SEQUENCE: 6

Cys Ala Val Pro Asn Ser Gly Asn Thr Pro Leu Val Phe
1               5                   10

<210> SEQ ID NO 7
<211> LENGTH: 13
<212> TYPE: PRT
<213> ORGANISM: Homo sapiens
<220> FEATURE:
<223> OTHER INFORMATION: TCR5712 alpha chain CDR3

<400> SEQUENCE: 7

Cys Ala Val Pro Asn Ser Gly Asn Thr Pro Leu Val Phe
1               5                   10

<210> SEQ ID NO 8
<211> LENGTH: 13
<212> TYPE: PRT
<213> ORGANISM: Homo sapiens
<220> FEATURE:
<223> OTHER INFORMATION: TCR5415 alpha chain CDR3

<400> SEQUENCE: 8

Cys Ala Val Pro Asn Ser Gly Asn Thr Pro Leu Val Phe
1               5                   10

<210> SEQ ID NO 9
<211> LENGTH: 13
<212> TYPE: PRT
<213> ORGANISM: Homo sapiens
<220> FEATURE:
<223> OTHER INFORMATION: TCR5713 alpha chain CDR3

<400> SEQUENCE: 9

Cys Ala Glu Ala Asn Gln Ala Gly Thr Ala Leu Ile Phe
1               5                   10

<210> SEQ ID NO 10
<211> LENGTH: 13
<212> TYPE: PRT
<213> ORGANISM: Homo sapiens
<220> FEATURE:
<223> OTHER INFORMATION: TCR3598 beta chain CDR3

<400> SEQUENCE: 10

Cys Ala Ser Ser Gly Gln Gly Ala Gly Thr Gln Tyr Phe
1               5                   10

<210> SEQ ID NO 11
<211> LENGTH: 15
<212> TYPE: PRT
<213> ORGANISM: Homo sapiens
<220> FEATURE:
<223> OTHER INFORMATION: TCR3598_2 beta chain CDR3

<400> SEQUENCE: 11

Cys Ala Ser Ser Val Met Thr Gly Leu Asn Thr Glu Ala Phe Phe
1               5                   10                  15

<210> SEQ ID NO 12
```

```
<211> LENGTH: 14
<212> TYPE: PRT
<213> ORGANISM: Homo sapiens
<220> FEATURE:
<223> OTHER INFORMATION: TCR5412 beta chain CDR3

<400> SEQUENCE: 12

Cys Ala Ser Ser Leu Asp Arg Pro Tyr Asn Glu Gln Phe Phe
 1               5                  10

<210> SEQ ID NO 13
<211> LENGTH: 15
<212> TYPE: PRT
<213> ORGANISM: Homo sapiens
<220> FEATURE:
<223> OTHER INFORMATION: TCR5412_2 beta chain CDR3

<400> SEQUENCE: 13

Cys Ala Ser Ser Phe Leu Ala Ser Val Gly Tyr Glu Gln Tyr Phe
 1               5                  10                  15

<210> SEQ ID NO 14
<211> LENGTH: 12
<212> TYPE: PRT
<213> ORGANISM: Homo sapiens
<220> FEATURE:
<223> OTHER INFORMATION: TCR5412_3 beta chain CDR3

<400> SEQUENCE: 14

Cys Ala Ser Ser Pro Pro Leu Gly Glu Gln Tyr Phe
 1               5                  10

<210> SEQ ID NO 15
<211> LENGTH: 11
<212> TYPE: PRT
<213> ORGANISM: Homo sapiens
<220> FEATURE:
<223> OTHER INFORMATION: TCR3600 beta chain CDR3

<400> SEQUENCE: 15

Cys Ala Ser Ser Val Ile Tyr Glu Gln Tyr Phe
 1               5                  10

<210> SEQ ID NO 16
<211> LENGTH: 11
<212> TYPE: PRT
<213> ORGANISM: Homo sapiens
<220> FEATURE:
<223> OTHER INFORMATION: TCR5712 beta chain CDR3

<400> SEQUENCE: 16

Cys Ala Ser Ser Ile Ile Tyr Glu Gln Tyr Phe
 1               5                  10

<210> SEQ ID NO 17
<211> LENGTH: 11
<212> TYPE: PRT
<213> ORGANISM: Homo sapiens
<220> FEATURE:
<223> OTHER INFORMATION: TCR5415 beta chain CDR3

<400> SEQUENCE: 17

Cys Ala Ser Ser Val Tyr Tyr Glu Gln Tyr Phe
 1               5                  10

<210> SEQ ID NO 18
<211> LENGTH: 15
```

```
<212> TYPE: PRT
<213> ORGANISM: Homo sapiens
<220> FEATURE:
<223> OTHER INFORMATION: TCR5713 beta chain CDR3

<400> SEQUENCE: 18

Cys Ala Ser Ser Gly Leu Ala Gly Val Thr Gly Glu Leu Phe Phe
1               5                   10                  15

<210> SEQ ID NO 19
<211> LENGTH: 13
<212> TYPE: PRT
<213> ORGANISM: Homo sapiens
<220> FEATURE:
<223> OTHER INFORMATION: HLA-A2 restricted TCR-ESO alpha chain CDR3

<400> SEQUENCE: 19

Cys Ala Gly Glu Gly Asn Tyr Gly Gln Asn Phe Val Phe
1               5                   10

<210> SEQ ID NO 20
<211> LENGTH: 14
<212> TYPE: PRT
<213> ORGANISM: Homo sapiens
<220> FEATURE:
<223> OTHER INFORMATION: HLA-A2 restricted TCR-ESO beta chain CDR3

<400> SEQUENCE: 20

Cys Ala Ser Asn Ile Ala Gly Gly Tyr Asn Glu Gln Phe Phe
1               5                   10

<210> SEQ ID NO 21
<211> LENGTH: 20
<212> TYPE: PRT
<213> ORGANISM: Homo sapiens
<220> FEATURE:
<223> OTHER INFORMATION: HLA-DR4 epitope NY-ESO-1 116-135

<400> SEQUENCE: 21

Leu Pro Val Pro Gly Val Leu Leu Lys Glu Phe Thr Val Ser Gly Asn
1               5                   10                  15

Ile Leu Thr Ile
            20

<210> SEQ ID NO 22
<211> LENGTH: 134
<212> TYPE: PRT
<213> ORGANISM: Homo sapiens
<220> FEATURE:
<223> OTHER INFORMATION: TCR3598 TCR alpha chain specific for HLA-DR4
      epitope NY-ESO-1 116-135 , variable region

<400> SEQUENCE: 22

Met Met Lys Ser Leu Arg Val Leu Leu Val Ile Leu Trp Leu Gln Leu
1               5                   10                  15

Ser Trp Val Trp Ser Gln Gln Lys Glu Val Gln Asp Pro Gly Pro
            20                  25                  30

Leu Ser Val Pro Glu Gly Ala Ile Val Ser Leu Asn Cys Thr Tyr Ser
        35                  40                  45

Asn Ser Ala Phe Gln Tyr Phe Met Trp Tyr Arg Gln Tyr Ser Arg Lys
    50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
```

```
                    85                  90                  95
Phe Ile Arg Asp Ser Gln Pro Ser Asp Ser Ala Thr Tyr Leu Cys Ala
                100                 105                 110
Met Arg Gln Gly Gly Ser Glu Lys Leu Val Phe Gly Lys Gly Thr Lys
            115                 120                 125
Leu Thr Val Asn Pro Tyr
        130
```

```
<210> SEQ ID NO 23
<211> LENGTH: 134
<212> TYPE: PRT
<213> ORGANISM: Homo sapiens
<220> FEATURE:
<223> OTHER INFORMATION: TCR3598_2 TCR alpha chain specific for HLA-DR4
      epitope NY-ESO-1 116-135 , variable region

<400> SEQUENCE: 23

Met Asn Tyr Ser Pro Gly Leu Val Ser Leu Ile Leu Leu Leu Leu Gly
1               5                   10                  15
Arg Thr Arg Gly Asp Ser Val Thr Gln Met Glu Gly Pro Val Thr Leu
                20                  25                  30
Ser Glu Glu Ala Phe Leu Thr Ile Asn Cys Thr Tyr Thr Ala Thr Gly
            35                  40                  45
Tyr Pro Ser Leu Phe Trp Tyr Val Gln Tyr Pro Gly Glu Gly Leu Gln
        50                  55                  60
Leu Leu Leu Lys Ala Thr Lys Ala Asp Asp Lys Gly Ser Asn Lys Gly
65                  70                  75                  80
Phe Glu Ala Thr Tyr Arg Lys Glu Thr Thr Ser Phe His Leu Glu Lys
                85                  90                  95
Gly Ser Val Gln Val Ser Asp Ser Ala Val Tyr Phe Cys Ala Leu Arg
                100                 105                 110
Asp Ser Gly Gly Gly Ala Asp Gly Leu Thr Phe Gly Lys Gly Thr His
            115                 120                 125
Leu Ile Ile Gln Pro Tyr
        130
```

```
<210> SEQ ID NO 24
<211> LENGTH: 133
<212> TYPE: PRT
<213> ORGANISM: Homo sapiens
<220> FEATURE:
<223> OTHER INFORMATION: TCR5412 TCR alpha chain specific for HLA-DR4
      epitope NY-ESO-1 116-135 , variable region

<400> SEQUENCE: 24

Met Leu Leu Leu Leu Val Pro Ala Phe Gln Val Ile Phe Thr Leu Gly
1               5                   10                  15
Gly Thr Arg Ala Gln Ser Val Thr Gln Leu Asp Ser Gln Val Pro Val
                20                  25                  30
Phe Glu Glu Ala Pro Val Glu Leu Arg Cys Asn Tyr Ser Ser Ser Val
            35                  40                  45
Ser Val Tyr Leu Phe Trp Tyr Val Gln Tyr Pro Asn Gln Gly Leu Gln
        50                  55                  60
Leu Leu Leu Lys Tyr Leu Ser Gly Ser Thr Leu Val Glu Ser Ile Asn
65                  70                  75                  80
Gly Phe Glu Ala Glu Phe Asn Lys Ser Gln Thr Ser Phe His Leu Arg
                85                  90                  95
Lys Pro Ser Val His Ile Ser Asp Thr Ala Glu Tyr Phe Cys Ala Val
```

```
                100             105             110
Thr Leu Asn Arg Asp Asp Lys Ile Ile Phe Gly Lys Gly Thr Arg Leu
        115             120             125

His Ile Leu Pro Asn
    130

<210> SEQ ID NO 25
<211> LENGTH: 134
<212> TYPE: PRT
<213> ORGANISM: Homo sapiens
<220> FEATURE:
<223> OTHER INFORMATION: TCR5412_2 TCR alpha chain specific for HLA-DR4
      epitope NY-ESO-1 116-135 , variable region

<400> SEQUENCE: 25

Met Leu Leu Leu Leu Val Pro Ala Phe Gln Val Ile Phe Thr Leu Gly
1               5                   10                  15

Gly Thr Arg Ala Gln Ser Val Thr Gln Leu Asp Ser Gln Val Pro Val
            20                  25                  30

Phe Glu Glu Ala Pro Val Glu Leu Arg Cys Asn Tyr Ser Ser Ser Val
        35                  40                  45

Ser Val Tyr Leu Phe Trp Tyr Val Gln Tyr Pro Asn Gln Gly Leu Gln
    50                  55                  60

Leu Leu Leu Lys Tyr Leu Ser Gly Ser Thr Leu Val Glu Ser Ile Asn
65                  70                  75                  80

Gly Phe Glu Ala Glu Phe Asn Lys Ser Gln Thr Ser Phe His Leu Arg
                85                  90                  95

Lys Pro Ser Val His Ile Ser Asp Thr Ala Glu Tyr Phe Cys Ala Val
            100                 105                 110

Thr Arg Asn Ser Gly Asn Thr Pro Leu Val Phe Gly Lys Gly Thr Arg
        115                 120                 125

Leu Ser Val Ile Ala Asn
    130

<210> SEQ ID NO 26
<211> LENGTH: 133
<212> TYPE: PRT
<213> ORGANISM: Homo sapiens
<220> FEATURE:
<223> OTHER INFORMATION: TCR5412_3 TCR alpha chain specific for HLA-DR4
      epitope NY-ESO-1 116-135 , variable region

<400> SEQUENCE: 26

Met Leu Leu Glu His Leu Leu Ile Ile Leu Trp Met Gln Leu Thr Trp
1               5                   10                  15

Val Ser Gly Gln Gln Leu Asn Gln Ser Pro Gln Ser Met Phe Ile Gln
            20                  25                  30

Glu Gly Glu Asp Val Ser Met Asn Cys Thr Ser Ser Ser Ile Phe Asn
        35                  40                  45

Thr Trp Leu Trp Tyr Lys Gln Asp Pro Gly Glu Gly Pro Val Leu Leu
    50                  55                  60

Ile Ala Leu Tyr Lys Ala Gly Glu Leu Thr Ser Asn Gly Arg Leu Thr
65                  70                  75                  80

Ala Gln Phe Gly Ile Thr Arg Lys Asp Ser Phe Leu Asn Ile Ser Ala
                85                  90                  95

Ser Ile Pro Ser Asp Val Gly Ile Tyr Phe Cys Ala Gly Gln Gln Asn
            100                 105                 110

Ser Gly Gly Ser Asn Tyr Lys Leu Thr Phe Gly Lys Gly Thr Leu Leu
```

Thr Val Asn Pro Asn
    130

<210> SEQ ID NO 27
<211> LENGTH: 132
<212> TYPE: PRT
<213> ORGANISM: Homo sapiens
<220> FEATURE:
<223> OTHER INFORMATION: TCR3600 TCR alpha chain specific for HLA-DR4
      epitope NY-ESO-1 116-135 , variable region

<400> SEQUENCE: 27

Met Val Lys Ile Arg Gln Phe Leu Leu Ala Ile Leu Trp Leu Gln Leu
1               5                   10                  15

Ser Cys Val Ser Ala Ala Lys Asn Glu Val Glu Gln Ser Pro Gln Asn
            20                  25                  30

Leu Thr Ala Gln Glu Gly Glu Phe Ile Thr Ile Asn Cys Ser Tyr Ser
        35                  40                  45

Val Gly Ile Ser Ala Leu His Trp Leu Gln Gln His Pro Gly Gly Gly
    50                  55                  60

Ile Val Ser Leu Phe Met Leu Ser Ser Gly Lys Lys Lys His Gly Arg
65                  70                  75                  80

Leu Ile Ala Thr Ile Asn Ile Gln Glu Lys His Ser Ser Leu His Ile
                85                  90                  95

Thr Ala Ser His Pro Arg Asp Ser Ala Val Tyr Ile Cys Ala Val Pro
            100                 105                 110

Asn Ser Gly Asn Thr Pro Leu Val Phe Gly Lys Gly Thr Arg Leu Ser
        115                 120                 125

Val Ile Ala Asn
    130

<210> SEQ ID NO 28
<211> LENGTH: 132
<212> TYPE: PRT
<213> ORGANISM: Homo sapiens
<220> FEATURE:
<223> OTHER INFORMATION: TCR5712 TCR alpha chain specific for HLA-DR4
      epitope NY-ESO-1 116-135 , variable region

<400> SEQUENCE: 28

Met Val Lys Ile Arg Gln Phe Leu Leu Ala Ile Leu Trp Leu Gln Leu
1               5                   10                  15

Ser Cys Val Ser Ala Ala Lys Asn Glu Val Glu Gln Ser Pro Gln Asn
            20                  25                  30

Leu Thr Ala Gln Glu Gly Glu Phe Ile Thr Ile Asn Cys Ser Tyr Ser
        35                  40                  45

Val Gly Ile Ser Ala Leu His Trp Leu Gln Gln His Pro Gly Gly Gly
    50                  55                  60

Ile Val Ser Leu Phe Met Leu Ser Ser Gly Lys Lys Lys His Gly Arg
65                  70                  75                  80

Leu Ile Ala Thr Ile Asn Ile Gln Glu Lys His Ser Ser Leu His Ile
                85                  90                  95

Thr Ala Ser His Pro Arg Asp Ser Ala Val Tyr Ile Cys Ala Val Pro
            100                 105                 110

Asn Ser Gly Asn Thr Pro Leu Val Phe Gly Lys Gly Thr Arg Leu Ser
        115                 120                 125

Val Ile Ala Asn

<210> SEQ ID NO 29
<211> LENGTH: 132
<212> TYPE: PRT
<213> ORGANISM: Homo sapiens

<400> SEQUENCE: 29

```
Met Val Lys Ile Arg Gln Phe Leu Leu Ala Ile Leu Trp Leu Gln Leu
1               5                   10                  15

Ser Cys Val Ser Ala Ala Lys Asn Glu Val Glu Gln Ser Pro Gln Asn
                20                  25                  30

Leu Thr Ala Gln Glu Gly Glu Phe Ile Thr Ile Asn Cys Ser Tyr Ser
            35                  40                  45

Val Gly Ile Ser Ala Leu His Trp Leu Gln Gln His Pro Gly Gly Gly
        50                  55                  60

Ile Val Ser Leu Phe Met Leu Ser Ser Gly Lys Lys His Gly Arg
65                  70                  75                  80

Leu Ile Ala Thr Ile Asn Ile Gln Glu Lys His Ser Ser Leu His Ile
                85                  90                  95

Thr Ala Ser His Pro Arg Asp Ser Ala Val Tyr Ile Cys Ala Val Pro
            100                 105                 110

Asn Ser Gly Asn Thr Pro Leu Val Phe Gly Lys Gly Thr Arg Leu Ser
        115                 120                 125

Val Ile Ala Asn
        130
```

<210> SEQ ID NO 30
<211> LENGTH: 133
<212> TYPE: PRT
<213> ORGANISM: Homo sapiens
<220> FEATURE:
<223> OTHER INFORMATION: TCR5713 TCR alpha chain specific for HLA-DR4
      epitope NY-ESO-1 116-135 , variable region

<400> SEQUENCE: 30

```
Met Lys Thr Phe Ala Gly Phe Ser Phe Leu Phe Leu Trp Leu Gln Leu
1               5                   10                  15

Asp Cys Met Ser Arg Gly Glu Asp Val Glu Gln Ser Leu Phe Leu Ser
                20                  25                  30

Val Arg Glu Gly Asp Ser Ser Val Ile Asn Cys Thr Tyr Thr Asp Ser
            35                  40                  45

Ser Ser Thr Tyr Leu Tyr Trp Tyr Lys Gln Glu Pro Gly Ala Gly Leu
        50                  55                  60

Gln Leu Leu Thr Tyr Ile Phe Ser Asn Met Asp Met Lys Gln Asp Gln
65                  70                  75                  80

Arg Leu Thr Val Leu Leu Asn Lys Lys Asp Lys His Leu Ser Leu Arg
                85                  90                  95

Ile Ala Asp Thr Gln Thr Gly Asp Ser Ala Ile Tyr Phe Cys Ala Glu
            100                 105                 110

Ala Asn Gln Ala Gly Thr Ala Leu Ile Phe Gly Lys Gly Thr Thr Leu
        115                 120                 125

Ser Val Ser Ser Asn
        130
```

<210> SEQ ID NO 31
<211> LENGTH: 400
<212> TYPE: DNA

<213> ORGANISM: Artificial Sequence
<220> FEATURE:
<223> OTHER INFORMATION: TCR3598 TCR alpha chain specific for HLA-DR4
      epitope NY-ESO-1 116-135 , variable region

<400> SEQUENCE: 31

```
atgatgaaat ccttgagagt tttactggtg atcctgtggc ttcagttaag ctgggtttgg     60
agccaacaga aggaggtgga gcaggatcct ggaccactca gtgttccaga gggagccatt    120
gtttctctca actgcactta cagcaacagt gcttttcaat acttcatgtg gtacagacag    180
tattccagaa aaggccctga gttgctgatg tacacatact ccagtggtaa caagaagat    240
ggaaggttta cagcacaggt cgataaatcc agcaagtata tctccttgtt catcagagac    300
tcacagccca gtgattcagc cacctacctc tgtgcaatga ggcagggcgg atctgaaaag    360
ctggtctttg gaaagggaac gaaactgaca gtaaacccat                          400
```

<210> SEQ ID NO 32
<211> LENGTH: 400
<212> TYPE: DNA
<213> ORGANISM: Artificial Sequence
<220> FEATURE:
<223> OTHER INFORMATION: TCR3598_2 TCR alpha chain specific for HLA-DR4
      epitope NY-ESO-1 116-135 , variable region

<400> SEQUENCE: 32

```
atgaactact ctcccggcct ggtgtctctg attctgctgc tgctgggccg gaccagaggc     60
gattctgtga cccagatgga aggccccgtg accctgagcg aggaagcctt cctgaccatc    120
aattgcacct acaccgccac cggctacccc agcctgtttt ggtacgtgca gtaccccggc    180
gagggcctgc agctgctgct gaaagccacc aaggccgacg acaagggcag caacaagggc    240
ttcgaggcca cctaccggaa agagacaacc agcttccacc tggaaaaggg cagcgtgcag    300
gtgtccgact ccgccgtgta tttctgcgcc ctgagagatt ctggcggcgg agccgatggc    360
ctgacctttg gcaagggcac acacctgatc atccagccct                          400
```

<210> SEQ ID NO 33
<211> LENGTH: 397
<212> TYPE: DNA
<213> ORGANISM: Artificial Sequence
<220> FEATURE:
<223> OTHER INFORMATION: TCR5412 TCR alpha chain specific for HLA-DR4
      epitope NY-ESO-1 116-135 , variable region

<400> SEQUENCE: 33

```
atgctcctgc tgctggtgcc tgccttccaa gtgatcttca ccctgggcgg caccagagcc     60
cagagcgtga cacagctgga tagccaggtg cccgtgttcg aagaggcccc tgtggaactg    120
cggtgcaact actccagcag cgtgtccgtg tacctgtttt ggtacgtgca gtaccccaac    180
cagggcctgc agctgctgct gaagtacctg agcggctcca ccctggtgga atccatcaac    240
ggcttcgagg ccgagttcaa caagagccag accagcttcc acctgagaaa gcccagcgtg    300
cacatcagcg ataccgccga gtacttctgc gccgtgaccc tgaaccggga cgacaagatc    360
atcttcggca agggcaccag actgcacatc ctgccca                             397
```

<210> SEQ ID NO 34
<211> LENGTH: 400
<212> TYPE: DNA
<213> ORGANISM: Artificial Sequence
<220> FEATURE:
<223> OTHER INFORMATION: TCR5412_2 TCR alpha chain specific for HLA-DR4
      epitope NY-ESO-1 116-135 , variable region

<400> SEQUENCE: 34

```
atgctcctgc tgctggtgcc tgccttccaa gtgatcttca ccctgggcgg caccagggcc      60
cagtctgtga cacagctgga tagccaggtg cccgtgttcg aagaggcccc tgtggaactg     120
cggtgcaact actccagcag cgtgtccgtg tacctgtttt ggtacgtgca gtaccccaac     180
cagggcctgc agctgctgct gaagtacctg agcggctcca ccctggtgga atccatcaac     240
ggcttcgagg ccgagttcaa caagagccag accagcttcc atctgcggaa gcccagcgtg     300
cacatcagcg ataccgccga gtacttctgt gccgtgaccc ggaactccgg caacacccct     360
ctggtgtttg gcaagggcac acggctgagc gtgatcgcca                           400
```

<210> SEQ ID NO 35
<211> LENGTH: 397
<212> TYPE: DNA
<213> ORGANISM: Artificial Sequence
<220> FEATURE:
<223> OTHER INFORMATION: TCR5412_3 TCR alpha chain specific for HLA-DR4
      epitope NY-ESO-1 116-135 , variable region

<400> SEQUENCE: 35

```
atgctgctgg aacatctgct gatcatcctg tggatgcagc tgacctgggt gtccggccag      60
cagctgaatc agagcccca gagcatgttc atccaggaag gcgaggacgt gtccatgaac     120
tgcaccagca gcagcatctt caatacctgg ctgtggtaca gcaggaccc cggcgaagga     180
cccgtgctgc tgatcgccct gtacaaagcc ggcgagctga ccagcaatgg caggctgaca     240
gcccagttcg gcattacccg gaaggacagc ttcctgaaca tcagcgcctc catccccagc     300
gacgtgggca tctatttctg cgccggacag cagaactccg gcggctccaa ctacaagctg     360
accttcggca agggcacact gctgacagtg aacccca                              397
```

<210> SEQ ID NO 36
<211> LENGTH: 394
<212> TYPE: DNA
<213> ORGANISM: Artificial Sequence
<220> FEATURE:
<223> OTHER INFORMATION: TCR3600 TCR alpha chain specific for HLA-DR4
      epitope NY-ESO-1 116-135 , variable region

<400> SEQUENCE: 36

```
atggtcaaaa tccggcagtt cctgctggcc atcctgtggc tgcagctgag ctgtgtgtcc      60
gccgccaaga cgaggtgga acagagcccc cagaacctga ccgctcagga aggcgagttc     120
atcaccatca ctgcagcta cagcgtgggc atcagcgccc tgcattggct gcagcagcat     180
cctggcggag catcgtgtc tctgttcatg ctgagcagcg aaagaagaa gcacggccgg     240
ctgatcgcca caatcaacat ccaggaaaag cacagcagcc tgcacatcac cgccagccac     300
cctagagaca gcgccgtgta catctgcgcc gtgcccaata gcggcaacac ccctctggtg     360
ttcggcaagg gcaccagact gagcgtgatc gcca                                 394
```

<210> SEQ ID NO 37
<211> LENGTH: 394
<212> TYPE: DNA
<213> ORGANISM: Artificial Sequence
<220> FEATURE:
<223> OTHER INFORMATION: TCR5712 TCR alpha chain specific for HLA-DR4
      epitope NY-ESO-1 116-135 , variable region

<400> SEQUENCE: 37

```
atggtcaaaa tccggcagtt cctgctggcc atcctgtggc tgcagctgag ctgtgtgtcc      60
```

```
gccgccaaga acgaggtgga acagagcccc cagaacctga ccgctcagga aggcgagttc    120
atcaccatca actgcagcta cagcgtgggc atcagcgccc tgcattggct gcagcagcat    180
cctggcggag gcatcgtgtc tctgttcatg ctgagcagcg aaagaagaa gcacggccgg     240 ctgatcgcca caatcaacat ccaggaaaag cacagcagcc tgcacatcac cgccagccac    300
cctagagaca cgccgtgta catctgcgcc gtgcccaata gcggcaacac ccctctggtg     360
ttcggcaagg gcaccagact gagcgtgatc gcca                                 394
```

<210> SEQ ID NO 38
<211> LENGTH: 394
<212> TYPE: DNA
<213> ORGANISM: Artificial Sequence
<220> FEATURE:
<223> OTHER INFORMATION: TCR5415 TCR alpha chain specific for HLA-DR4
      epitope NY-ESO-1 116-135 , variable region

<400> SEQUENCE: 38

```
atggtcaaaa tccggcagtt cctgctggcc atcctgtggc tgcagctgag ctgtgtgtcc    60
gccgccaaga acgaggtgga acagagcccc cagaacctga ccgctcagga aggcgagttc    120
atcaccatca actgcagcta cagcgtgggc atcagcgccc tgcattggct gcagcagcat    180
cctggcggag gcatcgtgtc tctgttcatg ctgagcagcg aaagaagaa gcacggccgg     240 ctgatcgcca caatcaacat ccaggaaaag cacagcagcc tgcacatcac cgccagccac    300
cctagagaca cgccgtgta catctgcgcc gtgcccaata gcggcaacac ccctctggtg     360
ttcggcaagg gcaccagact gagcgtgatc gcca                                 394
```

<210> SEQ ID NO 39
<211> LENGTH: 397
<212> TYPE: DNA
<213> ORGANISM: Artificial Sequence
<220> FEATURE:
<223> OTHER INFORMATION: TCR5713 TCR alpha chain specific for HLA-DR4
      epitope NY-ESO-1 116-135 , variable region

<400> SEQUENCE: 39

```
atgaagacct tcgccggctt cagcttcctg ttcctgtggc tgcagctgga ctgcatgagc    60
agaggcgagg acgtggaaca gagcctgttt ctgagcgtgc gcgagggcga cagcagcgtg    120
atcaattgca cctacaccga cagctccagc acatacctgt actggtataa gcaggaaccc    180
ggcgctggcc tgcagctgct gacctacatc ttctccaaca tggacatgaa gcaggaccag    240
cggctgacag tgctgctgaa caagaaggac aagcacctga gcctgcggat cgccgatacc    300
cagacaggcg actccgccat ctatttctgc gccgaggcca tcaggccgg caccgccctg    360 atctttggca agggcacaac actgagcgtg tccagca                              397
```

<210> SEQ ID NO 40
<211> LENGTH: 270
<212> TYPE: PRT
<213> ORGANISM: Artificial Sequence
<220> FEATURE:
<223> OTHER INFORMATION: TCR3598 TCR alpha chain specific for HLA-DR4
      epitope NY-ESO-1 116-135

<400> SEQUENCE: 40

```
Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30
```

Leu Ser Val Pro Glu Gly Ala Ile Val Ser Leu Asn Cys Thr Tyr Ser
            35                  40                  45

Asn Ser Ala Phe Gln Tyr Phe Met Trp Tyr Arg Gln Tyr Ser Arg Lys
        50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
            100                 105                 110

Met Arg Gln Gly Gly Ser Glu Lys Leu Val Phe Gly Lys Gly Thr Lys
        115                 120                 125

Leu Thr Val Asn Pro Tyr Ile Gln Asn Pro Glu Pro Ala Val Tyr Gln
130                 135                 140

Leu Lys Asp Pro Arg Ser Gln Asp Ser Thr Leu Cys Leu Phe Thr Asp
145                 150                 155                 160

Phe Asp Ser Gln Ile Asn Val Pro Lys Thr Met Glu Ser Gly Thr Phe
                165                 170                 175

Ile Thr Asp Lys Thr Val Leu Asp Met Lys Ala Met Asp Ser Lys Ser
            180                 185                 190

Asn Gly Ala Ile Ala Trp Ser Asn Gln Thr Ser Phe Thr Cys Gln Asp
        195                 200                 205

Ile Phe Lys Glu Thr Asn Ala Thr Tyr Pro Ser Ser Asp Val Pro Cys
    210                 215                 220

Asp Ala Thr Leu Thr Glu Lys Ser Phe Glu Thr Asp Met Asn Leu Asn
225                 230                 235                 240

Phe Gln Asn Leu Ser Val Met Gly Leu Arg Ile Leu Leu Leu Lys Val
                245                 250                 255

Ala Gly Phe Asn Leu Leu Met Thr Leu Arg Leu Trp Ser Ser
            260                 265                 270

<210> SEQ ID NO 41
<211> LENGTH: 270
<212> TYPE: PRT
<213> ORGANISM: Artificial Sequence
<220> FEATURE:
<223> OTHER INFORMATION: TCR3598_2 TCR alpha chain specific for HLA-DR4
      epitope NY-ESO-1 116-135

<400> SEQUENCE: 41

Met Asn Tyr Ser Pro Gly Leu Val Ser Leu Ile Leu Leu Leu Leu Gly
1               5                   10                  15

Arg Thr Arg Gly Asp Ser Val Thr Gln Met Glu Gly Pro Val Thr Leu
            20                  25                  30

Ser Glu Glu Ala Phe Leu Thr Ile Asn Cys Thr Tyr Thr Ala Thr Gly
        35                  40                  45

Tyr Pro Ser Leu Phe Trp Tyr Val Gln Tyr Pro Gly Glu Gly Leu Gln
    50                  55                  60

Leu Leu Leu Lys Ala Thr Lys Ala Asp Asp Lys Gly Ser Asn Lys Gly
65                  70                  75                  80

Phe Glu Ala Thr Tyr Arg Lys Glu Thr Thr Ser Phe His Leu Glu Lys
                85                  90                  95

Gly Ser Val Gln Val Ser Asp Ser Ala Val Tyr Phe Cys Ala Leu Arg
            100                 105                 110

Asp Ser Gly Gly Gly Ala Asp Gly Leu Thr Phe Gly Lys Gly Thr His

```
            115                 120                 125
Leu Ile Ile Gln Pro Tyr Ile Gln Asn Pro Glu Pro Ala Val Tyr Gln
130                 135                 140

Leu Lys Asp Pro Arg Ser Gln Asp Ser Thr Leu Cys Leu Phe Thr Asp
145                 150                 155                 160

Phe Asp Ser Gln Ile Asn Val Pro Lys Thr Met Glu Ser Gly Thr Phe
                165                 170                 175

Ile Thr Asp Lys Thr Val Leu Asp Met Lys Ala Met Asp Ser Lys Ser
            180                 185                 190

Asn Gly Ala Ile Ala Trp Ser Asn Gln Thr Ser Phe Thr Cys Gln Asp
            195                 200                 205

Ile Phe Lys Glu Thr Asn Ala Thr Tyr Pro Ser Ser Asp Val Pro Cys
        210                 215                 220

Asp Ala Thr Leu Thr Glu Lys Ser Phe Glu Thr Asp Met Asn Leu Asn
225                 230                 235                 240

Phe Gln Asn Leu Ser Val Met Gly Leu Arg Ile Leu Leu Leu Lys Val
                245                 250                 255

Ala Gly Phe Asn Leu Leu Met Thr Leu Arg Leu Trp Ser Ser
            260                 265                 270

<210> SEQ ID NO 42
<211> LENGTH: 269
<212> TYPE: PRT
<213> ORGANISM: Artificial Sequence
<220> FEATURE:
<223> OTHER INFORMATION: TCR5412 TCR alpha chain specific for HLA-DR4
      epitope NY-ESO-1 116-135

<400> SEQUENCE: 42

Met Leu Leu Leu Leu Val Pro Ala Phe Gln Val Ile Phe Thr Leu Gly
1               5                   10                  15

Gly Thr Arg Ala Gln Ser Val Thr Gln Leu Asp Ser Gln Val Pro Val
            20                  25                  30

Phe Glu Glu Ala Pro Val Glu Leu Arg Cys Asn Tyr Ser Ser Ser Val
        35                  40                  45

Ser Val Tyr Leu Phe Trp Tyr Val Gln Tyr Pro Asn Gln Gly Leu Gln
    50                  55                  60

Leu Leu Leu Lys Tyr Leu Ser Gly Ser Thr Leu Val Glu Ser Ile Asn
65                  70                  75                  80

Gly Phe Glu Ala Glu Phe Asn Lys Ser Gln Thr Ser Phe His Leu Arg
                85                  90                  95

Lys Pro Ser Val His Ile Ser Asp Thr Ala Glu Tyr Phe Cys Ala Val
            100                 105                 110

Thr Leu Asn Arg Asp Asp Lys Ile Ile Phe Gly Lys Gly Thr Arg Leu
        115                 120                 125

His Ile Leu Pro Asn Ile Gln Asn Pro Glu Pro Ala Val Tyr Gln Leu
130                 135                 140

Lys Asp Pro Arg Ser Gln Asp Ser Thr Leu Cys Leu Phe Thr Asp Phe
145                 150                 155                 160

Asp Ser Gln Ile Asn Val Pro Lys Thr Met Glu Ser Gly Thr Phe Ile
                165                 170                 175

Thr Asp Lys Thr Val Leu Asp Met Lys Ala Met Asp Ser Lys Ser Asn
            180                 185                 190

Gly Ala Ile Ala Trp Ser Asn Gln Thr Ser Phe Thr Cys Gln Asp Ile
        195                 200                 205
```

```
Phe Lys Glu Thr Asn Ala Thr Tyr Pro Ser Ser Asp Val Pro Cys Asp
    210                 215                 220

Ala Thr Leu Thr Glu Lys Ser Phe Glu Thr Asp Met Asn Leu Asn Phe
225                 230                 235                 240

Gln Asn Leu Ser Val Met Gly Leu Arg Ile Leu Leu Leu Lys Val Ala
                245                 250                 255

Gly Phe Asn Leu Leu Met Thr Leu Arg Leu Trp Ser Ser
                260                 265
```

<210> SEQ ID NO 43
<211> LENGTH: 270
<212> TYPE: PRT
<213> ORGANISM: Artificial Sequence
<220> FEATURE:
<223> OTHER INFORMATION: TCR5412_2 TCR alpha chain specific for HLA-DR4
      epitope NY-ESO-1 116-135

<400> SEQUENCE: 43

```
Met Leu Leu Leu Leu Val Pro Ala Phe Gln Val Ile Phe Thr Leu Gly
1               5                   10                  15

Gly Thr Arg Ala Gln Ser Val Thr Gln Leu Asp Ser Gln Val Pro Val
                20                  25                  30

Phe Glu Glu Ala Pro Val Glu Leu Arg Cys Asn Tyr Ser Ser Ser Val
            35                  40                  45

Ser Val Tyr Leu Phe Trp Tyr Val Gln Tyr Pro Asn Gln Gly Leu Gln
    50                  55                  60

Leu Leu Leu Lys Tyr Leu Ser Gly Ser Thr Leu Val Glu Ser Ile Asn
65                  70                  75                  80

Gly Phe Glu Ala Glu Phe Asn Lys Ser Gln Thr Ser Phe His Leu Arg
                85                  90                  95

Lys Pro Ser Val His Ile Ser Asp Thr Ala Glu Tyr Phe Cys Ala Val
                100                 105                 110

Thr Arg Asn Ser Gly Asn Thr Pro Leu Val Phe Gly Lys Gly Thr Arg
            115                 120                 125

Leu Ser Val Ile Ala Asn Ile Gln Asn Pro Glu Pro Ala Val Tyr Gln
130                 135                 140

Leu Lys Asp Pro Arg Ser Gln Asp Ser Thr Leu Cys Leu Phe Thr Asp
145                 150                 155                 160

Phe Asp Ser Gln Ile Asn Val Pro Lys Thr Met Glu Ser Gly Thr Phe
                165                 170                 175

Ile Thr Asp Lys Thr Val Leu Asp Met Lys Ala Met Asp Ser Lys Ser
            180                 185                 190

Asn Gly Ala Ile Ala Trp Ser Asn Gln Thr Ser Phe Thr Cys Gln Asp
        195                 200                 205

Ile Phe Lys Glu Thr Asn Ala Thr Tyr Pro Ser Ser Asp Val Pro Cys
    210                 215                 220

Asp Ala Thr Leu Thr Glu Lys Ser Phe Glu Thr Asp Met Asn Leu Asn
225                 230                 235                 240

Phe Gln Asn Leu Ser Val Met Gly Leu Arg Ile Leu Leu Leu Lys Val
                245                 250                 255

Ala Gly Phe Asn Leu Leu Met Thr Leu Arg Leu Trp Ser Ser
                260                 265                 270
```

<210> SEQ ID NO 44
<211> LENGTH: 269
<212> TYPE: PRT
<213> ORGANISM: Artificial Sequence
<220> FEATURE:
<223> OTHER INFORMATION: TCR5412_3 TCR alpha chain specific for HLA-DR4
    epitope NY-ESO-1 116-135

<400> SEQUENCE: 44

Met Leu Leu Glu His Leu Leu Ile Ile Leu Trp Met Gln Leu Thr Trp
1               5                   10                  15

Val Ser Gly Gln Gln Leu Asn Gln Ser Pro Gln Ser Met Phe Ile Gln
            20                  25                  30

Glu Gly Glu Asp Val Ser Met Asn Cys Thr Ser Ser Ile Phe Asn
        35                  40                  45

Thr Trp Leu Trp Tyr Lys Gln Asp Pro Gly Glu Gly Pro Val Leu Leu
    50                  55                  60

Ile Ala Leu Tyr Lys Ala Gly Glu Leu Thr Ser Asn Gly Arg Leu Thr
65                  70                  75                  80

Ala Gln Phe Gly Ile Thr Arg Lys Asp Ser Phe Leu Asn Ile Ser Ala
                85                  90                  95

Ser Ile Pro Ser Asp Val Gly Ile Tyr Phe Cys Ala Gly Gln Gln Asn
            100                 105                 110

Ser Gly Gly Ser Asn Tyr Lys Leu Thr Phe Gly Lys Gly Thr Leu Leu
        115                 120                 125

Thr Val Asn Pro Asn Ile Gln Asn Pro Glu Pro Ala Val Tyr Gln Leu
    130                 135                 140

Lys Asp Pro Arg Ser Gln Asp Ser Thr Leu Cys Leu Phe Thr Asp Phe
145                 150                 155                 160

Asp Ser Gln Ile Asn Val Pro Lys Thr Met Glu Ser Gly Thr Phe Ile
                165                 170                 175

Thr Asp Lys Thr Val Leu Asp Met Lys Ala Met Asp Ser Lys Ser Asn
            180                 185                 190

Gly Ala Ile Ala Trp Ser Asn Gln Thr Ser Phe Thr Cys Gln Asp Ile
        195                 200                 205

Phe Lys Glu Thr Asn Ala Thr Tyr Pro Ser Ser Asp Val Pro Cys Asp
    210                 215                 220

Ala Thr Leu Thr Glu Lys Ser Phe Glu Thr Asp Met Asn Leu Asn Phe
225                 230                 235                 240

Gln Asn Leu Ser Val Met Gly Leu Arg Ile Leu Leu Leu Lys Val Ala
                245                 250                 255

Gly Phe Asn Leu Leu Met Thr Leu Arg Leu Trp Ser Ser
            260                 265

<210> SEQ ID NO 45
<211> LENGTH: 268
<212> TYPE: PRT
<213> ORGANISM: Artificial Sequence
<220> FEATURE:
<223> OTHER INFORMATION: TCR3600 TCR alpha chain specific for HLA-DR4
    epitope NY-ESO-1 116-135

<400> SEQUENCE: 45

Met Val Lys Ile Arg Gln Phe Leu Leu Ala Ile Leu Trp Leu Gln Leu
1               5                   10                  15

Ser Cys Val Ser Ala Ala Lys Asn Glu Val Glu Gln Ser Pro Gln Asn
            20                  25                  30

Leu Thr Ala Gln Glu Gly Glu Phe Ile Thr Ile Asn Cys Ser Tyr Ser
        35                  40                  45

Val Gly Ile Ser Ala Leu His Trp Leu Gln Gln His Pro Gly Gly Gly
    50                  55                  60

```
Ile Val Ser Leu Phe Met Leu Ser Ser Gly Lys Lys His Gly Arg
65                  70                  75                  80

Leu Ile Ala Thr Ile Asn Ile Gln Glu Lys His Ser Ser Leu His Ile
                85                  90                  95

Thr Ala Ser His Pro Arg Asp Ser Ala Val Tyr Ile Cys Ala Val Pro
            100                 105                 110

Asn Ser Gly Asn Thr Pro Leu Val Phe Gly Lys Gly Thr Arg Leu Ser
            115                 120                 125

Val Ile Ala Asn Ile Gln Asn Pro Glu Pro Ala Val Tyr Gln Leu Lys
130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
            165                 170                 175

Asp Lys Thr Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
            195                 200                 205

Lys Glu Thr Asn Ala Thr Tyr Pro Ser Ser Asp Val Pro Cys Asp Ala
            210                 215                 220

Thr Leu Thr Glu Lys Ser Phe Glu Thr Asp Met Asn Leu Asn Phe Gln
225                 230                 235                 240

Asn Leu Ser Val Met Gly Leu Arg Ile Leu Leu Leu Lys Val Ala Gly
                245                 250                 255

Phe Asn Leu Leu Met Thr Leu Arg Leu Trp Ser Ser
            260                 265

<210> SEQ ID NO 46
<211> LENGTH: 268
<212> TYPE: PRT
<213> ORGANISM: Artificial Sequence
<220> FEATURE:
<223> OTHER INFORMATION: TCR5712 TCR alpha chain specific for HLA-DR4
      epitope NY-ESO-1 116-135

<400> SEQUENCE: 46

Met Val Lys Ile Arg Gln Phe Leu Leu Ala Ile Leu Trp Leu Gln Leu
1               5                   10                  15

Ser Cys Val Ser Ala Ala Lys Asn Glu Val Glu Gln Ser Pro Gln Asn
                20                  25                  30

Leu Thr Ala Gln Glu Gly Glu Phe Ile Thr Ile Asn Cys Ser Tyr Ser
            35                  40                  45

Val Gly Ile Ser Ala Leu His Trp Leu Gln Gln His Pro Gly Gly Gly
        50                  55                  60

Ile Val Ser Leu Phe Met Leu Ser Ser Gly Lys Lys His Gly Arg
65                  70                  75                  80

Leu Ile Ala Thr Ile Asn Ile Gln Glu Lys His Ser Ser Leu His Ile
                85                  90                  95

Thr Ala Ser His Pro Arg Asp Ser Ala Val Tyr Ile Cys Ala Val Pro
            100                 105                 110

Asn Ser Gly Asn Thr Pro Leu Val Phe Gly Lys Gly Thr Arg Leu Ser
            115                 120                 125

Val Ile Ala Asn Ile Gln Asn Pro Glu Pro Ala Val Tyr Gln Leu Lys
130                 135                 140

Asp Pro Arg Ser Gln Asp Ser Thr Leu Cys Leu Phe Thr Asp Phe Asp
```

```
                145                 150                 155                 160
Ser Gln Ile Asn Val Pro Lys Thr Met Glu Ser Gly Thr Phe Ile Thr
                    165                 170                 175

Asp Lys Thr Val Leu Asp Met Lys Ala Met Asp Ser Lys Ser Asn Gly
                    180                 185                 190

Ala Ile Ala Trp Ser Asn Gln Thr Ser Phe Thr Cys Gln Asp Ile Phe
                    195                 200                 205

Lys Glu Thr Asn Ala Thr Tyr Pro Ser Ser Asp Val Pro Cys Asp Ala
                    210                 215                 220

Thr Leu Thr Glu Lys Ser Phe Glu Thr Asp Met Asn Leu Asn Phe Gln
225                 230                 235                 240

Asn Leu Ser Val Met Gly Leu Arg Ile Leu Leu Leu Lys Val Ala Gly
                    245                 250                 255

Phe Asn Leu Leu Met Thr Leu Arg Leu Trp Ser Ser
                    260                 265

<210> SEQ ID NO 47
<211> LENGTH: 268
<212> TYPE: PRT
<213> ORGANISM: Artificial Sequence
<220> FEATURE:
<223> OTHER INFORMATION: TCR5415 TCR alpha chain specific for HLA-DR4
      epitope NY-ESO-1 116-135

<400> SEQUENCE: 47

Met Val Lys Ile Arg Gln Phe Leu Leu Ala Ile Leu Trp Leu Gln Leu
1                   5                   10                  15

Ser Cys Val Ser Ala Ala Lys Asn Glu Val Glu Gln Ser Pro Gln Asn
                    20                  25                  30

Leu Thr Ala Gln Glu Gly Glu Phe Ile Thr Ile Asn Cys Ser Tyr Ser
                    35                  40                  45

Val Gly Ile Ser Ala Leu His Trp Leu Gln Gln His Pro Gly Gly Gly
                50                  55                  60

Ile Val Ser Leu Phe Met Leu Ser Ser Gly Lys Lys Lys His Gly Arg
65                  70                  75                  80

Leu Ile Ala Thr Ile Asn Ile Gln Glu Lys His Ser Ser Leu His Ile
                    85                  90                  95

Thr Ala Ser His Pro Arg Asp Ser Ala Val Tyr Ile Cys Ala Val Pro
                    100                 105                 110

Asn Ser Gly Asn Thr Pro Leu Val Phe Gly Lys Gly Thr Arg Leu Ser
                    115                 120                 125

Val Ile Ala Asn Ile Gln Asn Pro Glu Pro Ala Val Tyr Gln Leu Lys
                    130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                    165                 170                 175

Asp Lys Thr Val Leu Asp Met Lys Ala Met Asp Ser Lys Ser Asn Gly
                    180                 185                 190

Ala Ile Ala Trp Ser Asn Gln Thr Ser Phe Thr Cys Gln Asp Ile Phe
                    195                 200                 205

Lys Glu Thr Asn Ala Thr Tyr Pro Ser Ser Asp Val Pro Cys Asp Ala
                    210                 215                 220

Thr Leu Thr Glu Lys Ser Phe Glu Thr Asp Met Asn Leu Asn Phe Gln
225                 230                 235                 240
```

-continued

```
Asn Leu Ser Val Met Gly Leu Arg Ile Leu Leu Lys Val Ala Gly
                245                 250                 255

Phe Asn Leu Leu Met Thr Leu Arg Leu Trp Ser Ser
            260                 265
```

<210> SEQ ID NO 48
<211> LENGTH: 269
<212> TYPE: PRT
<213> ORGANISM: Artificial Sequence
<220> FEATURE:
<223> OTHER INFORMATION: TCR5713 TCR alpha chain specific for HLA-DR4
      epitope NY-ESO-1 116-135

<400> SEQUENCE: 48

```
Met Lys Thr Phe Ala Gly Phe Ser Phe Leu Phe Leu Trp Leu Gln Leu
1               5                   10                  15

Asp Cys Met Ser Arg Gly Glu Asp Val Glu Gln Ser Leu Phe Leu Ser
            20                  25                  30

Val Arg Glu Gly Asp Ser Ser Val Ile Asn Cys Thr Tyr Thr Asp Ser
        35                  40                  45

Ser Ser Thr Tyr Leu Tyr Trp Tyr Lys Gln Glu Pro Gly Ala Gly Leu
    50                  55                  60

Gln Leu Leu Thr Tyr Ile Phe Ser Asn Met Asp Met Lys Gln Asp Gln
65                  70                  75                  80

Arg Leu Thr Val Leu Leu Asn Lys Lys Asp Lys His Leu Ser Leu Arg
                85                  90                  95

Ile Ala Asp Thr Gln Thr Gly Asp Ser Ala Ile Tyr Phe Cys Ala Glu
            100                 105                 110

Ala Asn Gln Ala Gly Thr Ala Leu Ile Phe Gly Lys Gly Thr Thr Leu
        115                 120                 125

Ser Val Ser Ser Asn Ile Gln Asn Pro Glu Pro Ala Val Tyr Gln Leu
    130                 135                 140

Lys Asp Pro Arg Ser Gln Asp Ser Thr Leu Cys Leu Phe Thr Asp Phe
145                 150                 155                 160

Asp Ser Gln Ile Asn Val Pro Lys Thr Met Glu Ser Gly Thr Phe Ile
                165                 170                 175

Thr Asp Lys Thr Val Leu Asp Met Lys Ala Met Asp Ser Lys Ser Asn
            180                 185                 190

Gly Ala Ile Ala Trp Ser Asn Gln Thr Ser Phe Thr Cys Gln Asp Ile
        195                 200                 205

Phe Lys Glu Thr Asn Ala Thr Tyr Pro Ser Ser Asp Val Pro Cys Asp
    210                 215                 220

Ala Thr Leu Thr Glu Lys Ser Phe Glu Thr Asp Met Asn Leu Asn Phe
225                 230                 235                 240

Gln Asn Leu Ser Val Met Gly Leu Arg Ile Leu Leu Leu Lys Val Ala
                245                 250                 255

Gly Phe Asn Leu Leu Met Thr Leu Arg Leu Trp Ser Ser
            260                 265
```

<210> SEQ ID NO 49
<211> LENGTH: 813
<212> TYPE: DNA
<213> ORGANISM: Artificial Sequence
<220> FEATURE:
<223> OTHER INFORMATION: TCR3598 TCR alpha chain specific for HLA-DR4
      epitope NY-ESO-1 116-135

<400> SEQUENCE: 49

```
atgatgaagt ccctgcgggt gctgctcgtg atcctgtggc tgcagctgag ctgggtgtgg      60
tcccagcaga agaggtggac acaggaccca ggccctctga gcgtgccaga gggcgctatc     120
gtgtccctga attgcaccta cagcaacagc gccttccagt acttcatgtg gtatcggcag     180
tacagccgga agggccccga gctgctgatg tacacctact ccagcggcaa caaagaggac     240
ggccggttca cagcccaggt ggacaagagc agcaagtaca tctccctgtt catccgggac     300
agccagccca cgacagcgc cacatatctg tgcgccatga acagggcgg ctccgagaag     360 ctggtgttcg gcaagggcac aaagctgacc gtgaacccct acatccagaa ccccgagccc     420
gccgtgtacc agctgaagga ccctagaagc aggacagca cctgtgcct gttcaccgac     480 ttcgacagcc agatcaacgt gcccaagacc atggaaagcg gcaccttcat caccgacaag     540
accgtgctgg acatgaaggc catggacagc aagagcaacg cgccattgc ctggtccaac     600 cagaccagct tcacatgcca ggacatcttc aaagagacaa cgccaccta ccccagcagc     660 gacgtgccct gtgatgccac cctgaccgag aagtctttcg agacagacat gaacctgaac     720
ttccagaacc tgagcgtgat gggcctgaga atcctgctgc tgaaagtggc cggattcaac     780
ctgctgatga ccctgcggct gtggtccagc tga                                 813

<210> SEQ ID NO 50
<211> LENGTH: 813
<212> TYPE: DNA
<213> ORGANISM: Artificial Sequence
<220> FEATURE:
<223> OTHER INFORMATION: TCR3598_2 TCR alpha chain specific for HLA-DR4
      epitope NY-ESO-1 116-135

<400> SEQUENCE: 50
atgaactact ctcccggcct ggtgtctctg attctgctgc tgctgggccg gaccagaggc      60
gattctgtga cccagatgga aggccccgtg accctgagcg aggaagcctt cctgaccatc     120
aattgcacct acaccgccac cggctacccc agcctgtttt ggtacgtgca gtaccccggc     180
gagggcctgc agctgctgct gaaagccacc aaggccgacg acaagggcag caacaagggc     240
ttcgaggcca cctaccggaa agagacaacc agcttccacc tggaaaaggg cagcgtgcag     300
gtgtccgact ccgccgtgta tttctgcgcc ctgagagatt ctggcggcgg agccgatggc     360
ctgacctttg gcaagggcac acacctgatc atccagccct acatccagaa ccccgagcct     420
gccgtgtacc agctgaagga ccctagaagc aggacagca cctgtgcct gttcaccgac     480 ttcgacagcc agatcaacgt gcccaagacc atggaaagcg gcaccttcat caccgacaag     540
accgtgctgg acatgaaggc catggacagc aagagcaacg cgccattgc ctggtccaac     600 cagaccagct tcacatgcca ggacatcttc aaagagacta acgccacata ccccagcagc     660
gacgtgccct gtgatgccac cctgaccgag aagtctttcg agacagacat gaacctgaac     720
ttccagaacc tgagcgtgat gggcctgaga atcctgctgc tgaaggtggc cggcttcaac     780
ctgctgatga ccctgagact gtggtccagc tga                                 813

<210> SEQ ID NO 51
<211> LENGTH: 810
<212> TYPE: DNA
<213> ORGANISM: Artificial Sequence
<220> FEATURE:
<223> OTHER INFORMATION: TCR5412 TCR alpha chain specific for HLA-DR4
      epitope NY-ESO-1 116-135

<400> SEQUENCE: 51
atgctcctgc tgctggtgcc tgccttccaa gtgatcttca ccctgggcgg caccagagcc      60
```

```
cagagcgtga cacagctgga tagccaggtg cccgtgttcg aagaggcccc tgtggaactg      120
cggtgcaact actccagcag cgtgtccgtg tacctgtttt ggtacgtgca gtaccccaac      180
cagggcctgc agctgctgct gaagtacctg agcggctcca ccctggtgga atccatcaac      240
ggcttcgagg ccgagttcaa caagagccag accagcttcc acctgagaaa gcccagcgtg      300
cacatcagcg ataccgccga gtacttctgc gccgtgaccc tgaaccggga cgacaagatc      360
atcttcggca agggcaccag actgcacatc ctgcccaaca tccagaaccc cgagcccgcc      420
gtgtaccagc tgaaggaccc tagaagccag atagcaccc tgtgtctgtt caccgacttc      480
gacagccaga tcaacgtgcc caagaccatg aaagcggca ccttcatcac cgacaagaca      540
gtgctggaca tgaaggccat ggacagcaag agcaacggcg ccattgcctg gtccaaccag      600
acaagcttca catgccagga catcttcaaa gagacaaacg ccacctaccc cagctccgac      660
gtgccctgtg atgccaccct gaccgagaag tccttcgaga cagacatgaa cctgaatttc      720 cagaaccctga gcgtgatggg cctgcggatc ctgctgctga agtggccgg cttcaacctg      780 ctgatgaccc tgagactgtg gtccagctga                                      810
```

<210> SEQ ID NO 52
<211> LENGTH: 813
<212> TYPE: DNA
<213> ORGANISM: Artificial Sequence
<220> FEATURE:
<223> OTHER INFORMATION: TCR5412_2 TCR alpha chain specific for HLA-DR4
      epitope NY-ESO-1 116-135

<400> SEQUENCE: 52

```
atgctcctgc tgctggtgcc tgccttccaa gtgatcttca ccctgggcgg caccagggcc      60
cagtctgtga cacagctgga tagccaggtg cccgtgttcg aagaggcccc tgtggaactg     120
cggtgcaact actccagcag cgtgtccgtg tacctgtttt ggtacgtgca gtaccccaac     180
cagggcctgc agctgctgct gaagtacctg agcggctcca ccctggtgga atccatcaac     240
ggcttcgagg ccgagttcaa caagagccag accagcttcc atctgcggaa gcccagcgtg     300
cacatcagcg ataccgccga gtacttctgt gccgtgaccc ggaactccgg caacaccct     360 ctggtgtttg gcaagggcac acggctgagc gtgatcgcca atatccagaa ccccgagcct     420
gccgtgtacc agctgaagga ccccagaagc caggatagca ccctgtgcct gttcaccgac     480
ttcgacagcc agatcaatgt gcccaagacc atggaaagcg gcaccttcat caccgacaag     540
accgtgctgg acatgaaggc catggacagc aagagcaacg gcgccattgc ctggtccaac     600
cagacaagct tcacatgcca ggacatcttc aaagagacaa acgccaccta ccccagctcc     660
gacgtgccct gtgatgccac cctgaccgag aagtccttcg agacagacat gaacctgaac     720
ttccagaacc tgtccgtgat gggcctgcgg atcctgctgc tgaaagtggc cggcttcaac     780
ctgctgatga ccctgagact gtggtccagc tga                                 813
```

<210> SEQ ID NO 53
<211> LENGTH: 810
<212> TYPE: DNA
<213> ORGANISM: Artificial Sequence
<220> FEATURE:
<223> OTHER INFORMATION: TCR5412_3 TCR alpha chain specific for HLA-DR4
      epitope NY-ESO-1 116-135

<400> SEQUENCE: 53

```
atgctgctgg aacatctgct gatcatcctg tggatgcagc tgacctgggt gtccggccag      60
```

```
cagctgaatc agagccccca gagcatgttc atccaggaag gcgaggacgt gtccatgaac    120
tgcaccagca gcagcatctt caatacctgg ctgtggtaca agcaggaccc cggcgaagga    180
cccgtgctgc tgatcgccct gtacaaagcc ggcgagctga ccagcaatgg caggctgaca    240
gcccagttcg gcattacccg gaaggacagc ttcctgaaca tcagcgcctc catccccagc    300
gacgtgggca tctatttctg cgccggacag cagaactccg gcggctccaa ctacaagctg    360
accttcggca agggcacact gctgacagtg aaccccaaca tccagaaccc cgagcccgcc    420
gtgtaccagc tgaaggaccc tagaagccag acagcaccc tgtgcctgtt caccgacttc    480
gacagccaga tcaacgtgcc caagaccatg gaaagcggca ccttcatcac cgacaagacc    540
gtgctggaca tgaaggccat ggacagcaag agcaacggcg caatcgcctg gtccaaccag    600
accagcttca tgccaggca tcttcaaa gagacaaacg ccacctaccc cagctccgac    660
gtgccctgtg atgccaccct gaccgagaag tccttcgaga cagacatgaa cctgaacttc    720
cagaatctga gcgtgatggg cctgcgcatc ctgctgctga aggtggccgg ctttaacctg    780
ctgatgaccc tgcggctgtg gtccagctga                                    810
```

<210> SEQ ID NO 54
<211> LENGTH: 807
<212> TYPE: DNA
<213> ORGANISM: Artificial Sequence
<220> FEATURE:
<223> OTHER INFORMATION: TCR3600 TCR alpha chain specific for HLA-DR4
      epitope NY-ESO-1 116-135

<400> SEQUENCE: 54

```
atggtcaaaa tccggcagtt cctgctggcc atcctgtggc tgcagctgag ctgtgtgtcc     60
gccgccaaga cgaggtgga acagagcccc cagaacctga ccgctcagga aggcgagttc    120
atcaccatca actgcagcta cagcgtgggc atcagcgccc tgcattggct gcagcagcat    180
cctggcggag gcatcgtgtc tctgttcatg ctgagcagcg aaagaagaa gcacggccgg    240 ctgatcgcca caatcaacat ccaggaaaag cacagcagcc tgcacatcac cgccagccac    300
cctagagaca cgccgtgta catctgcgcc gtgcccaata gcggcaacac ccctctggtg    360
ttcggcaagg gcaccagact gagcgtgatc gccaatatcc agaaccccga gctgccgtg    420 taccagctga aggaccctag aagccaggac agcaccctgt gcctgttcac cgacttcgac    480
agccagatca acgtgcccaa gaccatggaa agcggcacct tcatcaccga caagaccgtg    540
ctggacatga aggccatgga cagcaagagc aacggcgcca ttgcctggtc aaccagacc    600 agcttcacat gccaggacat cttcaaagag acaaacgcca cctacccag cagcgacgtg    660 ccctgtgatg ccaccctgac cgagaagtct ttcgagacag acatgaacct gaacttccag    720
aatctgtccg tgatgggcct gagaatcctg ctgctgaaag tggccggatt caacctgctg    780
atgaccctgc ggctgtggtc cagctga                                       807
```

<210> SEQ ID NO 55
<211> LENGTH: 807
<212> TYPE: DNA
<213> ORGANISM: Artificial Sequence
<220> FEATURE:
<223> OTHER INFORMATION: TCR5712 TCR alpha chain specific for HLA-DR4
      epitope NY-ESO-1 116-135

<400> SEQUENCE: 55

```
atggtcaaaa tccggcagtt cctgctggcc atcctgtggc tgcagctgag ctgtgtgtcc     60
gccgccaaga cgaggtgga acagagcccc cagaacctga ccgctcagga aggcgagttc    120
```

```
atcaccatca actgcagcta cagcgtgggc atcagcgccc tgcattggct gcagcagcat      180
cctggcggag gcatcgtgtc tctgttcatg ctgagcagcg aaagaagaa gcacggccgg      240 ctgatcgcca caatcaacat ccaggaaaag cacagcagcc tgcacatcac cgccagccac      300
cctagagaca gcgccgtgta catctgcgcc gtgcccaata gcggcaacac ccctctggtg      360
ttcggcaagg gcaccagact gagcgtgatc gccaatatcc agaaccccga gcctgccgtg      420
taccagctga aggaccctag aagccaggac agcaccctgt gcctgttcac cgacttcgac      480
agccagatca acgtgcccaa gaccatggaa agcggcacct tcatcaccga caagaccgtg      540
ctggacatga aggccatgga cagcaagagc aacggcgcca ttgcctggtc aaccagacc      600 agcttcacat gccaggacat cttcaaagag acaaacgcca cctaccccag cagcgacgtg      660
ccctgtgatg ccaccctgac cgagaagtct ttcgagacag acatgaacct gaacttccag      720
aatctgtccg tgatgggcct gagaatcctg ctgctgaaag tggccggatt caacctgctg      780
atgaccctgc ggctgtggtc cagctga                                         807
```

<210> SEQ ID NO 56
<211> LENGTH: 807
<212> TYPE: DNA
<213> ORGANISM: Artificial Sequence
<220> FEATURE:
<223> OTHER INFORMATION: TCR5415 TCR alpha chain specific for HLA-DR4
      epitope NY-ESO-1 116-135

<400> SEQUENCE: 56

```
atggtcaaaa tccggcagtt cctgctggcc atcctgtggc tgcagctgag ctgtgtgtcc       60
gccgccaaga cgaggtgga acagagcccc cagaacctga ccgctcagga aggcgagttc      120
atcaccatca actgcagcta cagcgtgggc atcagcgccc tgcattggct gcagcagcat      180
cctggcggag gcatcgtgtc tctgttcatg ctgagcagcg aaagaagaa gcacggccgg      240 ctgatcgcca caatcaacat ccaggaaaag cacagcagcc tgcacatcac cgccagccac      300
cctagagaca gcgccgtgta catctgcgcc gtgcccaata gcggcaacac ccctctggtg      360
ttcggcaagg gcaccagact gagcgtgatc gccaatatcc agaaccccga gcctgccgtg      420
taccagctga aggaccctag aagccaggac agcaccctgt gcctgttcac cgacttcgac      480
agccagatca acgtgcccaa gaccatggaa agcggcacct tcatcaccga caagaccgtg      540
ctggacatga aggccatgga cagcaagagc aacggcgcca ttgcctggtc aaccagacc      600 agcttcacat gccaggacat cttcaaagag acaaacgcca cctaccccag cagcgacgtg      660
ccctgtgatg ccaccctgac cgagaagtct ttcgagacag acatgaacct gaacttccag      720
aatctgtccg tgatgggcct gagaatcctg ctgctgaaag tggccggatt caacctgctg      780
atgaccctgc ggctgtggtc cagctga                                         807
```

<210> SEQ ID NO 57
<211> LENGTH: 810
<212> TYPE: DNA
<213> ORGANISM: Artificial Sequence
<220> FEATURE:
<223> OTHER INFORMATION: TCR5713 TCR alpha chain specific for HLA-DR4
      epitope NY-ESO-1 116-135

<400> SEQUENCE: 57

```
atgaagacct cgccggcctt cagcttcctg ttcctgtggc tgcagctgga ctgcatgagc       60
agaggcgagg acgtggaaca gagcctgttt ctgagcgtgc gcgagggcga cagcagcgtg      120
```

```
atcaattgca cctacaccga cagctccagc acatacctgt actggtataa gcaggaaccc      180
ggcgctggcc tgcagctgct gacctacatc ttctccaaca tggacatgaa gcaggaccag      240
cggctgacag tgctgctgaa caagaaggac aagcacctga gcctgcggat cgccgatacc      300
cagacaggcg actccgccat ctatttctgc gccgaggcca atcaggccgg caccgccctg      360
atctttggca agggcacaac actgagcgtg tccagcaaca tccagaaccc cgagcccgcc      420
gtgtaccagc tgaaggaccc tagaagccag acagcaccc tgtgcctgtt caccgacttc      480
gacagccaga tcaacgtgcc caagaccatg gaaagcggca ccttcatcac cgacaagact      540
gtgctggata tgaaggccat ggacagcaag agcaacggcg ccattgcctg gtccaaccag      600
accagcttca catgccagga catcttcaaa gagacaaacg ccacctaccc cagcagcgac      660
gtgccctgtg atgccaccct gaccgagaag tctttcgaga cagacatgaa cctgaacttc      720
cagaacctga gcgtgatggg cctgagaatc ctgctgctga aggtggccgg cttcaacctg      780
ctgatgaccc tgagactgtg gtccagctga                                      810
```

```
<210> SEQ ID NO 58
<211> LENGTH: 133
<212> TYPE: PRT
<213> ORGANISM: Homo sapiens
<220> FEATURE:
<223> OTHER INFORMATION: TCR3598 TCR beta chain specific for HLA-DR4
      epitope NY-ESO-1 116-135 , variable region

<400> SEQUENCE: 58

Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
            100                 105                 110

Ser Ser Gly Gln Gly Ala Gly Thr Gln Tyr Phe Gly Pro Gly Thr Arg
        115                 120                 125

Leu Leu Val Leu Glu
    130
```

```
<210> SEQ ID NO 59
<211> LENGTH: 135
<212> TYPE: PRT
<213> ORGANISM: Homo sapiens
<220> FEATURE:
<223> OTHER INFORMATION: TCR3598_2 TCR beta chain specific for HLA-DR4
      epitope NY-ESO-1 116-135 , variable region

<400> SEQUENCE: 59

Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30
```

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
 50                  55                  60

Leu Val Ser Phe Tyr Asn Asn Glu Ile Ser Glu Lys Ser Glu Ile Phe
 65                  70                  75                  80

Asp Asp Gln Phe Ser Val Glu Arg Pro Asp Gly Ser Asn Phe Thr Leu
                 85                  90                  95

Lys Ile Arg Ser Thr Lys Leu Glu Asp Ser Ala Met Tyr Phe Cys Ala
                100                 105                 110

Ser Ser Val Met Thr Gly Leu Asn Thr Glu Ala Phe Phe Gly Gln Gly
            115                 120                 125

Thr Arg Leu Thr Val Val Glu
    130                 135

<210> SEQ ID NO 60
<211> LENGTH: 134
<212> TYPE: PRT
<213> ORGANISM: Homo sapiens
<220> FEATURE:
<223> OTHER INFORMATION: TCR5412 TCR beta chain specific for HLA-DR4
      epitope NY-ESO-1 116-135 , variable region

<400> SEQUENCE: 60

Met Gly Thr Ser Leu Leu Cys Trp Met Ala Leu Cys Leu Leu Gly Ala
 1               5                  10                  15

Asp His Ala Asp Thr Gly Val Ser Gln Asp Pro Arg His Lys Ile Thr
                20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
 50                  55                  60

Leu Thr Tyr Phe Gln Asn Glu Ala Gln Leu Glu Lys Ser Arg Leu Leu
 65                  70                  75                  80

Ser Asp Arg Phe Ser Ala Glu Arg Pro Lys Gly Ser Phe Ser Thr Leu
                 85                  90                  95

Glu Ile Gln Arg Thr Glu Gln Gly Asp Ser Ala Met Tyr Leu Cys Ala
                100                 105                 110

Ser Ser Leu Asp Arg Pro Tyr Asn Glu Gln Phe Phe Gly Pro Gly Thr
            115                 120                 125

Arg Leu Thr Val Leu Glu
    130

<210> SEQ ID NO 61
<211> LENGTH: 135
<212> TYPE: PRT
<213> ORGANISM: Homo sapiens
<220> FEATURE:
<223> OTHER INFORMATION: TCR5412_2 TCR beta chain specific for HLA-DR4
      epitope NY-ESO-1 116-135 , variable region

<400> SEQUENCE: 61

Met Asp Ser Trp Thr Phe Cys Cys Val Ser Leu Cys Ile Leu Val Ala
 1               5                  10                  15

Lys His Thr Asp Ala Gly Val Ile Gln Ser Pro Arg His Glu Val Thr
                20                  25                  30

Glu Met Gly Gln Glu Val Thr Leu Arg Cys Lys Pro Ile Ser Gly His
        35                  40                  45

```
Asn Ser Leu Phe Trp Tyr Arg Gln Thr Met Met Arg Gly Leu Glu Leu
 50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
                100                 105                 110

Ser Ser Phe Leu Ala Ser Val Gly Tyr Glu Gln Tyr Phe Gly Pro Gly
                115                 120                 125

Thr Arg Leu Thr Val Thr Glu
130                 135

<210> SEQ ID NO 62
<211> LENGTH: 132
<212> TYPE: PRT
<213> ORGANISM: Homo sapiens
<220> FEATURE:
<223> OTHER INFORMATION: TCR5412_3 TCR beta chain specific for HLA-DR4
      epitope NY-ESO-1 116-135 , variable region

<400> SEQUENCE: 62

Met Asp Thr Arg Val Leu Cys Cys Ala Val Ile Cys Leu Leu Gly Ala
1               5                   10                  15

Gly Leu Ser Asn Ala Gly Val Met Gln Asn Pro Arg His Leu Val Arg
                20                  25                  30

Arg Arg Gly Gln Glu Ala Arg Leu Arg Cys Ser Pro Met Lys Gly His
                35                  40                  45

Ser His Val Tyr Trp Tyr Arg Gln Leu Pro Glu Glu Gly Leu Lys Phe
 50                  55                  60

Met Val Tyr Leu Gln Lys Glu Asn Ile Ile Asp Glu Ser Gly Met Pro
65                  70                  75                  80

Lys Glu Arg Phe Ser Ala Glu Phe Pro Lys Glu Gly Pro Ser Ile Leu
                85                  90                  95

Arg Ile Gln Gln Val Val Arg Gly Asp Ser Ala Ala Tyr Phe Cys Ala
                100                 105                 110

Ser Ser Pro Pro Leu Gly Glu Gln Tyr Phe Gly Pro Gly Thr Arg Leu
                115                 120                 125

Thr Val Thr Glu
130

<210> SEQ ID NO 63
<211> LENGTH: 131
<212> TYPE: PRT
<213> ORGANISM: Homo sapiens
<220> FEATURE:
<223> OTHER INFORMATION: TCR3600 TCR beta chain specific for HLA-DR4
      epitope NY-ESO-1 116-135 , variable region

<400> SEQUENCE: 63

Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
                20                  25                  30

Gln Met Gly Gln Glu Val Ile Leu Arg Cys Val Pro Ile Ser Asn His
                35                  40                  45

Leu Tyr Phe Tyr Trp Tyr Arg Gln Ile Leu Gly Gln Lys Val Glu Phe
 50                  55                  60
```

```
Leu Val Ser Phe Tyr Asn Asn Glu Ile Ser Glu Lys Ser Glu Ile Phe
 65                  70                  75                  80

Asp Asp Gln Phe Ser Val Glu Arg Pro Asp Gly Ser Asn Phe Thr Leu
                 85                  90                  95

Lys Ile Arg Ser Thr Lys Leu Glu Asp Ser Ala Met Tyr Phe Cys Ala
            100                 105                 110

Ser Ser Val Ile Tyr Glu Gln Tyr Phe Gly Pro Gly Thr Arg Leu Thr
        115                 120                 125

Val Thr Glu
    130

<210> SEQ ID NO 64
<211> LENGTH: 131
<212> TYPE: PRT
<213> ORGANISM: Homo sapiens
<220> FEATURE:
<223> OTHER INFORMATION: TCR5712 TCR beta chain specific for HLA-DR4
      epitope NY-ESO-1 116-135 , variable region

<400> SEQUENCE: 64

Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
 65                  70                  75                  80

Asp Asp Gln Phe Ser Val Glu Arg Pro Asp Gly Ser Asn Phe Thr Leu
                 85                  90                  95

Lys Ile Arg Ser Thr Lys Leu Glu Asp Ser Ala Met Tyr Phe Cys Ala
            100                 105                 110

Ser Ser Ile Ile Tyr Glu Gln Tyr Phe Gly Pro Gly Thr Arg Leu Thr
        115                 120                 125

Val Thr Glu
    130

<210> SEQ ID NO 65
<211> LENGTH: 131
<212> TYPE: PRT
<213> ORGANISM: Homo sapiens
<220> FEATURE:
<223> OTHER INFORMATION: TCR5415 TCR beta chain specific for HLA-DR4
      epitope NY-ESO-1 116-135 , variable region

<400> SEQUENCE: 65

Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
 65                  70                  75                  80
```

Asp Asp Gln Phe Ser Val Glu Arg Pro Asp Gly Ser Asn Phe Thr Leu
            85                  90                  95

Lys Ile Arg Ser Thr Lys Leu Glu Asp Ser Ala Met Tyr Phe Cys Ala
            100                 105                 110

Ser Ser Val Tyr Tyr Glu Gln Tyr Phe Gly Pro Gly Thr Arg Leu Thr
            115                 120                 125

Val Thr Glu
    130

<210> SEQ ID NO 66
<211> LENGTH: 136
<212> TYPE: PRT
<213> ORGANISM: Homo sapiens
<220> FEATURE:
<223> OTHER INFORMATION: TCR5713 TCR beta chain specific for HLA-DR4
      epitope NY-ESO-1 116-135 , variable region

<400> SEQUENCE: 66

Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
            85                  90                  95

Lys Ile Arg Ser Thr Lys Leu Glu Asp Ser Ala Met Tyr Phe Cys Ala
            100                 105                 110

Ser Ser Ser Gly Leu Ala Gly Val Thr Gly Glu Leu Phe Phe Gly Glu
            115                 120                 125

Gly Ser Arg Leu Thr Val Leu Glu
    130                 135

<210> SEQ ID NO 67
<211> LENGTH: 397
<212> TYPE: DNA
<213> ORGANISM: Artificial Sequence
<220> FEATURE:
<223> OTHER INFORMATION: TCR3598 TCR beta chain specific for HLA-DR4
      epitope NY-ESO-1 116-135 , variable region

<400> SEQUENCE: 67
atggatactt ggctcgtgtg ctgggccatc ttcagcctgc tgaaggccgg actgaccgag      60
cccgaagtga cccagacacc tagccaccaa gtgacacaga tgggccagga agtgatcctg     120
cgctgcgtgc ccatcagcaa ccacctgtac ttctactggt acagacagat cctggggcag     180
aaagtggaat ttctggtgtc cttctacaac aacgagatca gcgagaagtc cgagatcttc     240
gacgaccagt tcagcgtgga acggcccgac ggcagcaact tcaccctgaa gatcagaagc     300
accaagctgg aagatagcgc catgtacttt tgcgccagca cggccagggg cgctggcacc     360
cagtattttg gccctggcac cagactgctg gtgctgg                              397

<210> SEQ ID NO 68
<211> LENGTH: 403
<212> TYPE: DNA

<213> ORGANISM: Artificial Sequence
<220> FEATURE:
<223> OTHER INFORMATION: TCR3598_2 TCR beta chain specific for HLA-DR4
      epitope NY-ESO-1 116-135 , variable region

<400> SEQUENCE: 68

```
atggatactt ggctcgtgtg ctgggccatc ttcagcctgc tgaaggccgg actgaccgag    60
cccgaagtga cccagacacc tagccaccaa gtgacacaga tgggccagga agtgatcctg   120
cgctgcgtgc ccatcagcaa ccacctgtac ttctactggt acagacagat cctggggcag   180
aaagtggaat ttctggtgtc cttctacaac aacgagatca gcgagaagtc cgagatcttc   240
gacgaccagt tcagcgtgga acggcccgac ggcagcaact tcaccctgaa gatcagaagc   300
accaagctgg aagatagcgc catgtacttt tgcgccagca gcgtgatgac cggcctgaac   360
accgaggcat ctttgggca gggcacccgg ctgaccgtgg tgg                      403
```

<210> SEQ ID NO 69
<211> LENGTH: 400
<212> TYPE: DNA
<213> ORGANISM: Artificial Sequence
<220> FEATURE:
<223> OTHER INFORMATION: TCR5412 TCR beta chain specific for HLA-DR4
      epitope NY-ESO-1 116-135 , variable region

<400> SEQUENCE: 69

```
atgggaacat ctctgctgtg ttggatggcc ctgtgcctgc tgggagccga tcatgccgat    60
acaggcgtgt cccaggaccc ccggcacaag attaccaagc ggggccagaa cgtgaccttc   120
agatgcgacc ccatcagcga gcacaaccgg ctgtactggt acagacagac cctgggccag   180
ggccccgagt tcctgaccta cttccagaac gaggcccagc tggaaaagag ccggctgctg   240
agcgacagat tcagcgccga aagacccaag ggcagcttca gcaccctgga aatccagcgg   300
accgagcagg gcgacagcgc catgtatctg tgtgccagca gcctggaccg gccctacaac   360
gagcagttct ttggcccagg cacccggctg accgtgctgg                         400
```

<210> SEQ ID NO 70
<211> LENGTH: 403
<212> TYPE: DNA
<213> ORGANISM: Artificial Sequence
<220> FEATURE:
<223> OTHER INFORMATION: TCR5412_2 TCR beta chain specific for HLA-DR4
      epitope NY-ESO-1 116-135 , variable region

<400> SEQUENCE: 70

```
atggatagct ggaccttttg ctgcgtgtcc ctgtgcatcc tggtggccaa gcacacagat    60
gccggcgtga tccagagccc cagacacgaa gtgaccgaga tgggccagga agtgaccctg   120
cgctgcaagc ctatcagcgg ccacaacagc ctgttctggt acagacagac catgatgcgg   180
ggcctggaac tgctgatcta cttcaacaac aacgtgccca tcgacgacag cggcatgccc   240
gaggatagat tcagcgccaa gatgcccaac gccagcttca gcaccctgaa gatccagccc   300
agcgagccca gagacagcgc cgtgtacttt tgcgccagca gctttctggc cagcgtgggc   360
tacgagcagt acttcggccc tggcaccaga ctgaccgtga ccg                     403
```

<210> SEQ ID NO 71
<211> LENGTH: 397
<212> TYPE: DNA
<213> ORGANISM: Artificial Sequence
<220> FEATURE:
<223> OTHER INFORMATION: TCR5412_3 TCR beta chain specific for HLA-DR4
      epitope NY-ESO-1 116-135 , variable region

<400> SEQUENCE: 71

```
atggatacca gagtgctgtg ctgcgccgtg atctgcctgc tgggagccgg actgtctaat    60
gccggcgtga tgcagaaccc cagacacctc gtgcggcgga gaggacagga agccagactg   120
cgctgcagcc ccatgaaggg ccacagccac gtgtactggt acagacagct gcccgaagag   180
ggcctgaagt tcatggtgta cctgcagaaa gagaacatca tcgacgagag cggcatgccc   240
aaagagcggt tcagcgccga gttccccaaa gagggcccca gcatcctgag aatccagcag   300
gtcgtgcggg gcgatagcgc cgcctacttt tgtgccagct ctccacctct gggcgagcag   360
tactttggcc ctggcaccag actgaccgtg accgagg                            397
```

<210> SEQ ID NO 72
<211> LENGTH: 391
<212> TYPE: DNA
<213> ORGANISM: Artificial Sequence
<220> FEATURE:
<223> OTHER INFORMATION: TCR3600 TCR beta chain specific for HLA-DR4
      epitope NY-ESO-1 116-135 , variable region

<400> SEQUENCE: 72

```
atggatactt ggctcgtgtg ctgggccatc ttcagcctgc tgaaggccgg actgaccgag    60
cccgaagtga cccagacacc tagccaccaa gtgacacaga tgggccagga agtgatcctg   120
cgctgcgtgc ccatcagcaa ccacctgtac ttctactggt acagacagat cctggggcag   180
aaagtggaat ttctggtgtc cttctacaac aacgagatca gcgagaagtc cgagatcttc   240
gacgaccagt tcagcgtgga acggcccgac ggcagcaact tcaccctgaa gatcagaagc   300
accaagctgg aagatagcgc catgtacttt tgcgccagca gcgtgatcta cgagcagtac   360
ttcggccctg gcacccggct gaccgtgacc g                                   391
```

<210> SEQ ID NO 73
<211> LENGTH: 391
<212> TYPE: DNA
<213> ORGANISM: Artificial Sequence
<220> FEATURE:
<223> OTHER INFORMATION: TCR5712 TCR beta chain specific for HLA-DR4
      epitope NY-ESO-1 116-135 , variable region

<400> SEQUENCE: 73

```
atggatactt ggctcgtgtg ctgggccatc ttcagcctgc tgaaggccgg actgaccgag    60
cccgaagtga cccagacacc tagccaccaa gtgacacaga tgggccagga agtgatcctg   120
cgctgcgtgc ccatcagcaa ccacctgtac ttctactggt acagacagat cctggggcag   180
aaagtggaat ttctggtgtc cttctacaac aacgagatca gcgagaagtc cgagatcttc   240
gacgaccagt tcagcgtgga acggcccgac ggcagcaact tcaccctgaa gatcagaagc   300
accaagctgg aagatagcgc catgtacttt tgcgccagca gcatcatcta cgagcagtac   360
ttcggccctg gcacccggct gaccgtgacc g                                   391
```

<210> SEQ ID NO 74
<211> LENGTH: 391
<212> TYPE: DNA
<213> ORGANISM: Artificial Sequence
<220> FEATURE:
<223> OTHER INFORMATION: TCR5415 TCR beta chain specific for HLA-DR4
      epitope NY-ESO-1 116-135 , variable region

<400> SEQUENCE: 74

```
atggatactt ggctcgtgtg ctgggccatc ttcagcctgc tgaaggccgg actgaccgag    60
```

```
cccgaagtga cccagacacc tagccaccaa gtgacacaga tgggccagga agtgatcctg    120
cgctgcgtgc ccatcagcaa ccacctgtac ttctactggt acagacagat cctggggcag    180
aaagtggaat ttctggtgtc cttctacaac aacgagatca gcgagaagtc cgagatcttc    240
gacgaccagt tcagcgtgga acggcccgac ggcagcaact tcaccctgaa gatcagaagc    300
accaagctgg aagatagcgc catgtacttt tgcgccagca gcgtgtacta cgagcagtac    360
ttcggccctg gcacccggct gaccgtgacc g                                   391
```

<210> SEQ ID NO 75
<211> LENGTH: 406
<212> TYPE: DNA
<213> ORGANISM: Artificial Sequence
<220> FEATURE:
<223> OTHER INFORMATION: TCR5713 TCR beta chain specific for HLA-DR4
      epitope NY-ESO-1 116-135, variable region

<400> SEQUENCE: 75

```
atggatactt ggctcgtgtg ctgggccatc ttcagcctgc tgaaggccgg actgaccgag     60
cccgaagtga cccagacacc tagccaccaa gtgacacaga tgggccagga agtgatcctg    120
cgctgcgtgc ccatcagcaa ccacctgtac ttctactggt acagacagat cctggggcag    180
aaagtggaat ttctggtgtc cttctacaac aacgagatca gcgagaagtc cgagatcttc    240
gacgaccagt tcagcgtgga acggcccgac ggcagcaact tcaccctgaa gatcagaagc    300
accaagctgg aagatagcgc catgtacttt tgcgccagca gctctggact ggccggcgtg    360
acaggcgagc tgttttttgg cgagggcagc agactgaccg tgctgg                   406
```

<210> SEQ ID NO 76
<211> LENGTH: 305
<212> TYPE: PRT
<213> ORGANISM: Artificial Sequence
<220> FEATURE:
<223> OTHER INFORMATION: TCR3598 TCR beta chain specific for HLA-DR4
      epitope NY-ESO-1 116-135

<400> SEQUENCE: 76

```
Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
            100                 105                 110

Ser Ser Gly Gln Gly Ala Gly Thr Gln Tyr Phe Gly Pro Gly Thr Arg
        115                 120                 125

Leu Leu Val Leu Glu Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160
```

```
Leu Val Cys Leu Ala Arg Gly Phe Phe Pro Asp His Val Glu Leu Ser
            165                 170                 175

Trp Trp Val Asn Gly Lys Glu Val His Ser Gly Val Ser Thr Asp Pro
        180                 185                 190

Gln Ala Tyr Lys Glu Ser Asn Tyr Ser Tyr Cys Leu Ser Ser Arg Leu
    195                 200                 205

Arg Val Ser Ala Thr Phe Trp His Asn Pro Arg Asn His Phe Arg Cys
210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
            245                 250                 255

Ala Asp Cys Gly Ile Thr Ser Ala Ser Tyr His Gln Gly Val Leu Ser
        260                 265                 270

Ala Thr Ile Leu Tyr Glu Ile Leu Leu Gly Lys Ala Thr Leu Tyr Ala
    275                 280                 285

Val Leu Val Ser Gly Leu Val Leu Met Ala Met Val Lys Lys Lys Asn
290                 295                 300

Ser
305

<210> SEQ ID NO 77
<211> LENGTH: 307
<212> TYPE: PRT
<213> ORGANISM: Artificial Sequence
<220> FEATURE:
<223> OTHER INFORMATION: TCR3598_2 TCR beta chain specific for HLA-DR4
      epitope NY-ESO-1 116-135

<400> SEQUENCE: 77

Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
            100                 105                 110

Ser Ser Val Met Thr Gly Leu Asn Thr Glu Ala Phe Phe Gly Gln Gly
        115                 120                 125

Thr Arg Leu Thr Val Val Glu Asp Leu Arg Asn Val Thr Pro Pro Lys
    130                 135                 140

Val Ser Leu Phe Glu Pro Ser Lys Ala Glu Ile Ala Asn Lys Gln Lys
145                 150                 155                 160

Ala Thr Leu Val Cys Leu Ala Arg Gly Phe Phe Pro Asp His Val Glu
                165                 170                 175

Leu Ser Trp Trp Val Asn Gly Lys Glu Val His Ser Gly Val Ser Thr
            180                 185                 190

Asp Pro Gln Ala Tyr Lys Glu Ser Asn Tyr Ser Tyr Cys Leu Ser Ser
        195                 200                 205
```

```
Arg Leu Arg Val Ser Ala Thr Phe Trp His Asn Pro Arg Asn His Phe
            210                 215                 220

Arg Cys Gln Val Gln Phe His Gly Leu Ser Glu Glu Asp Lys Trp Pro
225                 230                 235                 240

Glu Gly Ser Pro Lys Pro Val Thr Gln Asn Ile Ser Ala Glu Ala Trp
                245                 250                 255

Gly Arg Ala Asp Cys Gly Ile Thr Ser Ala Ser Tyr His Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Gly Leu Val Leu Met Ala Met Val Lys Lys
        290                 295                 300

Lys Asn Ser
305

<210> SEQ ID NO 78
<211> LENGTH: 306
<212> TYPE: PRT
<213> ORGANISM: Artificial Sequence
<220> FEATURE:
<223> OTHER INFORMATION: TCR5412 TCR beta chain specific for HLA-DR4
      epitope NY-ESO-1 116-135

<400> SEQUENCE: 78

Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Leu Asp Arg Pro Tyr Asn Glu Gln Phe Phe Gly Pro Gly Thr
        115                 120                 125

Arg Leu Thr Val Leu Glu Asp Leu Arg Asn Val Thr Pro Pro Lys Val
    130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Ala Tyr Lys Glu Ser Asn Tyr Ser Tyr Cys Leu Ser Ser Arg
        195                 200                 205

Leu Arg Val Ser Ala Thr Phe Trp His Asn Pro Arg Asn His Phe Arg
    210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
```

```
                    245                 250                 255

Arg Ala Asp Cys Gly Ile Thr Ser Ala Ser Tyr His Gln Gly Val Leu
            260                 265                 270

Ser Ala Thr Ile Leu Tyr Glu Ile Leu Leu Gly Lys Ala Thr Leu Tyr
            275                 280                 285

Ala Val Leu Val Ser Gly Leu Val Leu Met Ala Met Val Lys Lys Lys
290                 295                 300

Asn Ser
305

<210> SEQ ID NO 79
<211> LENGTH: 307
<212> TYPE: PRT
<213> ORGANISM: Artificial Sequence
<220> FEATURE:
<223> OTHER INFORMATION: TCR5412_2 TCR beta chain specific for HLA-DR4
      epitope NY-ESO-1 116-135

<400> SEQUENCE: 79

Met Asp Ser Trp Thr Phe Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asn Ser Leu Phe Trp Tyr Arg Gln Thr Met Met Arg Gly Leu Glu Leu
    50                  55                  60

Leu Ile Tyr Phe Asn Asn Val Pro Ile Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Ser Phe Leu Ala Ser Val Gly Tyr Glu Gln Tyr Phe Gly Pro Gly
        115                 120                 125

Thr Arg Leu Thr Val Thr Glu Asp Leu Arg Asn Val Thr Pro Pro Lys
    130                 135                 140

Val Ser Leu Phe Glu Pro Ser Lys Ala Glu Ile Ala Asn Lys Gln Lys
145                 150                 155                 160

Ala Thr Leu Val Cys Leu Ala Arg Gly Phe Phe Pro Asp His Val Glu
                165                 170                 175

Leu Ser Trp Trp Val Asn Gly Lys Glu Val His Ser Gly Val Ser Thr
            180                 185                 190

Asp Pro Gln Ala Tyr Lys Glu Ser Asn Tyr Ser Tyr Cys Leu Ser Ser
        195                 200                 205

Arg Leu Arg Val Ser Ala Thr Phe Trp His Asn Pro Arg Asn His Phe
    210                 215                 220

Arg Cys Gln Val Gln Phe His Gly Leu Ser Glu Asp Lys Trp Pro
225                 230                 235                 240

Glu Gly Ser Pro Lys Pro Val Thr Gln Asn Ile Ser Ala Glu Ala Trp
                245                 250                 255

Gly Arg Ala Asp Cys Gly Ile Thr Ser Ala Ser Tyr His Gln Gly Val
            260                 265                 270

Leu Ser Ala Thr Ile Leu Tyr Glu Ile Leu Leu Gly Lys Ala Thr Leu
        275                 280                 285
```

Tyr Ala Val Leu Val Ser Gly Leu Val Leu Met Ala Met Val Lys Lys
                290                 295                 300
Lys Asn Ser
305

<210> SEQ ID NO 80
<211> LENGTH: 304
<212> TYPE: PRT
<213> ORGANISM: Artificial Sequence
<220> FEATURE:
<223> OTHER INFORMATION: TCR5412_3 TCR beta chain specific for HLA-DR4
      epitope NY-ESO-1 116-135

<400> SEQUENCE: 80

Met Asp Thr Arg Val Leu Cys Cys Ala Val Ile Cys Leu Leu Gly Ala
1               5                   10                  15

Gly Leu Ser Asn Ala Gly Val Met Gln Asn Pro Arg His Leu Val Arg
                20                  25                  30

Arg Arg Gly Gln Glu Ala Arg Leu Arg Cys Ser Pro Met Lys Gly His
            35                  40                  45

Ser His Val Tyr Trp Tyr Arg Gln Leu Pro Glu Glu Gly Leu Lys Phe
        50                  55                  60

Met Val Tyr Leu Gln Lys Glu Asn Ile Ile Asp Glu Ser Gly Met Pro
65                  70                  75                  80

Lys Glu Arg Phe Ser Ala Glu Phe Pro Lys Glu Gly Pro Ser Ile Leu
                85                  90                  95

Arg Ile Gln Gln Val Val Arg Gly Asp Ser Ala Ala Tyr Phe Cys Ala
            100                 105                 110

Ser Ser Pro Pro Leu Gly Glu Gln Tyr Phe Gly Pro Gly Thr Arg Leu
        115                 120                 125

Thr Val Thr Glu Asp Leu Arg Asn Val Thr Pro Pro Lys Val Ser Leu
    130                 135                 140

Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
                165                 170                 175

Trp Val Asn Gly Lys Glu Val His Ser Gly Val Ser Thr Asp Pro Gln
            180                 185                 190

Ala Tyr Lys Glu Ser Asn Tyr Ser Tyr Cys Leu Ser Ser Arg Leu Arg
        195                 200                 205

Val Ser Ala Thr Phe Trp His Asn Pro Arg Asn His Phe Arg Cys Gln
    210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
                245                 250                 255

Asp Cys Gly Ile Thr Ser Ala Ser Tyr His Gln Gly Val Leu Ser Ala
            260                 265                 270

Thr Ile Leu Tyr Glu Ile Leu Leu Gly Lys Ala Thr Leu Tyr Ala Val
        275                 280                 285

Leu Val Ser Gly Leu Val Leu Met Ala Met Val Lys Lys Lys Asn Ser
    290                 295                 300

<210> SEQ ID NO 81
<211> LENGTH: 303
<212> TYPE: PRT
<213> ORGANISM: Artificial Sequence

```
<220> FEATURE:
<223> OTHER INFORMATION: TCR3600 TCR beta chain specific for HLA-DR4
      epitope NY-ESO-1 116-135

<400> SEQUENCE: 81

Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
            100                 105                 110

Ser Ser Val Ile Tyr Glu Gln Tyr Phe Gly Pro Gly Thr Arg Leu Thr
        115                 120                 125

Val Thr Glu Asp Leu Arg Asn Val Thr Pro Pro Lys Val Ser Leu Phe
    130                 135                 140

Glu Pro Ser Lys Ala Glu Ile Ala Asn Lys Gln Lys Ala Thr Leu Val
145                 150                 155                 160

Cys Leu Ala Arg Gly Phe Phe Pro Asp His Val Glu Leu Ser Trp Trp
                165                 170                 175

Val Asn Gly Lys Glu Val His Ser Gly Val Ser Thr Asp Pro Gln Ala
            180                 185                 190

Tyr Lys Glu Ser Asn Tyr Ser Tyr Cys Leu Ser Ser Arg Leu Arg Val
        195                 200                 205

Ser Ala Thr Phe Trp His Asn Pro Arg Asn His Phe Arg Cys Gln Val
    210                 215                 220

Gln Phe His Gly Leu Ser Glu Glu Asp Lys Trp Pro Glu Gly Ser Pro
225                 230                 235                 240

Lys Pro Val Thr Gln Asn Ile Ser Ala Glu Ala Trp Gly Arg Ala Asp
                245                 250                 255

Cys Gly Ile Thr Ser Ala Ser Tyr His Gln Gly Val Leu Ser Ala Thr
            260                 265                 270

Ile Leu Tyr Glu Ile Leu Leu Gly Lys Ala Thr Leu Tyr Ala Val Leu
        275                 280                 285

Val Ser Gly Leu Val Leu Met Ala Met Val Lys Lys Lys Asn Ser
    290                 295                 300

<210> SEQ ID NO 82
<211> LENGTH: 303
<212> TYPE: PRT
<213> ORGANISM: Artificial Sequence
<220> FEATURE:
<223> OTHER INFORMATION: TCR5712 TCR beta chain specific for HLA-DR4
      epitope NY-ESO-1 116-135

<400> SEQUENCE: 82

Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30
```

Gln Met Gly Gln Glu Val Ile Leu Arg Cys Val Pro Ile Ser Asn His
            35                  40                  45

Leu Tyr Phe Tyr Trp Tyr Arg Gln Ile Leu Gly Gln Lys Val Glu Phe
 50                  55                  60

Leu Val Ser Phe Tyr Asn Asn Glu Ile Ser Glu Lys Ser Glu Ile Phe
 65                  70                  75                  80

Asp Asp Gln Phe Ser Val Glu Arg Pro Asp Gly Ser Asn Phe Thr Leu
                 85                  90                  95

Lys Ile Arg Ser Thr Lys Leu Glu Asp Ser Ala Met Tyr Phe Cys Ala
            100                 105                 110

Ser Ser Ile Ile Tyr Glu Gln Tyr Phe Gly Pro Gly Thr Arg Leu Thr
        115                 120                 125

Val Thr Glu Asp Leu Arg Asn Val Thr Pro Pro Lys Val Ser Leu Phe
130                 135                 140

Glu Pro Ser Lys Ala Glu Ile Ala Asn Lys Gln Lys Ala Thr Leu Val
145                 150                 155                 160

Cys Leu Ala Arg Gly Phe Phe Pro Asp His Val Glu Leu Ser Trp Trp
                165                 170                 175

Val Asn Gly Lys Glu Val His Ser Gly Val Ser Thr Asp Pro Gln Ala
            180                 185                 190

Tyr Lys Glu Ser Asn Tyr Ser Tyr Cys Leu Ser Ser Arg Leu Arg Val
        195                 200                 205

Ser Ala Thr Phe Trp His Asn Pro Arg Asn His Phe Arg Cys Gln Val
210                 215                 220

Gln Phe His Gly Leu Ser Glu Glu Asp Lys Trp Pro Glu Gly Ser Pro
225                 230                 235                 240

Lys Pro Val Thr Gln Asn Ile Ser Ala Glu Ala Trp Gly Arg Ala Asp
                245                 250                 255

Cys Gly Ile Thr Ser Ala Ser Tyr His Gln Gly Val Leu Ser Ala Thr
            260                 265                 270

Ile Leu Tyr Glu Ile Leu Leu Gly Lys Ala Thr Leu Tyr Ala Val Leu
        275                 280                 285

Val Ser Gly Leu Val Leu Met Ala Met Val Lys Lys Lys Asn Ser
290                 295                 300

<210> SEQ ID NO 83
<211> LENGTH: 303
<212> TYPE: PRT
<213> ORGANISM: Artificial Sequence
<220> FEATURE:
<223> OTHER INFORMATION: TCR5415 TCR beta chain specific for HLA-DR4
      epitope NY-ESO-1 116-135

<400> SEQUENCE: 83

Met Asp Thr Trp Leu Val Cys Trp Ala Ile Phe Ser Leu Leu Lys Ala
 1               5                  10                  15

Gly Leu Thr Glu Pro Glu Val Gln Thr Pro Ser His Gln Val Thr
            20                  25                  30

Gln Met Gly Gln Glu Val Ile Leu Arg Cys Val Pro Ile Ser Asn His
            35                  40                  45

Leu Tyr Phe Tyr Trp Tyr Arg Gln Ile Leu Gly Gln Lys Val Glu Phe
 50                  55                  60

Leu Val Ser Phe Tyr Asn Asn Glu Ile Ser Glu Lys Ser Glu Ile Phe
 65                  70                  75                  80

Asp Asp Gln Phe Ser Val Glu Arg Pro Asp Gly Ser Asn Phe Thr Leu

```
                85                  90                  95
Lys Ile Arg Ser Thr Lys Leu Glu Asp Ser Ala Met Tyr Phe Cys Ala
                100                 105                 110

Ser Ser Val Tyr Tyr Glu Gln Tyr Phe Gly Pro Gly Thr Arg Leu Thr
            115                 120                 125

Val Thr Glu Asp Leu Arg Asn Val Thr Pro Pro Lys Val Ser Leu Phe
        130                 135                 140

Glu Pro Ser Lys Ala Glu Ile Ala Asn Lys Gln Lys Ala Thr Leu Val
145                 150                 155                 160

Cys Leu Ala Arg Gly Phe Phe Pro Asp His Val Glu Leu Ser Trp Trp
                165                 170                 175

Val Asn Gly Lys Glu Val His Ser Gly Val Ser Thr Asp Pro Gln Ala
                180                 185                 190

Tyr Lys Glu Ser Asn Tyr Ser Tyr Cys Leu Ser Ser Arg Leu Arg Val
                195                 200                 205

Ser Ala Thr Phe Trp His Asn Pro Arg Asn His Phe Arg Cys Gln Val
        210                 215                 220

Gln Phe His Gly Leu Ser Glu Glu Asp Lys Trp Pro Glu Gly Ser Pro
225                 230                 235                 240

Lys Pro Val Thr Gln Asn Ile Ser Ala Glu Ala Trp Gly Arg Ala Asp
                245                 250                 255

Cys Gly Ile Thr Ser Ala Ser Tyr His Gln Gly Val Leu Ser Ala Thr
                260                 265                 270

Ile Leu Tyr Glu Ile Leu Leu Gly Lys Ala Thr Leu Tyr Ala Val Leu
                275                 280                 285

Val Ser Gly Leu Val Leu Met Ala Met Val Lys Lys Asn Ser
                290                 295                 300

<210> SEQ ID NO 84
<211> LENGTH: 308
<212> TYPE: PRT
<213> ORGANISM: Artificial Sequence
<220> FEATURE:
<223> OTHER INFORMATION: TCR5713 TCR beta chain specific for HLA-DR4
      epitope NY-ESO-1 116-135

<400> SEQUENCE: 84

Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
                100                 105                 110

Ser Ser Ser Gly Leu Ala Gly Val Thr Gly Glu Leu Phe Phe Gly Glu
            115                 120                 125

Gly Ser Arg Leu Thr Val Leu Glu Asp Leu Arg Asn Val Thr Pro Pro
        130                 135                 140
```

Lys Val Ser Leu Phe Glu Pro Ser Lys Ala Glu Ile Ala Asn Lys Gln
145                 150                 155                 160

Lys Ala Thr Leu Val Cys Leu Ala Arg Gly Phe Phe Pro Asp His Val
            165                 170                 175

Glu Leu Ser Trp Trp Val Asn Gly Lys Glu Val His Ser Gly Val Ser
            180                 185                 190

Thr Asp Pro Gln Ala Tyr Lys Glu Ser Asn Tyr Ser Tyr Cys Leu Ser
            195                 200                 205

Ser Arg Leu Arg Val Ser Ala Thr Phe Trp His Asn Pro Arg Asn His
        210                 215                 220

Phe Arg Cys Gln Val Gln Phe His Gly Leu Ser Glu Glu Asp Lys Trp
225                 230                 235                 240

Pro Glu Gly Ser Pro Lys Pro Val Thr Gln Asn Ile Ser Ala Glu Ala
            245                 250                 255

Trp Gly Arg Ala Asp Cys Gly Ile Thr Ser Ala Ser Tyr His Gln Gly
            260                 265                 270

Val Leu Ser Ala Thr Ile Leu Tyr Glu Ile Leu Leu Gly Lys Ala Thr
            275                 280                 285

Leu Tyr Ala Val Leu Val Ser Gly Leu Val Leu Met Ala Met Val Lys
290                 295                 300

Lys Lys Asn Ser
305

<210> SEQ ID NO 85
<211> LENGTH: 918
<212> TYPE: DNA
<213> ORGANISM: Artificial Sequence
<220> FEATURE:
<223> OTHER INFORMATION: TCR3598 TCR beta chain specific for HLA-DR4
      epitope NY-ESO-1 116-135

<400> SEQUENCE: 85
atggatactt ggctcgtgtg ctgggccatc ttcagcctgc tgaaggccgg actgaccgag      60
cccgaagtga cccagacacc tagccaccaa gtgacacaga tgggccagga agtgatcctg     120
cgctgcgtgc ccatcagcaa ccacctgtac ttctactggt acagacagat cctggggcag     180
aaagtggaat ttctggtgtc cttctacaac aacgagatca gcgagaagtc cgagatcttc     240
gacgaccagt tcagcgtgga acggcccgac ggcagcaact tcaccctgaa gatcagaagc     300
accaagctgg aagatagcgc catgtacttt tgcgccagca gcggccaggg cgctggcacc     360
cagtattttg gccctggcac cagactgctg gtgctggaag atctgcggaa cgtgaccccc     420
cccaaggtgt ccctgttcga gcctagcaag gccgagatcg ccaacaagca gaaagccacc     480
ctcgtgtgcc tggccagagg cttcttcccc gaccacgtgg aactgtcttg gtgggtcaac     540
ggcaaagagg tgcacagcgg cgtgtccacc gatccccagg cctacaaaga gagcaactac     600
agctactgcc tgtccagcag actgcgggtg tccgccacct ctggcacaa cccccggaac     660 cacttcagat gccaggtgca gtttcacggc ctgagcgaag aggacaagtg gcctgagggc     720
agccccaagc ccgtgactca gaatatctct gccgaggcat ggggcagagc cgactgtggc     780
attaccagcg ccagctacca tcagggcgtg ctgagcgcca ccatcctgta cgagatcctg     840
ctgggcaagg ccaccctgta cgccgtgctg gtgtcaggcc tggtgctgat ggccatggtc     900
aagaagaaga acagctga                                                   918

<210> SEQ ID NO 86
<211> LENGTH: 924

```
<212> TYPE: DNA
<213> ORGANISM: Artificial Sequence
<220> FEATURE:
<223> OTHER INFORMATION: TCR3598_2 TCR beta chain specific for HLA-DR4
      epitope NY-ESO-1 116-135

<400> SEQUENCE: 86
atggatactt ggctcgtgtg ctgggccatc ttcagcctgc tgaaggccgg actgaccgag      60
cccgaagtga cccagacacc tagccaccaa gtgacacaga tgggccagga agtgatcctg     120
cgctgcgtgc ccatcagcaa ccacctgtac ttctactggt acagacagat cctggggcag     180
aaagtggaat tctggtgtc cttctacaac aacgagatca gcgagaagtc cgagatcttc      240
gacgaccagt tcagcgtgga acggcccgac ggcagcaact tcaccctgaa gatcagaagc     300
accaagctgg aagatagcgc catgtacttt gcgccagca gcgtgatgac cggcctgaac      360
accgaggcat tctttgggca gggcacccgg ctgaccgtgg tggaagatct gagaaacgtg     420
acccccccca aggtgtccct gttcgagcct agcaaggccg agatcgccaa caagcagaaa    480 gccacccctcg tgtgcctggc cagaggcttc ttccccgacc acgtgaact gtcttggtgg     540 gtcaacggca agaggtgca cagcggcgtg tccaccgatc ccaggccta caagagagc       600 aactacagct actgcctgtc cagcagactg cgggtgtccg ccaccttctg gcacaacccc     660
cggaaccact tcagatgcca ggtgcagttt cacggcctga gcaagagga caagtggcct    720 gagggcagcc ccaagcccgt gactcagaat atctctgccg aggcatgggg cagagccgac   780
tgtggcatta ccagcgccag ctaccatcag ggcgtgctga cgccaccat cctgtacgag     840 atcctgctgg gcaaggccac cctgtacgcc gtgctggtgt ctggcctggt gctgatggcc    900
atggtcaaga agaagaacag ctga                                          924

<210> SEQ ID NO 87
<211> LENGTH: 921
<212> TYPE: DNA
<213> ORGANISM: Artificial Sequence
<220> FEATURE:
<223> OTHER INFORMATION: TCR5412 TCR beta chain specific for HLA-DR4
      epitope NY-ESO-1 116-135

<400> SEQUENCE: 87
atgggaacat ctctgctgtg ttggatggcc ctgtgcctgc tgggagccga tcatgccgat     60
acaggcgtgt cccaggaccc ccggcacaag attaccaagc ggggccagaa cgtgaccttc    120
agatgcgacc ccatcagcga gcacaaccgg ctgtactggt acagacagac cctgggccag   180
ggccccgagt cctgacccta cttccagaac gaggcccagc tggaaaagag ccggctgctg    240
agcgacagat tcagcgccga aagacccaag ggcagcttca gcaccctgga aatccagcgg    300
accgagcagg gcgacagcgc catgtatctg tgtgccagca gcctggaccg gccctacaac    360
gagcagttct ttggcccagg cacccggctg accgtgctgg aagatctgag aaacgtgacc    420
ccccccaagg tgtccctgtt cgagcctagc aaggccgaga tcgccaacaa gcagaaagcc    480
accctcgtgt gcctggccag aggcttcttc cccgaccacg tggaactgtc ttggtgggtc    540
aacggcaaag aggtgcacag cggcgtgtcc accgatcccc aggcctacaa agagagcaac    600
tacagctact gcctgagcag cagactgcgg gtgtccgcca ccttctggca accccccgg    660 aaccacttca ggtgccaggt gcagtttcac ggcctgagcg aagaggacaa gtggcccgag   720
ggcagcccta gcccgtgac ccagaatatc tctgccgaag cctggggcag agccgactgt    780
ggcattacca gcgccagcta ccatcagggc gtgctgagcg ccaccatcct gtacgagatc    840
```

```
ctgctgggca aggccaccct gtacgccgtg ctggtgtctg gcctggtgct gatggccatg    900
gtcaagaaga agaacagctg a                                              921
```

<210> SEQ ID NO 88
<211> LENGTH: 924
<212> TYPE: DNA
<213> ORGANISM: Artificial Sequence
<220> FEATURE:
<223> OTHER INFORMATION: TCR5412_2 TCR beta chain specific for HLA-DR4
      epitope NY-ESO-1 116-135

<400> SEQUENCE: 88

```
atggatagct ggacctttg ctgcgtgtcc ctgtgcatcc tggtggccaa gcacacagat     60
gccggcgtga tccagagccc cagacacgaa gtgaccgaga tgggccagga agtgaccctg   120
cgctgcaagc ctatcagcgg ccacaacagc ctgttctggt acagacagac catgatgcgg   180
ggcctggaac tgctgatcta cttcaacaac aacgtgccca tcgacgacag cggcatgccc   240
gaggatagat tcagcgccaa gatgcccaac gccagcttca gcaccctgaa gatccagccc   300
agcgagccca gagacagcgc cgtgtacttt tgcgccagca gctttctggc cagcgtgggc   360
tacgagcagt acttcggccc tggcaccaga ctgaccgtga ccgaggacct gagaaacgtg   420 accccccca agtgtctct gttcgagccc agcaaggccg agatcgccaa caagcagaaa    480
gccaccctcg tgtgcctggc cagaggcttc ttccccgacc acgtgaact gtcttggtgg   540 gtcaacggca agaggtgca cagcggcgtg tccaccgatc cccaggccta caaagagagc   600
aactacagct actgcctgag cagcagactg cgggtgtccg ccaccttctg gcacaacccc   660
cggaaccact tcagatgcca ggtgcagttt cacggcctga gcgaagagga caagtggccc   720
gagggcagcc ctaagcccgt gacccagaat atctctgccg aagcctgggg cagagccgac   780
tgtggcatta ccagcgccag ctaccatcag ggcgtgctga gcgccaccat cctgtacgag   840
atcctgctgg gcaaggccac cctgtacgcc gtgctggtgt ctggcctggt gctgatggcc   900
atggtcaaga agaagaacag ctga                                         924
```

<210> SEQ ID NO 89
<211> LENGTH: 915
<212> TYPE: DNA
<213> ORGANISM: Artificial Sequence
<220> FEATURE:
<223> OTHER INFORMATION: TCR5412_3 TCR beta chain specific for HLA-DR4
      epitope NY-ESO-1 116-135

<400> SEQUENCE: 89

```
atggatacca gagtgctgtg ctgcgccgtg atctgcctgc tgggagccgg actgtctaat    60
gccggcgtga tgcagaaccc cagacaccc gtgcggcgga ggacacagga agccagactg   120
cgctgcagcc ccatgaaggg ccacagccac gtgtactggt acagacagct gcccgaagag   180
ggcctgaagt tcatggtgta cctgcagaaa gagaacatca tcgacgagag cggcatgccc   240
aaagagcggt tcagcgccga gttccccaaa gagggcccca gcatcctgag aatccagcag   300
gtcgtgcggg gcgatagcgc cgcctacttt tgtgccagct ctccacctct gggcgagcag   360
tactttggcc ctggcaccag actgaccgtg accgaggacc tgagaaacgt gacccccccc   420
aaggtgtccc tgttcgagcc tagcaaggcc gagatcgcca acaagcagaa agccaccctc   480
gtgtgcctgg ccagaggctt cttccccgac acgtggaac tgtcttggtg gtcaacggc    540 aaagaggtgc acagcggcgt gtccaccgat cccaggcct acaaagagag caactacagc   600
tactgcctga gcagcagact gcgggtgtcc gccaccttct ggcacaaccc ccggaaccac   660
```

```
ttcagatgcc aggtgcagtt tcacggcctg agcgaagagg acaagtggcc cgagggcagc    720
cctaagcccg tgacccagaa tatctctgcc gaagcctggg gcagagccga ctgtggcatt    780
accagcgcca gctaccatca gggcgtgctg agcgccacca tcctgtacga gatcctgctg    840
ggcaaggcca ccctgtacgc cgtgctggtg tctggcctgg tgctgatggc catggtcaag    900
aagaagaaca gctga                                                     915

<210> SEQ ID NO 90
<211> LENGTH: 912
<212> TYPE: DNA
<213> ORGANISM: Artificial Sequence
<220> FEATURE:
<223> OTHER INFORMATION: TCR3600 TCR beta chain specific for HLA-DR4
      epitope NY-ESO-1 116-135

<400> SEQUENCE: 90
atggatactt ggctcgtgtg ctgggccatc ttcagcctgc tgaaggccgg actgaccgag     60
cccgaagtga cccagacacc tagccaccaa gtgacacaga tgggccagga agtgatcctg    120
cgctgcgtgc ccatcagcaa ccacctgtac ttctactggt acagacagat cctggggcag    180
aaagtggaat tctggtgtc cttctacaac aacgagatca gcgagaagtc cgagatcttc    240
gacgaccagt tcagcgtgga acggcccgac ggcagcaact tcaccctgaa gatcagaagc    300
accaagctgg aagatagcgc catgtacttt tgcgccagca gcgtgatcta cgagcagtac    360
ttcggccctg gcacccggct gaccgtgacc gaggatctga aaacgtgac cccccccaag    420 gtgtccctgt tcgagcctag caaggccgag atcgccaaca gcagaaagc caccctcgtg    480 tgcctggcca gaggcttctt ccccgaccac gtggaactgt cttggtgggt caacggcaaa    540
gaggtgcaca cgcgcgtgtc caccgatccc caggcctaca agagagcaa ctacagctac    600 tgcctgtcca gcagactgcg ggtgtccgcc accttctggc acaacccccg gaaccacttc    660
agatgccagg tgcagtttca cggcctgagc gaagaggaca gtggcctga ggcagcccc    720 aagcccgtga ctcagaatat ctctgccgag gcatggggca gagccgactg tggcattacc    780
agcgccagct accatcaggg cgtgctgagc gccaccatcc tgtacgagat cctgctgggc    840
aaggccaccc tgtacgccgt gctggtgtct ggcctggtgc tgatggccat ggtcaagaag    900
aagaacagct ga                                                        912

<210> SEQ ID NO 91
<211> LENGTH: 912
<212> TYPE: DNA
<213> ORGANISM: Artificial Sequence
<220> FEATURE:
<223> OTHER INFORMATION: TCR5712 TCR beta chain specific for HLA-DR4
      epitope NY-ESO-1 116-135

<400> SEQUENCE: 91
atggatactt ggctcgtgtg ctgggccatc ttcagcctgc tgaaggccgg actgaccgag     60
cccgaagtga cccagacacc tagccaccaa gtgacacaga tgggccagga agtgatcctg    120
cgctgcgtgc ccatcagcaa ccacctgtac ttctactggt acagacagat cctggggcag    180
aaagtggaat tctggtgtc cttctacaac aacgagatca gcgagaagtc cgagatcttc    240
gacgaccagt tcagcgtgga acggcccgac ggcagcaact tcaccctgaa gatcagaagc    300
accaagctgg aagatagcgc catgtacttt tgcgccagca gcatcatcta cgagcagtac    360
ttcggccctg gcacccggct gaccgtgacc gaggatctga aaacgtgac cccccccaag    420
```

```
gtgtccctgt tcgagcctag caaggccgag atcgccaaca agcagaaagc caccctcgtg      480
tgcctggcca gaggcttctt ccccgaccac gtggaactgt cttggtgggt caacggcaaa      540
gaggtgcaca gcggcgtgtc caccgatccc caggcctaca agagagcaa ctacagctac       600 tgcctgtcca gcagactgcg ggtgtccgcc accttctggc acaaccccg gaaccacttc       660 agatgccagg tgcagtttca cggcctgagc gaagaggaca gtggcctga gggcagcccc       720 aagcccgtga ctcagaatat ctctgccgag gcatggggca gagccgactg tggcattacc      780
agcgccagct accatcaggg cgtgctgagc gccaccatcc tgtacgagat cctgctgggc      840
aaggccaccc tgtacgccgt gctggtgtct ggcctggtgc tgatggccat ggtcaagaag      900
aagaacagct ga                                                          912

<210> SEQ ID NO 92
<211> LENGTH: 912
<212> TYPE: DNA
<213> ORGANISM: Artificial Sequence
<220> FEATURE:
<223> OTHER INFORMATION: TCR5415 TCR beta chain specific for HLA-DR4
      epitope NY-ESO-1 116-135

<400> SEQUENCE: 92
atggatactt ggctcgtgtg ctgggccatc ttcagcctgc tgaaggccgg actgaccgag       60
cccgaagtga cccagacacc tagccaccaa gtgacacaga tgggccagga agtgatcctg      120
cgctgcgtgc ccatcagcaa ccacctgtac ttctactggt acagacagat cctggggcag      180
aaagtggaat ttctggtgtc cttctacaac aacgagatca gcgagaagtc cgagatcttc      240
gacgaccagt tcagcgtgga acggcccgac ggcagcaact tcaccctgaa gatcagaagc      300
accaagctgg aagatagcgc catgtacttt tgcgccagca cgtgtacta cgagcagtac      360 ttcggccctg gcacccggct gaccgtgacc gaggatctga aaacgtgac cccccccaag       420 gtgtccctgt tcgagcctag caaggccgag atcgccaaca agcagaaagc caccctcgtg      480
tgcctggcca gaggcttctt ccccgaccac gtggaactgt cttggtgggt caacggcaaa      540
gaggtgcaca gcggcgtgtc caccgatccc caggcctaca agagagcaa ctacagctac       600 tgcctgtcca gcagactgcg ggtgtccgcc accttctggc acaaccccg gaaccacttc       660 agatgccagg tgcagtttca cggcctgagc gaagaggaca gtggcctga gggcagcccc       720 aagcccgtga ctcagaatat ctctgccgag gcatggggca gagccgactg tggcattacc      780
agcgccagct accatcaggg cgtgctgagc gccaccatcc tgtacgagat cctgctgggc      840
aaggccaccc tgtacgccgt gctggtgtct ggcctggtgc tgatggccat ggtcaagaag      900
aagaacagct ga                                                          912

<210> SEQ ID NO 93
<211> LENGTH: 927
<212> TYPE: DNA
<213> ORGANISM: Artificial Sequence
<220> FEATURE:
<223> OTHER INFORMATION: TCR5713 TCR beta chain specific for HLA-DR4
      epitope NY-ESO-1 116-135

<400> SEQUENCE: 93
atggatactt ggctcgtgtg ctgggccatc ttcagcctgc tgaaggccgg actgaccgag       60
cccgaagtga cccagacacc tagccaccaa gtgacacaga tgggccagga agtgatcctg      120
cgctgcgtgc ccatcagcaa ccacctgtac ttctactggt acagacagat cctggggcag      180
aaagtggaat ttctggtgtc cttctacaac aacgagatca gcgagaagtc cgagatcttc      240
```

```
gacgaccagt tcagcgtgga acggcccgac ggcagcaact tcaccctgaa gatcagaagc    300
accaagctgg aagatagcgc catgtacttt tgcgccagca gctctggact ggccggcgtg    360
acaggcgagc tgttttttgg cgagggcagc agactgaccg tgctggaaga tctgcggaac    420
gtgacccccc ccaaggtgtc cctgttcgag cctagcaagg ccgagatcgc caacaagcag    480
aaagccaccc tcgtgtgcct ggccagaggc ttcttccccg accacgtgga actgtcttgg    540
tgggtcaacg gcaaagaggt gcacagcggc gtgtccaccg atcccaggc ctacaaagag    600 agcaactaca gctactgcct gtcctcccgg ctgagagtgt ccgccacctt ctggcacaac    660 cccccggaacc acttcagatg ccaggtgcag tttcacggcc tgagcgaaga ggacaagtgg    720
cctgagggca gccccaagcc cgtgactcag aatatctctg ccgaggcatg gggcagagcc    780
gactgtggca ttaccagcgc cagctaccat cagggcgtgc tgagcgccac catcctgtac    840
gagatcctgc tgggcaaggc cacccttgtac gccgtgctgg tgtcaggcct ggtgctgatg    900
gccatggtca agaagaagaa cagctga    927

<210> SEQ ID NO 94
<211> LENGTH: 1794
<212> TYPE: DNA
<213> ORGANISM: Artificial Sequence
<220> FEATURE:
<223> OTHER INFORMATION: TCR3598 single chain nucleic acid TCR construct
      specific for HLA-DR4 epitope NY-ESO-1 116-135

<400> SEQUENCE: 94
atggatactt ggctcgtgtg ctgggccatc ttcagcctgc tgaaggccgg actgaccgag     60
cccgaagtga cccagacacc tagccaccaa gtgacacaga tgggccagga agtgatcctg    120
cgctgcgtgc ccatcagcaa ccacctgtac ttctactggt acagacagat cctggggcag    180
aaagtggaat ttctggtgtc cttctacaac aacgagatca gcgagaagtc cgagatcttc    240
gacgaccagt tcagcgtgga acggcccgac ggcagcaact tcaccctgaa gatcagaagc    300
accaagctgg aagatagcgc catgtacttt tgcgccagca gcggccaggg cgctggcacc    360
cagtattttg gccctggcac cagactgctg gtgctggaag atctgcggaa cgtgaccccc    420
cccaaggtgt ccctgttcga gcctagcaag gccgagatcg ccaacaagca gaaagccacc    480
ctcgtgtgcc tggccagagg cttcttcccc gaccacgtgg aactgtcttg gtgggtcaac    540
ggcaaagagg tgcacagcgg cgtgtccacc gatccccagg cctacaaaga gagcaactac    600
agctactgcc tgtccagcag actgcgggtg tccgccacct tctggcacaa ccccccggaac    660 cacttcagat gccaggtgca gtttcacggc ctgagcgaag aggacaagtg gcctgagggc    720
agccccaagc ccgtgactca gaatatctct gccgaggcat ggggcagagc cgactgtggc    780
attaccagcg ccagctacca tcagggcgtg ctgagcgcca ccatcctgta cgagatcctg    840
ctgggcaagg ccacccttgta cgccgtgctg gtgtcaggcc tggtgctgat ggccatggtc    900
aagaagaaga acagcggcag cggcgccacc aactttagtc tgctgaaaca ggccggcgac    960
gtggaagaga accctggccc catgatgaag tccctgcggg tgctgctcgt gatcctgtgg   1020
ctgcagctga gctgggtgtg gtcccagcag aaagaggtgg aacaggaccc aggccctctg   1080
agcgtgccag agggcgctat cgtgtccctg aattgcacct acagcaacag cgccttccag   1140
tacttcatgt ggtatcggca gtacagccgg aagggccccg agctgctgat gtacaccta   1200 tccagcggca caaagagga cggccggttc acagcccagg tggacaagag cagcaagtac   1260
atctccctgt catccggga cagccagccc agcgacagcg ccacatatct gtgcgccatg   1320
```

| | |
|---|---|
| agacagggcg gctccgagaa gctggtgttc ggcaagggca caaagctgac cgtgaacccc | 1380 |
| tacatccaga accccgagcc cgccgtgtac cagctgaagg accctagaag ccaggacagc | 1440 |
| accctgtgcc tgttcaccga cttcgacagc cagatcaacg tgcccaagac catggaaagc | 1500 |
| ggcaccttca tcaccgacaa gaccgtgctg gacatgaagg ccatggacag caagagcaac | 1560 |
| ggcgccattg cctggtccaa ccagaccagc ttcacatgcc aggacatctt caaagagaca | 1620 |
| aacgccacct accccagcag cgacgtgccc tgtgatgcca ccctgaccga gaagtctttc | 1680 |
| gagacagaca tgaacctgaa cttccagaac ctgagcgtga tgggcctgag aatcctgctg | 1740 |
| ctgaaagtgg ccggattcaa cctgctgatg accctgcggc tgtggtccag ctga | 1794 |

<210> SEQ ID NO 95
<211> LENGTH: 1800
<212> TYPE: DNA
<213> ORGANISM: Artificial Sequence
<220> FEATURE:
<223> OTHER INFORMATION: TCR3598_2 single chain nucleic acid TCR
      construct specific for HLA-DR4 epitope NY-ESO-1 116-135

<400> SEQUENCE: 95

| | |
|---|---|
| atggatactt ggctcgtgtg ctgggccatc ttcagcctgc tgaaggccgg actgaccgag | 60 |
| cccgaagtga cccagacacc tagccaccaa gtgacacaga tgggccagga agtgatcctg | 120 |
| cgctgcgtgc ccatcagcaa ccacctgtac ttctactggt acagacagat cctggggcag | 180 |
| aaagtggaat ttctggtgtc cttctacaac aacgagatca gcgagaagtc cgagatcttc | 240 |
| gacgaccagt tcagcgtgga acggcccgac ggcagcaact tcaccctgaa gatcagaagc | 300 |
| accaagctgg aagatagcgc catgtacttt tgcgccagca gcgtgatgac cggcctgaac | 360 |
| accgaggcat tctttgggca gggcaccccg ctgaccgtgg tggaagatct gagaaacgtg | 420 |
| acccccccca aggtgtccct gttcgagcct agcaaggccg agatcgccaa caagcagaaa | 480 |
| gccaccctcg tgtgcctggc cagaggcttc ttccccgacc acgtggaact gtcttggtgg | 540 |
| gtcaacggca agagggtgca cagcggcgtg tccaccgatc ccaggccta caaagagagc | 600 |
| aactacagct actgcctgtc cagcagactg cgggtgtccg ccaccttctg gcacaacccc | 660 |
| cggaaccact tcagatgcca ggtgcagttt cacggcctga gcgaagagga caagtggcct | 720 |
| gagggcagcc ccaagcccgt gactcagaat atctctgccg aggcatgggg cagagccgac | 780 |
| tgtggcatta ccagcgccag ctaccatcag ggcgtgctga gcgccaccat cctgtacgag | 840 |
| atcctgctgg gcaaggccac cctgtacgcc gtgctggtgt ctggcctggt gctgatggcc | 900 |
| atggtcaaga agaagaacag cggcagcggc gccaccaact ttagtctgct gaaacaggcc | 960 |
| ggcgacgtgg aagagaaccc tggccccatg aactactctc ccggcctggt gtctctgatt | 1020 |
| ctgctgctgc tgggccggac cagaggcgat tctgtgaccc agatggaagg ccccgtgacc | 1080 |
| ctgagcgagg aagccttcct gaccatcaat tgcacctaca ccgccaccgg ctaccccagc | 1140 |
| ctgttttggt acgtgcagta ccccggcgag ggcctgcagc tgctgctgaa agccaccaag | 1200 |
| gccgacgaca agggcagcaa caagggcttc gaggccacct accggaaaga caaccagtc | 1260 |
| ttccacctgg aaaagggcag cgtgcaggtg tccgactccg ccgtgtattt ctgcgccctg | 1320 |
| agagattctg gcggcggagc cgatggcctg acctttggca agggcacaca cctgatcatc | 1380 |
| cagccctaca tccagaaccc cgagcctgcc gtgtaccagc tgaaggaccc tagaagccag | 1440 |
| gacagcaccc tgtgcctgtt caccgacttc gacagccaga tcaacgtgcc caagaccatg | 1500 |
| gaaagcggca ccttcatcac cgacaagacc gtgctggaca tgaaggccat ggacagcaag | 1560 |

-continued

| | |
|---|---|
| agcaacggcg ccattgcctg gtccaaccag accagcttca catgccagga catcttcaaa | 1620 |
| gagactaacg ccacataccc cagcagcgac gtgccctgtg atgccaccct gaccgagaag | 1680 |
| tctttcgaga cagacatgaa cctgaacttc cagaacctga gcgtgatggg cctgagaatc | 1740 |
| ctgctgctga aggtggccgg cttcaacctg ctgatgaccc tgagactgtg gtccagctga | 1800 |

<210> SEQ ID NO 96
<211> LENGTH: 1794
<212> TYPE: DNA
<213> ORGANISM: Artificial Sequence
<220> FEATURE:
<223> OTHER INFORMATION: TCR5412 single chain nucleic acid TCR construct specific for HLA-DR4 epitope NY-ESO-1 116-135

<400> SEQUENCE: 96

| | |
|---|---|
| atgggaacat ctctgctgtg ttggatggcc ctgtgcctgc tgggagccga tcatgccgat | 60 |
| acaggcgtgt cccaggaccc ccggcacaag attaccaagc ggggccagaa cgtgaccttc | 120 |
| agatgcgacc ccatcagcga gcacaacggg ctgtactggt acagacagac cctgggccag | 180 |
| ggccccgagt tcctgaccta cttccagaac gaggcccagc tggaaaagag ccggctgctg | 240 |
| agcgacagat tcagcgccga aagacccaag ggcagcttca gcaccctgga aatccagcgg | 300 |
| accgagcagg gcgacagcgc catgtatctg tgtgccagca gcctggaccg gccctacaac | 360 |
| gagcagttct ttgcccaggg cacccggctg accgtgctgg aagatctgag aaacgtgacc | 420 |
| ccccccaagg tgtccctgtt cgagcctagc aaggccgaga tcgccaacaa gcagaaagcc | 480 |
| accctcgtgt gcctggccag aggcttcttc cccgaccacg tggaactgtc ttggtgggtc | 540 |
| aacggcaaag aggtgcacag cggcgtgtcc accgatcccc aggcctacaa agagagcaac | 600 |
| tacagctact gcctgagcag cagactgcgg gtgtccgcca ccttctggca acccccccgg | 660 |
| aaccacttca ggtgccaggt gcagtttcac ggcctgagcg aagaggacaa gtggcccgag | 720 |
| ggcagcccta gcccgtgac ccagaatatc tctgccgaag cctggggcag agccgactgt | 780 |
| ggcattacca gcgccagcta ccatcagggc gtgctgagcg ccaccatcct gtacgagatc | 840 |
| ctgctgggca aggccaccct gtacgccgtg ctggtgtctg gcctggtgct gatggccatg | 900 |
| gtcaagaaga agaacagcgg cagcggcgcc accaacttca gcctgctgaa acaggccggc | 960 |
| gacgtggaag agaaccctgg ccctatgctc ctgctgctgg tgcctgcctt ccaagtgatc | 1020 |
| ttcaccctgg gcggcaccag agcccagagc gtgacacagc tggatagcca ggtgcccgtg | 1080 |
| ttcgaagagg cccctgtgga actgcggtgc aactactcca gcagcgtgtc cgtgtacctg | 1140 |
| ttttggtacg tgcagtaccc caaccagggc ctgcagctgc tgctgaagta cctgagcggc | 1200 |
| tccacccctg gtggaatccat caacggcttc gaggccgagt tcaacaagag ccagaccagc | 1260 |
| ttccacctga gaaagcccag cgtgcacatc agcgataccg ccgagtactt ctgcgccgtg | 1320 |
| accctgaacc gggacgacaa gatcatcttc ggcaagggca ccagactgca catcctgccc | 1380 |
| aacatccaga accccgagcc cgccgtgtac cagctgaagg accctagaag ccaggatagc | 1440 |
| accctgtgtc tgttcaccga cttcgacagc cagatcaacg tgcccaagac catggaaagc | 1500 |
| ggcaccttca tcaccgacaa gacagtgctg gacatgaagg ccatggacag caagagcaac | 1560 |
| ggcgccattg cctggtccaa ccagacaagc ttcacatgcc aggacatctt caagagaca | 1620 |
| aacgccacct accccagctc cgacgtgccc tgtgatgcca ccctgaccga gaagtccttc | 1680 |
| gagacagaca tgaacctgaa tttccagaac ctgagcgtga tgggcctgcg gatcctgctg | 1740 |
| ctgaaagtgg ccggcttcaa cctgctgatg accctgagac tgtggtccag ctga | 1794 |

<210> SEQ ID NO 97
<211> LENGTH: 1800
<212> TYPE: DNA
<213> ORGANISM: Artificial Sequence
<220> FEATURE:
<223> OTHER INFORMATION: TCR5412_2 single chain nucleic acid TCR
      construct specific for HLA-DR4 epitope NY-ESO-1 116-135

<400> SEQUENCE: 97

```
atggatagct ggacctttg ctgcgtgtcc ctgtgcatcc tggtggccaa gcacacagat      60
gccggcgtga tccagagccc cagacacgaa gtgaccgaga tgggccagga agtgaccctg     120
cgctgcaagc ctatcagcgg ccacaacagc ctgttctggt acagacagac catgatgcgg    180
ggcctggaac tgctgatcta cttcaacaac aacgtgccca tcgacgacag cggcatgccc    240
gaggatagat tcagcgccaa gatgcccaac gccagcttca gcccctgaa gatccagccc    300
agcgagccca gagacagcgc cgtgtacttt tgcgccagca gctttctggc agcgtgggc    360
tacgagcagt acttcggccc tggcaccaga ctgaccgtga ccgaggacct gagaaacgtg    420
acccccccca agtgtctctt gttcgagccc agcaaggccg agatcgccaa caagcagaaa    480
gccaccctcg tgtgcctggc cagaggcttc ttccccgacc acgtggaact gtcttggtgg    540
gtcaacggca agaggtgcag cagcggcgtg tccaccgatc cccaggccta caaagagagc    600
aactacagct actgcctgag cagcagactg cgggtgtccg ccaccttctg gcacaacccc    660
cggaaccact tcagatgcca ggtgcagttt cacggcctga gcgaagagga caagtggccc    720
gagggcagcc ctaagcccgt gacccagaat atctctgccg aagcctgggg cagagccgac    780
tgtggcatta ccagcgccag ctaccatcag ggcgtgctga gcgccaccat cctgtacgag    840
atcctgctgg gcaaggccac cctgtacgcc gtgctggtgt ctggcctggt gctgatggcc    900
atggtcaaga agaagaacag cggcagcggc gccaccaact tcagcctgct gaaacaggcc    960
ggcgacgtgg aagagaaccc tggccctatg ctcctgctgc tggtgcctgc cttccaagtg   1020
atcttcaccc tgggcggcac cagggcccag tctgtgacac agctggatag ccaggtgccc   1080
gtgttcgaag aggcccctgt ggaactgcgg tgcaactact ccagcagcgt gtccgtgtac   1140
ctgttttggt acgtgcagta ccccaaccag ggcctgcagc tgctgctgaa gtacctgagc   1200
ggctccaccc tggtggaatc catcaacggc ttcgaggccg agttcaacaa gagccagacc   1260
agcttccatc tgcggaagcc cagcgtgcac atcagcgata ccgccgagta cttctgtgcc   1320
gtgacccgga actccggcaa cacccctctg gtgtttggca agggcacacg gctgagcgtg   1380
atcgccaata tccagaaccc cgagcctgcc gtgtaccagc tgaaggaccc cagaagccag   1440
gatagcaccc tgtgcctgtt caccgacttc gacagccaga tcaatgtgcc caagaccatg   1500
gaaagcggca ccttcatcac cgacaagacc gtgctggaca tgaaggccat ggacagcaag   1560
agcaacggcg ccattgcctg gtccaaccag acaagcttca catgccagga catcttcaaa   1620
gagacaaacg ccacctaccc cagctccgac gtgccctgtg atgccaccct gaccgagaag   1680
tccttcgaga cagacatgaa cctgaacttc cagaacctgt ccgtgatggg cctgcggatc   1740
ctgctgctga aagtggccgg cttcaacctg ctgatgaccc tgagactgtg gtccagctga   1800
```

<210> SEQ ID NO 98
<211> LENGTH: 1788
<212> TYPE: DNA
<213> ORGANISM: Artificial Sequence
<220> FEATURE:
<223> OTHER INFORMATION: TCR5412_3 single chain nucleic acid TCR construct specific for HLA-DR4 epitope NY-ESO-1 116-135

<400> SEQUENCE: 98

| | | | | | |
|---|---|---|---|---|---|
| atggatacca | gagtgctgtg | ctgcgccgtg | atctgcctgc | tgggagccgg | actgtctaat | 60 |
| gccggcgtga | tgcagaaccc | cagacacctc | gtgcggcgga | gaggacagga | agccagactg | 120 |
| cgctgcagcc | ccatgaaggg | ccacagccac | gtgtactggt | acagacagct | gcccgaagag | 180 |
| ggcctgaagt | tcatggtgta | cctgcagaaa | gagaacatca | tcgacgagag | cggcatgccc | 240 |
| aaagagcggt | tcagcgccga | gttccccaaa | gagggcccca | gcatcctgag | aatccagcag | 300 |
| gtcgtgcggg | gcgatagcgc | cgcctacttt | tgtgccagct | ctccacctct | gggcgagcag | 360 |
| tactttggcc | ctggcaccag | actgaccgtg | accgaggacc | tgagaaacgt | gaccccccc | 420 |
| aaggtgtccc | tgttcgagcc | tagcaaggcc | gagatcgcca | acaagcagaa | agccacctc | 480 |
| gtgtgcctgg | ccagaggctt | cttccccgac | cacgtggaac | tgtcttggtg | ggtcaacggc | 540 |
| aaagaggtgc | acagcggcgt | gtccaccgat | ccccaggcct | acaaagagag | caactacagc | 600 |
| tactgcctga | gcagcagact | gcgggtgtcc | gccaccttct | ggcacaaccc | ccggaaccac | 660 |
| ttcagatgcc | aggtgcagtt | tcacggcctg | agcgaagagg | acaagtggcc | cgagggcagc | 720 |
| cctaagcccg | tgacccagaa | tatctctgcc | gaagcctggg | gcagagccga | ctgtggcatt | 780 |
| accagcgcca | gctaccatca | gggcgtgctg | agcgccacca | tcctgtacga | gatcctgctg | 840 |
| ggcaaggcca | ccctgtacgc | cgtgctggtg | tctggcctgg | tgctgatggc | catggtcaag | 900 |
| aagaagaaca | gcggcagcgg | cgccaccaac | ttcagcctgc | tgaaacaggc | cggcgacgtg | 960 |
| gaagagaacc | ctggccctat | gctgctggaa | catctgctga | tcatcctgtg | gatgcagctg | 1020 |
| acctgggtgt | ccggccagca | gctgaatcag | agcccccaga | gcatgttcat | ccaggaaggc | 1080 |
| gaggacgtgt | ccatgaactg | caccagcagc | agcatcttca | atacctggct | gtggtacaag | 1140 |
| caggacccccg | gcgaaggacc | cgtgctgctg | atcgccctgt | acaaagccgg | cgagctgacc | 1200 |
| agcaatggca | ggctgacagc | ccagttcggc | attacccgga | aggacagctt | cctgaacatc | 1260 |
| agcgcctcca | tccccagcga | cgtgggcatc | tatttctgcg | ccggacagca | gaactccggc | 1320 |
| ggctccaact | acaagctgac | cttcggcaag | ggcacactgc | tgacagtgaa | ccccaacatc | 1380 |
| cagaaccccg | agcccgccgt | gtaccagctg | aaggacccta | agccaggaca | gcaccctg | 1440 |
| tgcctgttca | ccgacttcga | cagccagatc | aacgtgccca | agaccatgga | aagcggcacc | 1500 |
| ttcatcaccg | acaagaccgt | gctggacatg | aaggccatgg | acagcaagag | caacggcgca | 1560 |
| atcgcctggt | ccaaccagac | cagcttcaca | tgccaggaca | tcttcaaaga | gacaaacgcc | 1620 |
| acctacccca | gctccgacgt | gcctgtgat | gccaccctga | ccgagaagtc | cttcgagaca | 1680 |
| gacatgaacc | tgaacttcca | gaatctgagc | gtgatgggcc | tgcgcatcct | gctgctgaag | 1740 |
| gtggccggct | taacctgct | gatgaccctg | cggctgtggt | ccagctga | | 1788 |

<210> SEQ ID NO 99
<211> LENGTH: 1782
<212> TYPE: DNA
<213> ORGANISM: Artificial Sequence
<220> FEATURE:
<223> OTHER INFORMATION: TCR3600 single chain nucleic acid TCR construct specific for HLA-DR4 epitope NY-ESO-1 116-135

<400> SEQUENCE: 99

| | | | | | |
|---|---|---|---|---|---|
| atggatactt | ggctcgtgtg | ctgggccatc | ttcagcctgc | tgaaggccgg | actgaccgag | 60 |
| cccgaagtga | cccagacacc | tagccaccaa | gtgacacaga | tgggccagga | agtgatcctg | 120 |

```
cgctgcgtgc ccatcagcaa ccacctgtac ttctactggt acagacagat cctggggcag    180
aaagtggaat ttctggtgtc cttctacaac aacgagatca gcgagaagtc cgagatcttc    240
gacgaccagt tcagcgtgga acggcccgac ggcagcaact tcaccctgaa gatcagaagc    300
accaagctgg aagatagcgc catgtacttt tgcgccagca gcgtgatcta cgagcagtac    360
ttcggccctg gcacccggct gaccgtgacc gaggatctga gaaacgtgac ccccccaag    420 gtgtccctgt tcgagcctag caaggccgag atcgccaaca gcagaaagc caccctcgtg    480 tgcctggcca gaggcttctt ccccgaccac gtggaactgt cttggtgggt caacggcaaa    540
gaggtgcaca cgcgcgtgtc caccgatccc caggcctaca agagagcaa ctacagctac    600 tgcctgtcca gcagactgcg ggtgtccgcc accttctggc acaaccccg gaaccacttc    660 agatgccagg tgcagtttca cggcctgagc gaagaggaca gtggcctga gggcagcccc    720 aagcccgtga ctcagaatat ctctgccgag gcatggggca gagccgactg tggcattacc    780
agcgccagct accatcaggg cgtgctgagc gccaccatcc tgtacgagat cctgctgggc    840
aaggccaccc tgtacgccgt gctggtgtct ggcctggtgc tgatggccat ggtcaagaag    900
aagaacagcg gcagcggcgc caccaacttt agtctgctga acaggccgg cgacgtggaa    960 gagaaccctg ccccatggt caaaatccgg cagttcctgc tggccatcct gtggctgcag   1020
ctgagctgtg tgtccgccgc caagaacgag gtggaacaga gcccccagaa cctgaccgct   1080
caggaaggcg agttcatcac catcaactgc agctacagcg tgggcatcag cgccctgcat   1140
tggctgcagc agcatcctgg cggaggcatc gtgtctctgt tcatgctgag cagcggaaag   1200
aagaagcacg gccggctgat cgccacaatc aacatccagg aaaagcacag cagcctgcac   1260
atcaccgcca gccaccctag agacagcgcc gtgtacatct gcgccgtgcc aatagcggc   1320 aacacccctc tggtgttcgg caagggcacc agactgagcg tgatcgccaa tatccagaac   1380
cccgagcctg ccgtgtacca gctgaaggac cctagaagcc aggacagcac cctgtgcctg   1440
ttcaccgact cgacagcca gatcaacgtg cccaagacca tggaaagcgg caccttcatc   1500
accgacaaga ccgtgctgga catgaaggcc atggacagca gagcaacgg cgccattgcc   1560 tggtccaacc agaccagctt cacatgccag gacatcttca agagacaaa cgccacctac   1620 cccagcagcg acgtgccctg tgatgccacc ctgaccgaga agtctttcga cagacatg   1680 aacctgaact tccagaatct gtccgtgatg ggcctgagaa tcctgctgct gaaagtggcc   1740
ggattcaacc tgctgatgac cctgcggctg tggtccagct ga                     1782

<210> SEQ ID NO 100
<211> LENGTH: 1782
<212> TYPE: DNA
<213> ORGANISM: Artificial Sequence
<220> FEATURE:
<223> OTHER INFORMATION: TCR5712 single chain nucleic acid TCR construct
      specific for HLA-DR4 epitope NY-ESO-1 116-135

<400> SEQUENCE: 100
atggatactt ggctcgtgtg ctgggccatc ttcagcctgc tgaaggccgg actgaccgag     60
cccgaagtga cccagacacc tagccaccaa gtgacacaga tgggccagga agtgatcctg    120
cgctgcgtgc ccatcagcaa ccacctgtac ttctactggt acagacagat cctggggcag    180
aaagtggaat ttctggtgtc cttctacaac aacgagatca gcgagaagtc cgagatcttc    240
gacgaccagt tcagcgtgga acggcccgac ggcagcaact tcaccctgaa gatcagaagc    300
accaagctgg aagatagcgc catgtacttt tgcgccagca gcatcatcta cgagcagtac    360
```

```
ttcggccctg gcacccggct gaccgtgacc gaggatctga gaaacgtgac ccccccaag      420 gtgtccctgt tcgagcctag caaggccgag atcgccaaca agcagaaagc cacccctcgtg   480 tgcctggcca gaggcttctt ccccgaccac gtggaactgt cttggtgggt caacggcaaa    540
gaggtgcaca gcggcgtgtc caccgatccc caggcctaca agagagcaa ctacagctac     600 tgcctgtcca gcagactgcg ggtgtccgcc accttctggc acaaccccg gaaccacttc     660 agatgccagg tgcagtttca cggcctgagc gaagaggaca gtggcctga gggcagcccc     720 aagcccgtga ctcagaatat ctctgccgag gcatggggca gagccgactg tggcattacc    780
agcgccagct accatcaggg cgtgctgagc gccaccatcc tgtacgagat cctgctgggc    840
aaggccaccc tgtacgccgt gctggtgtct ggcctggtgc tgatggccat ggtcaagaag    900
aagaacagcg gcagcggcgc caccaacttt agtctgctga acaggccgg cgacgtggaa     960 gagaaccctg gccccatggt caaaatccgg cagttcctgc tggccatcct gtggctgcag    1020
ctgagctgtg tgtccgccgc caagaacgag gtggaacaga gcccccagaa cctgaccgct    1080
caggaaggcg agttcatcac catcaactgc agctacagcg tgggcatcag cgccctgcat    1140
tggctgcagc agcatcctgg cggaggcatc gtgtctctgt tcatgctgag cagcggaaag    1200
aagaagcacg gccggctgat cgccacaatc aacatccagg aaaagcacag cagcctgcac    1260
atcaccgcca gccaccctag agacagcgcc gtgtacatct gcgccgtgcc aatagcggc    1320 aacacccctc tggtgttcgg caagggcacc agactgagcg tgatcgccaa tatccagaac    1380
cccgagcctg ccgtgtacca gctgaaggac cctagaagcc aggacagcac cctgtgcctg    1440
ttcaccgact cgacagcca gatcaacgtg cccaagacca tggaaagcgg caccttcatc    1500
accgacaaga ccgtgctgga catgaaggcc atggacagca gagcaacgg cgccattgcc    1560 tggtccaacc agaccagctt cacatgccag gacatcttca agagacaaa cgccacctac    1620 cccagcagcg acgtgcccctg tgatgccacc ctgaccgaga agtctttcga cagacatg    1680 aacctgaact tccagaatct gtccgtgatg ggcctgagaa tcctgctgct gaaagtggcc    1740
ggattcaacc tgctgatgac cctgcggctg tggtccagct ga                       1782
```

<210> SEQ ID NO 101
<211> LENGTH: 1782
<212> TYPE: DNA
<213> ORGANISM: Artificial Sequence
<220> FEATURE:
<223> OTHER INFORMATION: TCR5415 single chain nucleic acid TCR construct
      specific for HLA-DR4 epitope NY-ESO-1 116-135

<400> SEQUENCE: 101

```
atggatactt ggctcgtgtg ctgggccatc ttcagcctgc tgaaggccgg actgaccgag      60
cccgaagtga cccagacacc tagccaccaa gtgacacaga tgggccagga agtgatcctg     120
cgctgcgtgc ccatcagcaa ccacctgtac ttctactggt acagacagat cctggggcag     180
aaagtggaat tctggtgtc cttctacaac aacgagatca gcgagaagtc cgagatcttc     240
gacgaccagt tcagcgtgga acggcccgac ggcagcaact tcacccctga gatcagaagc     300
accaagctgg aagatagcgc catgtacttt tgcgccagca gcgtgtacta cgagcagtac     360
ttcggccctg gcacccggct gaccgtgacc gaggatctga gaaacgtgac ccccccaag     420 gtgtccctgt tcgagcctag caaggccgag atcgccaaca agcagaaagc cacccctcgtg   480 tgcctggcca gaggcttctt ccccgaccac gtggaactgt cttggtgggt caacggcaaa    540
gaggtgcaca gcggcgtgtc caccgatccc caggcctaca agagagcaa ctacagctac     600
```

| | |
|---|---|
| tgcctgtcca gcagactgcg ggtgtccgcc accttctggc acaacccccg gaaccacttc | 660 |
| agatgccagg tgcagtttca cggcctgagc gaagaggaca agtggcctga gggcagcccc | 720 |
| aagcccgtga ctcagaatat ctctgccgag gcatggggca gagccgactg tggcattacc | 780 |
| agcgccagct accatcaggg cgtgctgagc gccaccatcc tgtacgagat cctgctgggc | 840 |
| aaggccaccc tgtacgccgt gctggtgtct ggcctggtgc tgatggccat ggtcaagaag | 900 |
| aagaacagcg gcagcggcgc caccaacttt agtctgctga acaggccgg cgacgtggaa | 960 |
| gagaaccctg gccccatggt caaaatccgg cagttcctgc tggccatcct gtggctgcag | 1020 |
| ctgagctgtg tgtccgccgc caagaacgag gtggaacaga gccccagaa cctgaccgct | 1080 |
| caggaaggcg agttcatcac catcaactgc agctacagcg tgggcatcag cgccctgcat | 1140 |
| tggctgcagc agcatcctgg cggaggcatc gtgtctctgt tcatgctgag cagcggaaag | 1200 |
| aagaagcacg gccggctgat cgccacaatc aacatccagg aaaagcacag cagcctgcac | 1260 |
| atcaccgcca gccaccctag agacagcgcc gtgtacatct gcgccgtgcc caatagcggc | 1320 |
| aacacccctc tggtgttcgg caagggcacc agactgagcg tgatcgccaa tatccagaac | 1380 |
| cccgagcctg ccgtgtacca gctgaaggac cctagaagcc aggacagcac cctgtgcctg | 1440 |
| ttcaccgact cgacagcca gatcaacgtg cccaagacca tggaaagcgg caccttcatc | 1500 |
| accgacaaga ccgtgctgga catgaaggcc atggacagca gagcaacgg cgccattgcc | 1560 |
| tggtccaacc agaccagctt cacatgccag gacatcttca agagacaaa cgccacctac | 1620 |
| cccagcagcg acgtgccctg tgatgccacc ctgaccgaga gtctttcga cagacatg | 1680 |
| aacctgaact tccagaatct gtccgtgatg ggcctgagaa tcctgctgct gaaagtggcc | 1740 |
| ggattcaacc tgctgatgac cctgcggctg tggtccagct ga | 1782 |

<210> SEQ ID NO 102
<211> LENGTH: 1800
<212> TYPE: DNA
<213> ORGANISM: Artificial Sequence
<220> FEATURE:
<223> OTHER INFORMATION: TCR5713 single chain nucleic acid TCR construct specific for HLA-DR4 epitope NY-ESO-1 116-135

<400> SEQUENCE: 102

| | |
|---|---|
| atggatactt ggctcgtgtg ctgggccatc ttcagcctgc tgaaggccgg actgaccgag | 60 |
| cccgaagtga cccagacacc tagccaccaa gtgacacaga tgggccagga agtgatcctg | 120 |
| cgctgcgtgc ccatcagcaa ccacctgtac ttctactggt acagacagat cctggggcag | 180 |
| aaagtggaat tctggtgtc cttctacaac aacgagatca gcgagaagtc cgagatcttc | 240 |
| gacgaccagt tcagcgtgga acggcccgac ggcagcaact tcaccctgaa gatcagaagc | 300 |
| accaagctgg aagatagcgc catgtacttt tgcgccagca gctctggact ggccggcgtg | 360 |
| acaggcgagc tgttttttgg cgagggcagc agactgaccg tgctggaaga tctgcggaac | 420 |
| gtgaccccc ccaaggtgtc cctgttcgag cctagcaagg ccgagatcgc caacaagcag | 480 |
| aaagccaccc tcgtgtgcct ggccagaggc ttcttccccg accacgtgga actgtcttgg | 540 |
| tgggtcaacg gcaaagaggt gcacagcggc gtgtccaccg atcccaggc ctacaaagag | 600 |
| agcaactaca gctactgcct gtcctcccgg ctgagagtgt ccgccacctt ctggcacaac | 660 |
| ccccggaacc acttcagatg ccaggtgcag tttcacggcc tgagcgaaga ggacaagtgg | 720 |
| cctgagggca gccccaagcc cgtgactcag aatatctctg ccgaggcatg ggcagagcc | 780 |
| gactgtggca ttaccagcgc cagctaccat cagggcgtgc tgagcgccac catcctgtac | 840 |

```
gagatcctgc tgggcaaggc caccctgtac gccgtgctgg tgtcaggcct ggtgctgatg    900
gccatggtca agaagaagaa cagcggcagc ggcgccacca actttagtct gctgaaacag    960
gccggcgacg tggaagagaa ccctggcccc atgaagacct cgccggctt cagcttcctg   1020 ttcctgtggc tgcagctgga ctgcatgagc agaggcgagg acgtggaaca gagcctgttt   1080
ctgagcgtgc gcgagggcga cagcagcgtg atcaattgca cctacaccga cagctccagc   1140
acatacctgt actggtataa gcaggaaccc ggcgctggcc tgcagctgct gacctacatc   1200
ttctccaaca tggacatgaa gcaggaccag cggctgacag tgctgctgaa caagaaggac   1260
aagcacctga gcctgcggat cgccgatacc cagacaggcg actccgccat ctatttctgc   1320
gccgaggcca atcaggccgg caccgccctg atctttggca agggcacaac actgagcgtg   1380
tccagcaaca tccagaaccc cgagcccgcc gtgtaccagc tgaaggaccc tagaagccag   1440
gacagcaccc tgtgcctgtt caccgacttc gacagccaga tcaacgtgcc caagaccatg   1500
gaaagcggca ccttcatcac cgacaagact gtgctggata tgaaggccat ggacagcaag   1560
agcaacggcg ccattgcctg gtccaaccag accagcttca catgccagga catcttcaaa   1620
gagacaaacg ccacctaccc cagcagcgac gtgccctgtg atgccaccct gaccgagaag   1680
tctttcgaga cagacatgaa cctgaacttc cagaacctga gcgtgatggg cctgagaatc   1740
ctgctgctga aggtggccgg cttcaacctg ctgatgaccc tgagactgtg gtccagctga   1800

<210> SEQ ID NO 103
<211> LENGTH: 9
<212> TYPE: PRT
<213> ORGANISM: Homo sapiens
<220> FEATURE:
<223> OTHER INFORMATION: HLA-A2 epitope NY-ESO-1 157-165

<400> SEQUENCE: 103

Ser Leu Leu Met Trp Ile Thr Gln Cys
1               5

<210> SEQ ID NO 104
<211> LENGTH: 133
<212> TYPE: PRT
<213> ORGANISM: Homo sapiens
<220> FEATURE:
<223> OTHER INFORMATION: TCR alpha chain specific for HLA-A2 epitope
      NY-ESO-1 157-165, variable region

<400> SEQUENCE: 104

Met Lys Ser Leu Arg Val Leu Val Ile Leu Trp Leu Gln Leu Ser
1               5                   10                  15

Trp Val Trp Ser Gln Gly Gln Gln Val Met Gln Ile Pro Gln Tyr Gln
                20                  25                  30

His Val Gln Glu Gly Glu Asp Phe Thr Thr Tyr Cys Asn Ser Ser Thr
            35                  40                  45

Thr Leu Ser Asn Ile Gln Trp Tyr Lys Gln Arg Pro Gly Gly His Pro
        50                  55                  60

Val Phe Leu Ile Gln Leu Val Lys Ser Gly Glu Val Lys Lys Gln Lys
65                  70                  75                  80

Arg Leu Thr Phe Gln Phe Gly Glu Ala Lys Lys Asn Ser Ser Leu His
                85                  90                  95

Ile Thr Ala Thr Gln Thr Thr Asp Val Gly Thr Tyr Phe Cys Ala Gly
            100                 105                 110

Glu Gly Asn Tyr Gly Gln Asn Phe Val Phe Gly Pro Gly Thr Arg Leu
        115                 120                 125
```

Ser Val Leu Pro Asp
    130

<210> SEQ ID NO 105
<211> LENGTH: 400
<212> TYPE: DNA
<213> ORGANISM: Artificial Sequence
<220> FEATURE:
<223> OTHER INFORMATION: TCR alpha chain specific for HLA-A2 epitope
      NY-ESO-1 157-165, variable region

<400> SEQUENCE: 105
atgaagagcc tgcgcgtgct gctggtcatc ctgtggctgc aattgtcttg ggtctggtca      60
caggggcagc aggtcatgca gattccacag tatcagcacg tccaggaggg ggaggacttc     120
actacatatt gtaacagctc caccacactg tcaaatatcc agtggtacaa gcagcgacca     180
ggaggacacc cagtgttcct gattcagctg gtgaagagcg gcgaggtcaa gaaacagaaa     240
agactgacct tccagtttgg cgaagccaag aaaaactcta gtctgcatat cacagctact     300
cagactaccg acgtcggcac ctacttttgc gcaggagagg gcaactatgg gcagaatttc     360
gtgtttgggc tggaacaag gctgtctgtc ctgcccgata                            400

<210> SEQ ID NO 106
<211> LENGTH: 269
<212> TYPE: PRT
<213> ORGANISM: Artificial Sequence
<220> FEATURE:
<223> OTHER INFORMATION: TCR alpha chain specific for HLA-A2 epitope
      NY-ESO-1 157-165

<400> SEQUENCE: 106

Met Lys Ser Leu Arg Val Leu Val Ile Leu Trp Leu Gln Leu Ser
1               5                   10                  15

Trp Val Trp Ser Gln Gly Gln Gln Val Met Gln Ile Pro Gln Tyr Gln
                20                  25                  30

His Val Gln Glu Gly Glu Asp Phe Thr Thr Tyr Cys Asn Ser Ser Thr
            35                  40                  45

Thr Leu Ser Asn Ile Gln Trp Tyr Lys Gln Arg Pro Gly Gly His Pro
        50                  55                  60

Val Phe Leu Ile Gln Leu Val Lys Ser Gly Glu Val Lys Lys Gln Lys
65                  70                  75                  80

Arg Leu Thr Phe Gln Phe Gly Glu Ala Lys Lys Asn Ser Ser Leu His
                85                  90                  95

Ile Thr Ala Thr Gln Thr Thr Asp Val Gly Thr Tyr Phe Cys Ala Gly
            100                 105                 110

Glu Gly Asn Tyr Gly Gln Asn Phe Val Phe Gly Pro Gly Thr Arg Leu
        115                 120                 125

Ser Val Leu Pro Asp Ile Gln Asn Pro Glu Pro Ala Val Tyr Gln Leu
    130                 135                 140

Lys Asp Pro Arg Ser Gln Asp Ser Thr Leu Cys Leu Phe Thr Asp Phe
145                 150                 155                 160

Asp Ser Gln Ile Asn Val Pro Lys Thr Met Glu Ser Gly Thr Phe Ile
                165                 170                 175

Thr Asp Lys Cys Val Leu Asp Met Lys Ala Met Asp Ser Lys Ser Asn
            180                 185                 190

Gly Ala Ile Ala Trp Ser Asn Gln Thr Ser Phe Thr Cys Gln Asp Ile
        195                 200                 205

```
Phe Lys Glu Thr Asn Ala Thr Tyr Pro Ser Ser Asp Val Pro Cys Asp
    210                 215                 220

Ala Thr Leu Thr Glu Lys Ser Phe Glu Thr Asp Met Asn Leu Asn Phe
225                 230                 235                 240

Gln Asn Leu Ser Val Met Gly Leu Arg Ile Leu Leu Leu Lys Val Ala
            245                 250                 255

Gly Phe Asn Leu Leu Met Thr Leu Arg Leu Trp Ser Ser
            260                 265
```

<210> SEQ ID NO 107
<211> LENGTH: 810
<212> TYPE: DNA
<213> ORGANISM: Artificial Sequence
<220> FEATURE:
<223> OTHER INFORMATION: TCR alpha chain specific for HLA-A2 epitope
      NY-ESO-1 157-165

<400> SEQUENCE: 107

```
atgaagagcc tgcgcgtgct gctggtcatc ctgtggctgc aattgtcttg ggtctggtca      60
cagggcagc aggtcatgca gattccacag tatcagcacg tccaggaggg ggaggacttc     120
actacatatt gtaacagctc caccacactg tcaaatatcc agtggtacaa gcagcgacca     180
ggaggacacc cagtgttcct gattcagctg gtgaagagcg gcgaggtcaa gaaacagaaa     240
agactgacct tccagtttgg cgaagccaag aaaaactcta gtctgcatat acagcactct     300
cagactaccg acgtcggcac ctacttttgc gcaggagagg gcaactatgg cagaatttc      360
gtgtttgggc tggaacaag gctgtctgtc ctgcccgata ttcagaatcc gaacctgcc      420
gtataccagc tgaaggaccc ccgatctcag gatagtactc tgtgcctgtt caccgacttt     480
gatagtcaga tcaatgtgcc taaaaccatg gaatccggaa cttttattac cgacaagtgc     540
gtgctggata tgaaagccat ggacagtaag tcaaacggcg ccatcgcttg gagcaatcag     600
acatccttca cttgccagga tatcttcaag gagaccaacg caacataccc atcctctgac     660
gtgccctgtg atgccaccct gacagagaag tctttcgaaa cagacatgaa cctgaatttt     720
cagaatctga gcgtgatggg cctgagaatc ctgctgctga aggtcgctgg gttttaatctg     780
ctgatgacac tgcggctgtg gtcctcatga                                     810
```

<210> SEQ ID NO 108
<211> LENGTH: 134
<212> TYPE: PRT
<213> ORGANISM: Homo sapiens
<220> FEATURE:
<223> OTHER INFORMATION: TCR beta chain specific for HLA-A2 epitope
      NY-ESO-1 157-165, variable region

<400> SEQUENCE: 108

```
Met Gly Ser Trp Thr Leu Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asp Tyr Leu Phe Trp Tyr Arg Gln Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95
```

```
Lys Ile Gln Pro Ser Glu Pro Arg Asp Ser Ala Val Tyr Phe Cys Ala
            100                 105                 110

Ser Asn Ile Ala Gly Gly Tyr Asn Glu Gln Phe Phe Gly Pro Gly Thr
            115                 120                 125

Arg Leu Thr Val Leu Glu
        130

<210> SEQ ID NO 109
<211> LENGTH: 400
<212> TYPE: DNA
<213> ORGANISM: Artificial Sequence
<220> FEATURE:
<223> OTHER INFORMATION: TCR beta chain specific for HLA-A2 epitope
      NY-ESO-1 157-165, variable region

<400> SEQUENCE: 109
atggggagct ggaccctgtg ttgtgtgagc ctgtgtatcc tggtggcaaa gcataccgac    60
gctggagtga ttcagagccc tagacatgaa gtgactgaaa tggggcagga ggtcaccctg   120
cgatgcaagc ccatctccgg acacgactac ctgttctggt atcggcagac aatgatgaga   180
ggcctggagc tgctgatcta ctttaacaat aacgtgccca tcgacgattc agggatgccc   240
gaagacaggt tcagcgcaaa gatgcctaat gccagctttt ccaccctgaa aatccagccc   300
tctgaacctc gcgatagtgc tgtgtacttc tgtgccagta atattgctgg cgggtataac   360
gagcagttct ttggaccagg caccagactg acagtcctgg                         400

<210> SEQ ID NO 110
<211> LENGTH: 309
<212> TYPE: PRT
<213> ORGANISM: Artificial Sequence
<220> FEATURE:
<223> OTHER INFORMATION: TCR beta chain specific for HLA-A2 epitope
      NY-ESO-1 157-165

<400> SEQUENCE: 110

Met Gly Ser Trp Thr Leu Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asp Tyr Leu Phe Trp Tyr Arg Gln Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Asn Ile Ala Gly Gly Tyr Asn Glu Gln Phe Phe Gly Pro Gly Thr
            115                 120                 125

Arg Leu Thr Val Leu Glu Asp Leu Arg Asn Val Thr Pro Pro Lys Val
        130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175
```

Ser Trp Trp Val Asn Gly Lys Glu Val His Ser Gly Val Cys Thr Asp
                180                 185                 190

Pro Gln Ala Tyr Lys Glu Ser Asn Tyr Ser Tyr Cys Leu Ser Ser Arg
                195                 200                 205

Leu Arg Val Ser Ala Thr Phe Trp His Asn Pro Arg Asn His Phe Arg
        210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr His Gln Gly Val Leu
        260                 265                 270

Ser Ala Thr Ile Leu Tyr Glu Ile Leu Leu Gly Lys Ala Thr Leu Tyr
        275                 280                 285

Ala Val Leu Val Ser Gly Leu Val Leu Met Ala Met Val Lys Lys Lys
        290                 295                 300

Asn Ser Thr Gly Ala
305

<210> SEQ ID NO 111
<211> LENGTH: 921
<212> TYPE: DNA
<213> ORGANISM: Artificial Sequence
<220> FEATURE:
<223> OTHER INFORMATION: TCR beat chain specific for HLA-A2 epitope
      NY-ESO-1 157-165

<400> SEQUENCE: 111
atggggagct ggaccctgtg ttgtgtgagc ctgtgtatcc tggtggcaaa gcataccgac      60
gctggagtga ttcagagccc tagacatgaa gtgactgaaa tggggcagga ggtcaccctg     120
cgatgcaagc ccatctccgg acacgactac ctgttctggt atcggcagac aatgatgaga     180
ggcctggagc tgctgatcta ctttaacaat aacgtgccca tcgacgattc agggatgccc     240
gaagacaggt tcagcgcaaa gatgcctaat gccagctttt ccaccctgaa atccagccc     300 tctgaacctc gcgatagtgc tgtgtacttc tgtgccagta atattgctgg cgggtataac     360
gagcagttct ttggaccagg caccagactg acagtcctgg aagatctacg taacgtgaca     420
ccacccaaag tctcactgtt tgagcctagc aaggcagaaa ttgccaacaa gcagaaggcc     480
accctggtgt gcctggcaag agggttcttt ccagatcacg tggagctgtc ctggtgggtc     540
aacggcaaag aagtgcattc tggggtctgc accgaccccc aggcttacaa ggagagtaat     600
tactcatatt gtctgtcaag ccggctgaga gtgtccgcca cattctggca caaccctagg     660
aatcatttcc gctgccaggt ccagtttcac ggcctgagtg aggaagataa atggccagag     720
gggtcaccta agccagtgac acagaacatc agcgcagaag cctggggacg agcagactgt     780
ggcattacta gcgcctccta tcatcagggc gtgctgagcg ccactatcct gtacgagatt     840
ctgctgggaa aggccaccct gtatgctgtg ctggtctccg gcctggtgct gatggccatg     900
gtcaagaaaa agaactcttg a                                              921

<210> SEQ ID NO 112
<211> LENGTH: 1794
<212> TYPE: DNA
<213> ORGANISM: Artificial Sequence
<220> FEATURE:
<223> OTHER INFORMATION: single chain nucleic acid TCR construct
      specific for HLA-A2 epitope NY-ESO-1 157-165

```
<400> SEQUENCE: 112
atggggagct ggaccctgtg ttgtgtgagc ctgtgtatcc tggtggcaaa gcataccgac      60
gctggagtga ttcagagccc tagacatgaa gtgactgaaa tggggcagga ggtcaccctg     120
cgatgcaagc ccatctccgg acacgactac ctgttctggt atcggcagac aatgatgaga     180
ggcctggagc tgctgatcta ctttaacaat aacgtgccca tcgacgattc agggatgccc     240
gaagacaggt tcagcgcaaa gatgcctaat gccagctttt ccaccctgaa aatccagccc     300
tctgaacctc gcgatagtgc tgtgtacttc tgtgccagta atattgctgg cgggtataac     360
gagcagttct ttggaccagg caccagactg acagtcctgg aagatctacg taacgtgaca     420
ccacccaaag tctcactgtt tgagcctagc aaggcagaaa ttgccaacaa gcagaaggcc     480
accctggtgt gcctggcaag agggttcttt ccagatcacg tggagctgtc ctggtgggtc     540
aacggcaaag aagtgcattc tggggtctgc accgaccccc aggcttacaa ggagagtaat     600
tactcatatt gtctgtcaag ccggctgaga gtgtccgcca cattctggca caaccctagg     660
aatcatttcc gctgccaggt ccagtttcac ggcctgagtg aggaagataa atggccagag     720
gggtcaccta agccagtgac acagaacatc agcgcagaag cctggggacg agcagactgt     780
ggcattacta gcgcctccta tcatcagggc gtgctgagcg ccactatcct gtacgagatt     840
ctgctgggaa aggccaccct gtatgctgtg ctggtctccg gcctggtgct gatggccatg     900
gtcaagaaaa agaactctgg gagtggagcc acaaatttct ctctgctgaa acaggctgga     960
gatgtggagg aaaaccccgg ccctatgaag agcctgcgcg tgctgctggt catcctgtgg    1020
ctgcaattgt cttgggtctg gtcacagggg cagcaggtca tgcagattcc acagtatcag    1080
cacgtccagg aggggagga cttcactaca tattgtaaca gctccaccac actgtcaaat    1140
atccagtggt acaagcagcg accaggagga cacccagtgt tcctgattca gctggtgaag    1200
agcggcgagg tcaagaaaca gaaaagactg accttccagt ttggcgaagc caagaaaaac    1260
tctagtctgc atatcacagc tactcagact accgacgtcg gcacctactt ttgcgcagga    1320
gagggcaact atgggcagaa tttcgtgttt gggcctggaa caaggctgtc tgtcctgccc    1380
gatattcaga atcccgaacc tgccgtatac cagctgaagg acccccgatc tcaggatagt    1440
actctgtgcc tgttcaccga cttttgatagt cagatcaatg tgcctaaaac catggaatcc    1500
ggaactttta ttaccgacaa gtgcgtgctg gatatgaaag ccatggacag taagtcaaac    1560
ggcgccatcg cttggagcaa tcagacatcc ttcacttgcc aggatatctt caaggagacc    1620
aacgcaacat acccatcctc tgacgtgccc tgtgatgcca ccctgacaga gaagtctttc    1680
gaaacagaca tgaacctgaa ttttcagaat ctgagcgtga tgggcctgag aatcctgctg    1740
ctgaaggtcg ctgggtttaa tctgctgatg acactgcggc tgtggtcctc atga          1794
```

UNITED STATES PATENT AND TRADEMARK OFFICE
CERTIFICATE OF CORRECTION

PATENT NO. : 10,781,243 B2
APPLICATION NO. : 15/558021
DATED : September 22, 2020
INVENTOR(S) : Thomas Blankenstein et al.

It is certified that error appears in the above-identified patent and that said Letters Patent is hereby corrected as shown below:

In the Specification

In the Description:
Column 2, Line 6: "Unique TRAY" should read "Unique TRAV";
Column 10, Line 48-49: "fluorescein isothiocyanate (MC)" should read "fluorescein isothiocyanate (FITC)";

In the Claims

Claim 1, Line 58: "human MEW" should read "human MHC".

Signed and Sealed this
Twelfth Day of January, 2021

Andrei Iancu
*Director of the United States Patent and Trademark Office*